United States Patent
Kumar et al.

(10) Patent No.: US 10,844,386 B2
(45) Date of Patent: Nov. 24, 2020

(54) APTAMER BIOSENSORS USEFUL FOR DETECTING HORMONES, HORMONE MIMICS, AND METABOLITES THEREOF

(71) Applicant: AURAMER BIO LIMITED, Lower Hutt (NZ)

(72) Inventors: Shalen Kumar, Lower Hutt (NZ); Kenneth McNatty, Wellington (NZ)

(73) Assignee: AURAMER BIO LIMITED, Lower Hutt (NZ)

( * ) Notice: Subject to any disclaimer, the term of this patent is extended or adjusted under 35 U.S.C. 154(b) by 370 days.

(21) Appl. No.: 15/752,201

(22) PCT Filed: Aug. 11, 2016

(86) PCT No.: PCT/IB2016/054839
§ 371 (c)(1),
(2) Date: Feb. 12, 2018

(87) PCT Pub. No.: WO2017/025921
PCT Pub. Date: Feb. 16, 2017

(65) Prior Publication Data
US 2020/0208156 A1    Jul. 2, 2020

Related U.S. Application Data

(60) Provisional application No. 62/204,577, filed on Aug. 13, 2015.

(51) Int. Cl.
| | |
|---|---|
| *C12N 15/11* | (2006.01) |
| *C12N 15/115* | (2010.01) |
| *G01N 33/543* | (2006.01) |
| *G01N 33/74* | (2006.01) |

(52) U.S. Cl.
CPC ..... *C12N 15/115* (2013.01); *G01N 33/54306* (2013.01); *G01N 33/743* (2013.01); *C12N 2310/16* (2013.01)

(58) Field of Classification Search
None
See application file for complete search history.

(56) References Cited

U.S. PATENT DOCUMENTS

| | | |
|---|---|---|
| 2005/0037394 A1 | 2/2005 | Keefe et al. |
| 2012/0015354 A1 | 1/2012 | Kim |
| 2012/0088232 A1 | 4/2012 | Wanekaya et al. |
| 2012/0123096 A1 | 5/2012 | Bruno et al. |
| 2012/0149889 A1 | 6/2012 | Bruno |
| 2014/0349873 A1 | 11/2014 | Bruno et al. |

FOREIGN PATENT DOCUMENTS

| | | |
|---|---|---|
| WO | WO-2002/026932 A3 | 6/2002 |
| WO | WO-2012/130948 A1 | 10/2012 |
| WO | WO-2014/123430 A1 | 8/2014 |
| WO | WO-2015/057177 A2 | 4/2015 |
| WO | WO-2015/174863 A1 | 11/2015 |

OTHER PUBLICATIONS

Jimenez et al, Aptamer-Based Label-Free Impedimetric Biosensor for Detection of Progesterone, Anal. Chem, Dec. 2014, 87: 1075-1082 (Year: 2014).*
Allmyr et al., "Determination of Triclosan as its Pentafluorobenzoyl Ester in Human Plasma and Milk Using Electron Capture Negative Ionization Mass Spectrometry", Anal. Chem., 78:6542-6546 (2006).
Alsager et al., "Small molecule detection in solution via the size contraction response of aptamer functionalized nanoparticles", Biosens. Bioelectron, 57:262-268 (2014).
Alsager, Omar A., et al. "Ultrasensitive Colorimetric Detection of 17β-Estradiol: The Effect of Shortening DNA Aptamer Sequences.", Analytical Chemistry, 87.8:4201-4209 (2015).
Blackwell et al., "Differences and similarities in DNA-binding preferences of MyoD and E2A protein complexes revealed by binding site selection", Science, 250:1104-1110 (1990).
Brown et al., "Nucleotide Surface Interactions in DNA-Modified Au-Nanoparticle Conjugates: Sequence Effects on Reactivity and Hybridization", J. Phys. Chem., C 112:7517-7521 (2008).
Campbell et al., "Biologically directed environmental monitoring, fate, and transport of estrogenic endocrine disrupting compounds in water: A review", Chemosphere, 65:1265-1280 (2006).
Cekan et al., "Folding of the cocaine aptamer studied by EPR and fluorescence spectroscopies using the bifunctional spectroscopic probe C", Nucleic Acids Res., 37:3990-3995 (2009).
Cho et al., "Applications of Aptamers as Sensors", Ann. Rev. Anal. Chem., 2:241-264 (2009).
Cruz-Aguado et al., "Determination of Ochratoxin A with a DNA Aptamer", J. Agric. Food Chem., 56:10456-10461 (2008).
Ellington et al., "In vitro selection of RNA molecules that bind specific ligands", Nature, 346:818-822 (1990).
Ge et al., "Controllable Synthesis of Pd Nanocatalysts for Direct Formic Acid Fuel Cell (DFAFC) Application: From Pd Hollow Nanospheres to Pd Nanoparticles", J. Phys. Chem., C 111:17305-17310 (2007).
Grabar et al., "Preparation and Characterization of Au Colloid Monolayers", Anal. Chem., 67:735-743 (1995).
Haiss et al., "Determination of size and concentration of gold nanoparticles from UV—Vis Spectra", Anal. Chem., 79:4215-4221 (2007).
He et al., "Isolation and Identification of the DNA Aptamer Target to Acetamiprid", J. Agric. Food Chem., 59:1582-1586 (2011).
Hileman, Bisphenol A Vexations, Chemical and Engineering News, 85:31-33 (2007).

(Continued)

*Primary Examiner* — Ekaterina Poliakova-Georgantas
(74) *Attorney, Agent, or Firm* — Marshall, Gerstein & Borun LLP

(57) ABSTRACT

The present invention provides polynucleotides that bind to small molecules and methods of using the polynucleotides. In some embodiments, a method comprises detecting a small molecule with a polynucleotide. In other embodiments, a method comprises administering a polynucleotide to inhibit the action of a small molecule. In some embodiments, the small molecule is a hormone, a hormone mimic, phytoestrogen, opiate, opioid, endocrine disrupting compound, metabolite thereof, or variant thereof.

15 Claims, 4 Drawing Sheets
Specification includes a Sequence Listing.

(56) References Cited

OTHER PUBLICATIONS

Huizenga et al., "A DNA Aptamer That Binds Adenosine and ATP", *Biochemistry*, 34:656-665 (1995).
International Preliminary Report on Patentability, PCT/IB2016/054839 (dated Feb. 13, 2018).
International Search Report and Written Opinion, PCT/IB2016/054839 (dated Nov. 22, 2016).
Jana et al., "Seed-Mediated Growth Approach for Shape-Controlled Synthesis of Spheroidal and Rod-like Gold Nanoparticles Using a Surfactant Template", *Adv. Mater.*, 13:1389-1393 (2001).
Jin et al., "What Controls the Melting Properties of DNA-Linked Gold Nanoparticle Assemblies?", *J. Am. Chem. Soc.*, 125:1643-1654 (2003).
Jo et al., "Development of Single-Stranded DNA Aptamers for Specific Bisphenol A Detection", *Oligonucleotides.*, 21:85-91 (2011).
Karsisiotis et al., "Topological Characterization of Nucleic Acid G-Quadruplexes by UV Absorption and Circular Dichroism", *Angew. Chem. Int. Ed. Engl.*, 50:10645-10648 (2011).
Kim et al., "A novel colorimetric aptasensor using gold nanoparticle for a highly sensitive and specific detection of oxytetracycline", *Bioelectron.*, 26:1644-1649 (2010).
Kim et al., "Electrochemical detection of 17β-estradiol using DNA aptamer immobilized gold electrode chip", *Biosens. Bioelectron.*, 22:2525-2531 (2007).
Li et al., "Colorimetric detection of DNA sequences based on electrostatic interactions with unmodified gold nanoparticles", *Proc. Natl. Acad. Sci. U.S.A.*, 101:14036-14039 (2004).
Liu et al., "Highly sensitive colorimetric detection of 17β-estradiol using split DNA aptamers immobilized on unmodified gold nanoparticles", Scientific Reports, Abstract, 2014, vol. 4, article 7571.
McKeague et al., "Challenges and Opportunities for Small Molecule Aptamer Development", *J. Nucleic Acids*, 748913, pp. 1-20 (2012).
McManus et al., "Assessing the Amount of Quadruplex Structures Present within G2-Tract Synthetic Random-Sequence DNA Libraries", *PLOS One*, vol. 8, e64131, pp. 1-10 (2013).
Mei et al., "Ultrasensitive one-step rapid visual detection in bisphenol A in water samples by label-free aptasensor", *Biosens. Bioelectron.*, 39:26-30 (2013).
Nonaka et al., Screening and Improvement of an Anti-VEGF DNA Aptamer, Molecules, 15:215-225 (2010).
Olowu et al., "Electrochemical Aptasensor for Endocrine Disrupting 17β-Estradio Based on a Poly(3,4-ethylenedioxylthiopene)-Gold Nanocomposite Platform", *Sensors*, 10:9872-9890 (2010).
Olowu et al., "Spectroelectrochemical Dynamics of Dendritic Poly (Propylene imine)-Polythiophene Start Copolymer Aptameric 17β-Estradiol Biosensor", *Int. J. Electrochem. Sci.*, 6:1686-1708 (2011).
Redel et al., "Synthesis of Co, Rh and Ir nanoparticles from metal carbonyls in ionic liquids and their use as biphasic liquid-liquid hydrogenation nanocatalysts for cyclohexane", *J. Organomet. Chem.*, 694:1069-1075 (2009).
Shi et al., "Aptamer-based colorimetric sensing of acetamiprid in soil samples: Sensitivity, selectivity and mechanism", *J. Hazard. Mater.*, 260:754-761 (2013).
Skakkebaek et al., "Testicular dysgenesis syndrome: an increasingly common developmental disorder with environmental aspects", *Human Reproduction*, 16:972-978 (2001).
Song et al., "Aptamer-based biosensors", *Trends in Analytical Chemistry*, 27:108-117 (2008).
Song et al., "Gold nanoparticle-based colorimetric detection of kanamycin using a DNA aptamer", *Anal. Biochem.*, 415:175-181 (2011).
Stoltenburg et al., "SELEX-A (r)evoluntionary method to generate high-affinity nucleic acid ligands", *Biomol. Eng.*, 24:381-403 (2007).
Teranishi et al., "Size Control of Monodispersed Pt Nanoparticles and Their 2D Organization by Electrophoretic Deposition", *J. Phys. Chem.*, B 103:3818-3827 (1999).
Tuerk et al., "Systematic Evolution of Ligands by Exponential Enrichment: RNA Ligands to Bacteriophase T4 DNA Polymerase", *Science*, 249:505-510 (1990).
van-Pelt et al., "Ontogeny of Estrogen Receptor-B Expression in Rat Testis", *Endocrinology*, 140:478-483 (2001).
Vandenberg et al., "Hormones and Endocrine-Disrupting Chemicals: Low-Dose Effects and Nonmonotonic Dose Respnoses", *Endocrine Reviews*, 33: 378-455 (2012).
Vanschoenbeek et al., "Aptamers targeting different functional groups of 17β-estradiol", *The Journal of Steroid Biochemistry and Molecular Biology*, 147:10-16 (2014).
Vorlickova et al., "Circular Dichroism Spectroscopy of DNA: From Duplexes to Quadruplexes", *Chirality*, 24:691-698 (2012).
Wu et al., "Synthesis of high-concentration Cu nanoparticles in aqueous CTAB solutions", *J. Colloid Interface Sci.*, 273:165-169 (2004).
Wu et al., "Ultrasensitive one-step rapid detection of ochratoxin A by the folding-based electrochemical aptasensor", *Anal. Chim. Acta*, 753:27-31 (2012).
Xue et al., "Electrochemical astasensor for the determination of bisphenol A in drinking water", *Microchim. Acta*, 180:109-115 (2013).
Yang et al., "Aptamer-based colorimetric biosensing of Ochratoxin A using unmodified gold nanoparticles indicator", *Biosens. Bioelectron.*, 26:2724-2727 (2011).
Yin et al., "Synthesis and characterization of stable aqueous dispersions of silver nanoparticles through the Tollens process", *J. Mater. Chem.*, 12:522-527 (2002).
Zhao et al., "Design of Gold Nanoparticle-Based Colorimetric Biosensing Assays", *Chembiochem.*, 9:2363-2371 (2008).
Zheng et al., "Aptamer-based colorimetric biosensing of dopamine using unmodified gold nanoparticles", *Sensors Actuators B Chem.*, 156:95-99 (2011).

\* cited by examiner

Bisphenol A

17α-ethynylestradiol

SEQUENCE LISTING

<160> NUMBER OF SEQ ID NOS: 147

<210> SEQ ID NO 1
<211> LENGTH: 75
<212> TYPE: DNA
<213> ORGANISM: Artificial Sequence
<220> FEATURE:
<223> OTHER INFORMATION: Aptamer

<400> SEQUENCE: 1
atacgagctt gttcaatagc ctttaaactt gtatggggat ttagaattct ttcctccctg    60
atagtaagag caatc                                                    75

<210> SEQ ID NO 2
<211> LENGTH: 40
<212> TYPE: DNA
<213> ORGANISM: Artificial Sequence
<220> FEATURE:
<223> OTHER INFORMATION: Aptamer

<400> SEQUENCE: 2
gcctttaaac ttgtatgggg atttagaatt ctttcctccc                          40

<210> SEQ ID NO 3
<211> LENGTH: 27
<212> TYPE: DNA
<213> ORGANISM: Artificial Sequence
<220> FEATURE:
<223> OTHER INFORMATION: Aptamer

<400> SEQUENCE: 3 tagccttta acttgtatgg ggattta                                         27

<210> SEQ ID NO 4
<211> LENGTH: 75
<212> TYPE: DNA
<213> ORGANISM: Artificial Sequence
<220> FEATURE:
<223> OTHER INFORMATION: Aptamer

<400> SEQUENCE: 4
atacgagctt gttcaatatg tttcttttc catgctagtt ttttagtctt ttttacaatg    60
atagtaagag caatc                                                    75

<210> SEQ ID NO 5
<211> LENGTH: 40
<212> TYPE: DNA
<213> ORGANISM: Artificial Sequence
<220> FEATURE:
<223> OTHER INFORMATION: Aptamer

<400> SEQUENCE: 5
tgtttctttt tccatgctag tttttagtc ttttttacaa                          40

<210> SEQ ID NO 6
<211> LENGTH: 75
<212> TYPE: DNA
<213> ORGANISM: Artificial Sequence
<220> FEATURE:
<223> OTHER INFORMATION: Aptamer

<400> SEQUENCE: 6
atacgagctt gttcaatata gtagagattc acatttgtgc ctatgatcta tttccggatg    60
atagtaagag caatc                                                    75

<210> SEQ ID NO 7
<211> LENGTH: 40
<212> TYPE: DNA
<213> ORGANISM: Artificial Sequence
<220> FEATURE:
<223> OTHER INFORMATION: Aptamer

<400> SEQUENCE: 7
tagtagagat tcacatttgt gcctatgatc tatttccgga              40

<210> SEQ ID NO 8
<211> LENGTH: 28
<212> TYPE: DNA
<213> ORGANISM: Artificial Sequence
<220> FEATURE:
<223> OTHER INFORMATION: Aptamer

<400> SEQUENCE: 8
catttgtgcc tatgatctat ttccggat                           28

<210> SEQ ID NO 9
<211> LENGTH: 75
<212> TYPE: DNA
<213> ORGANISM: Artificial Sequence
<220> FEATURE:
<223> OTHER INFORMATION: Aptamer

<400> SEQUENCE: 9
atacgagctt gttcaatagt gttgaatagt gccttttgt cttatttta tttctccctg      60 atagtaagag caatc                                         75

<210> SEQ ID NO 10
<211> LENGTH: 40
<212> TYPE: DNA
<213> ORGANISM: Artificial Sequence
<220> FEATURE:
<223> OTHER INFORMATION: Aptamer

<400> SEQUENCE: 10
gtgttgaata gtgcctttt gtcttatttt tatttctccc              40

<210> SEQ ID NO 11
<211> LENGTH: 75
<212> TYPE: DNA
<213> ORGANISM: Artificial Sequence
<220> FEATURE:
<223> OTHER INFORMATION: Aptamer

<400> SEQUENCE: 11
atacgagctt gttcaataca tattcctgtc tcttttgtga tttgccatcc ttttttttctg   60 atagtaagag caatc                                         75

<210> SEQ ID NO 12
<211> LENGTH: 40
<212> TYPE: DNA
<213> ORGANISM: Artificial Sequence
<220> FEATURE:
<223> OTHER INFORMATION: Aptamer

<400> SEQUENCE: 12
catattcctg tctcttttgt gatttgccat cctttttttc              40

<210> SEQ ID NO 13

```
<211> LENGTH: 75
<212> TYPE: DNA
<213> ORGANISM: Artificial Sequence
<220> FEATURE:
<223> OTHER INFORMATION: Aptamer

<400> SEQUENCE: 13
atacgagctt gttcaatatg tgcatgtttt tttgtttgat catcactttc cctttacttg    60
atagtaagag caatc                                                    75

<210> SEQ ID NO 14
<211> LENGTH: 40
<212> TYPE: DNA
<213> ORGANISM: Artificial Sequence
<220> FEATURE:
<223> OTHER INFORMATION: Aptamer

<400> SEQUENCE: 14
tgtgcatgtt ttttgtttg atcatcactt tccctttact                           40

<210> SEQ ID NO 15
<211> LENGTH: 27
<212> TYPE: DNA
<213> ORGANISM: Artificial Sequence
<220> FEATURE:
<223> OTHER INFORMATION: Aptamer

<400> SEQUENCE: 15
caatatgtgc atgttttttt gtttgat                                        27

<210> SEQ ID NO 16
<211> LENGTH: 75
<212> TYPE: DNA
<213> ORGANISM: Artificial Sequence
<220> FEATURE:
<223> OTHER INFORMATION: Aptamer

<400> SEQUENCE: 16
atacgagctt gttcaatacg aagggatgcc gtttgggccc aagttcggca tagtgtggtg    60
atagtaagag caatc                                                    75

<210> SEQ ID NO 17
<211> LENGTH: 40
<212> TYPE: DNA
<213> ORGANISM: Artificial Sequence
<220> FEATURE:
<223> OTHER INFORMATION: Aptamer

<400> SEQUENCE: 17
cgaagggatg ccgtttgggc ccaagttcgg catagtgtgg                          40

<210> SEQ ID NO 18
<211> LENGTH: 35
<212> TYPE: DNA
<213> ORGANISM: Artificial Sequence
<220> FEATURE:
<223> OTHER INFORMATION: Aptamer

<400> SEQUENCE: 18
aagggatgcc gtttgggccc aagttcggca tagtg                               35

<210> SEQ ID NO 19
<211> LENGTH: 38
<212> TYPE: DNA
<213> ORGANISM: Artificial Sequence
```

```
<220> FEATURE:
<223> OTHER INFORMATION: Aptamer

<400> SEQUENCE: 19
gggatgccgt ttgggcccaa gttcggcata gtgtggtg                                    38

<210> SEQ ID NO 20
<211> LENGTH: 75
<212> TYPE: DNA
<213> ORGANISM: Artificial Sequence
<220> FEATURE:
<223> OTHER INFORMATION: Aptamer

<400> SEQUENCE: 20
atacgagctt gttcaatacc gtacggcggc ggtcaggggc caaagtgagt gtggctggtg            60
atagtaagag caatc                                                             75

<210> SEQ ID NO 21
<211> LENGTH: 40
<212> TYPE: DNA
<213> ORGANISM: Artificial Sequence
<220> FEATURE:
<223> OTHER INFORMATION: Aptamer

<400> SEQUENCE: 21
ccgtacggcg gcggtcaggg gccaaagtga gtgtggctgg                                  40

<210> SEQ ID NO 22
<211> LENGTH: 28
<212> TYPE: DNA
<213> ORGANISM: Artificial Sequence
<220> FEATURE:
<223> OTHER INFORMATION: Aptamer

<400> SEQUENCE: 22
ggtcaggggc caaagtgagt gtggctgg                                               28

<210> SEQ ID NO 23
<211> LENGTH: 75
<212> TYPE: DNA
<213> ORGANISM: Artificial Sequence
<220> FEATURE:
<223> OTHER INFORMATION: Aptamer

<400> SEQUENCE: 23
atacgagctt gttcaatacc acctgctgtt gtaacttgtg gaatgtgggt ccccttcgtg            60
atagtaagag caatc                                                             75

<210> SEQ ID NO 24
<211> LENGTH: 40
<212> TYPE: DNA
<213> ORGANISM: Artificial Sequence
<220> FEATURE:
<223> OTHER INFORMATION: Aptamer

<400> SEQUENCE: 24
ccacctgctg ttgtaacttg tggaatgtgg gtccccttcg                                  40

<210> SEQ ID NO 25
<211> LENGTH: 75
<212> TYPE: DNA
<213> ORGANISM: Artificial Sequence
<220> FEATURE:
<223> OTHER INFORMATION: Aptamer
```

<400> SEQUENCE: 25
atacgagctt gttcaatacg aagggatgcc gtttgggccc caagttcggc atagtgtgtg    60
atagtaagag caatc                                                    75

<210> SEQ ID NO 26
<211> LENGTH: 40
<212> TYPE: DNA
<213> ORGANISM: Artificial Sequence
<220> FEATURE:
<223> OTHER INFORMATION: Aptamer

<400> SEQUENCE: 26
cgaagggatg ccgtttgggc cccaagttcg gcatagtgtg                          40

<210> SEQ ID NO 27
<211> LENGTH: 75
<212> TYPE: DNA
<213> ORGANISM: Artificial Sequence
<220> FEATURE:
<223> OTHER INFORMATION: Aptamer

<400> SEQUENCE: 27
atacgagctt gttcaatacc gtacggcggc ggtcaggggc caaagtgagt gtggctggtg    60
atagtaagag caatc                                                    75

<210> SEQ ID NO 28
<211> LENGTH: 40
<212> TYPE: DNA
<213> ORGANISM: Artificial Sequence
<220> FEATURE:
<223> OTHER INFORMATION: Aptamer

<400> SEQUENCE: 28
ccgtacggcg gcggtcaggg gccaaagtga gtgtggctgg                          40

<210> SEQ ID NO 29
<211> LENGTH: 76
<212> TYPE: DNA
<213> ORGANISM: Artificial Sequence
<220> FEATURE:
<223> OTHER INFORMATION: Aptamer

<400> SEQUENCE: 29
atacgagctt gttcaatacc gtacggcggc gcctcagggg ccaaagtgag tgtggctggt    60
gatagtaaga gcaatc                                                   76

<210> SEQ ID NO 30
<211> LENGTH: 41
<212> TYPE: DNA
<213> ORGANISM: Artificial Sequence
<220> FEATURE:
<223> OTHER INFORMATION: Aptamer

<400> SEQUENCE: 30
ccgtacggcg gcgcctcagg ggccaaagtg agtgtggctg g                        41

<210> SEQ ID NO 31
<211> LENGTH: 75
<212> TYPE: DNA
<213> ORGANISM: Artificial Sequence
<220> FEATURE:
<223> OTHER INFORMATION: Aptamer

<400> SEQUENCE: 31
atacgagctt gttcaatatt catctcaaat taaaaagttg agaagtccat tcttcacatg    60
atagtaagag caatc                                                    75

<210> SEQ ID NO 32
<211> LENGTH: 40
<212> TYPE: DNA
<213> ORGANISM: Artificial Sequence
<220> FEATURE:
<223> OTHER INFORMATION: Aptamer

<400> SEQUENCE: 32
ttcatctcaa attaaaaagt tgagaagtcc attcttcaca                          40

<210> SEQ ID NO 33
<211> LENGTH: 75
<212> TYPE: DNA
<213> ORGANISM: Artificial Sequence
<220> FEATURE:
<223> OTHER INFORMATION: Aptamer

<400> SEQUENCE: 33
atacgagctt gttcaatatc gccggcgccg gcctagtctc aaaaagggca ctcccctgtg    60
atagtaagag caatc                                                    75

<210> SEQ ID NO 34
<211> LENGTH: 40
<212> TYPE: DNA
<213> ORGANISM: Artificial Sequence
<220> FEATURE:
<223> OTHER INFORMATION: Aptamer

<400> SEQUENCE: 34
tcgccggcgc cggcctagtc tcaaaaaggg cactcccctg                          40

<210> SEQ ID NO 35
<211> LENGTH: 19
<212> TYPE: DNA
<213> ORGANISM: Artificial Sequence
<220> FEATURE:
<223> OTHER INFORMATION: Aptamer

<400> SEQUENCE: 35
aagggcactc ccctgtgat                                                19

<210> SEQ ID NO 36
<211> LENGTH: 75
<212> TYPE: DNA
<213> ORGANISM: Artificial Sequence
<220> FEATURE:
<223> OTHER INFORMATION: Aptamer

<400> SEQUENCE: 36
atacgagctt gttcaatata tacgtgtgta tgtggctttg tatatacatc tgtggggtg     60 atagtaagag caatc                                                    75

<210> SEQ ID NO 37
<211> LENGTH: 40
<212> TYPE: DNA
<213> ORGANISM: Artificial Sequence
<220> FEATURE:
<223> OTHER INFORMATION: Aptamer

<400> SEQUENCE: 37
tatacgtgtg tatgtggctt tgtatataca tctgtggggg        40

<210> SEQ ID NO 38
<211> LENGTH: 75
<212> TYPE: DNA
<213> ORGANISM: Artificial Sequence
<220> FEATURE:
<223> OTHER INFORMATION: Aptamer

<400> SEQUENCE: 38
atacgagctt gttcaatatg tactttcgtg ttttgggttt tcgtttgttc tgtagtgctg        60
atagtaagag caatc        75

<210> SEQ ID NO 39
<211> LENGTH: 40
<212> TYPE: DNA
<213> ORGANISM: Artificial Sequence
<220> FEATURE:
<223> OTHER INFORMATION: Aptamer

<400> SEQUENCE: 39
tgtactttcg tgttttgggt tttcgtttgt tctgtagtgc        40

<210> SEQ ID NO 40
<211> LENGTH: 75
<212> TYPE: DNA
<213> ORGANISM: Artificial Sequence
<220> FEATURE:
<223> OTHER INFORMATION: Aptamer

<400> SEQUENCE: 40
atacgagctt gttcaatacg ttcggttgta aacttgagtc atgagcccgc ttccccggtg        60
atagtaagag caatc        75

<210> SEQ ID NO 41
<211> LENGTH: 40
<212> TYPE: DNA
<213> ORGANISM: Artificial Sequence
<220> FEATURE:
<223> OTHER INFORMATION: Aptamer

<400> SEQUENCE: 41
cgttcggttg taaacttgag tcatgagccc gcttccccgg        40

<210> SEQ ID NO 42
<211> LENGTH: 18
<212> TYPE: DNA
<213> ORGANISM: Artificial Sequence
<220> FEATURE:
<223> OTHER INFORMATION: Aptamer

<400> SEQUENCE: 42
tcatgagccc gcttcccc        18

<210> SEQ ID NO 43
<211> LENGTH: 75
<212> TYPE: DNA
<213> ORGANISM: Artificial Sequence
<220> FEATURE:
<223> OTHER INFORMATION: Aptamer

<400> SEQUENCE: 43
atacgagctt gttcaatagg aaatcacgat taggtcctcc gtctgtgtgc ggttgtggtg        60
atagtaagag caatc        75

<210> SEQ ID NO 44
<211> LENGTH: 40
<212> TYPE: DNA
<213> ORGANISM: Artificial Sequence
<220> FEATURE:
<223> OTHER INFORMATION: Aptamer

<400> SEQUENCE: 44
ggaaatcacg attaggtcct ccgtctgtgt gcggttgtgg                                  40

<210> SEQ ID NO 45
<211> LENGTH: 75
<212> TYPE: DNA
<213> ORGANISM: Artificial Sequence
<220> FEATURE:
<223> OTHER INFORMATION: Aptamer

<400> SEQUENCE: 45
atacgagctt gttcaatatc cacacgtaac aatcatcggc aataactagt tcacgtggtg           60
atagtaagag caatc                                                             75

<210> SEQ ID NO 46
<211> LENGTH: 40
<212> TYPE: DNA
<213> ORGANISM: Artificial Sequence
<220> FEATURE:
<223> OTHER INFORMATION: Aptamer

<400> SEQUENCE: 46
tccacacgta acaatcatcg gcaataacta gttcacgtgg                                  40

<210> SEQ ID NO 47
<211> LENGTH: 75
<212> TYPE: DNA
<213> ORGANISM: Artificial Sequence
<220> FEATURE:
<223> OTHER INFORMATION: Aptamer

<400> SEQUENCE: 47
atacgagctt gttcaatagt gttgtcggac tgggattagg tgggcatcag cctggctgtg           60
atagtaagag caatc                                                             75

<210> SEQ ID NO 48
<211> LENGTH: 40
<212> TYPE: DNA
<213> ORGANISM: Artificial Sequence
<220> FEATURE:
<223> OTHER INFORMATION: Aptamer

<400> SEQUENCE: 48
gtgttgtcgg actgggatta ggtgggcatc agcctggctg                                  40

<210> SEQ ID NO 49
<211> LENGTH: 75
<212> TYPE: DNA
<213> ORGANISM: Artificial Sequence
<220> FEATURE:
<223> OTHER INFORMATION: Aptamer

<400> SEQUENCE: 49
atacgagctt gttcaatatt tgttctttat gtgatgttcg agtttgttgg tgttgttttg           60
atagtaagag caatc                                                             75

```
<210> SEQ ID NO 50
<211> LENGTH: 40
<212> TYPE: DNA
<213> ORGANISM: Artificial Sequence
<220> FEATURE:
<223> OTHER INFORMATION: Aptamer

<400> SEQUENCE: 50
tttgttcttt atgtgatgtt cgagtttgtt ggtgttgttt                            40

<210> SEQ ID NO 51
<211> LENGTH: 75
<212> TYPE: DNA
<213> ORGANISM: Artificial Sequence
<220> FEATURE:
<223> OTHER INFORMATION: Aptamer

<400> SEQUENCE: 51
atacgagctt gttcaatatg aattttattt tttgttggtt ttaggatatt ttggtttgtg      60
atagtaagag caatc                                                       75

<210> SEQ ID NO 52
<211> LENGTH: 40
<212> TYPE: DNA
<213> ORGANISM: Artificial Sequence
<220> FEATURE:
<223> OTHER INFORMATION: Aptamer

<400> SEQUENCE: 52
tgaattttat tttttgttgg ttttaggata ttttggtttg                            40

<210> SEQ ID NO 53
<211> LENGTH: 75
<212> TYPE: DNA
<213> ORGANISM: Artificial Sequence
<220> FEATURE:
<223> OTHER INFORMATION: Aptamer

<400> SEQUENCE: 53
atacgagctt gttcaataca gttcatttca ccctgagagt gggctaagtt gggcatagtg      60
atagtaagag caatc                                                       75

<210> SEQ ID NO 54
<211> LENGTH: 40
<212> TYPE: DNA
<213> ORGANISM: Artificial Sequence
<220> FEATURE:
<223> OTHER INFORMATION: Aptamer

<400> SEQUENCE: 54
cagttcattt caccctgaga gtgggctaag ttgggcatag                            40

<210> SEQ ID NO 55
<211> LENGTH: 29
<212> TYPE: DNA
<213> ORGANISM: Artificial Sequence
<220> FEATURE:
<223> OTHER INFORMATION: Aptamer

<400> SEQUENCE: 55
tacagttcat ttcaccctga gagtgggct                                        29

<210> SEQ ID NO 56
<211> LENGTH: 75
```

<212> TYPE: DNA
<213> ORGANISM: Artificial Sequence
<220> FEATURE:
<223> OTHER INFORMATION: Aptamer

<400> SEQUENCE: 56
atacgagctt gttcaatacc gtacggcggc ggtcaggggc caaagtgagt gtggctggtg    60
atagtaagag caatc    75

<210> SEQ ID NO 57
<211> LENGTH: 40
<212> TYPE: DNA
<213> ORGANISM: Artificial Sequence
<220> FEATURE:
<223> OTHER INFORMATION: Aptamer

<400> SEQUENCE: 57
ccgtacggcg gcggtcaggg gccaaagtga gtgtggctgg    40

<210> SEQ ID NO 58
<211> LENGTH: 75
<212> TYPE: DNA
<213> ORGANISM: Artificial Sequence
<220> FEATURE:
<223> OTHER INFORMATION: Aptamer

<400> SEQUENCE: 58
atacgagctt gttcaatagg cgagatggtg gagcaggtat gccgttggcg ggtcggggtg    60
atagtaagag caatc    75

<210> SEQ ID NO 59
<211> LENGTH: 40
<212> TYPE: DNA
<213> ORGANISM: Artificial Sequence
<220> FEATURE:
<223> OTHER INFORMATION: Aptamer

<400> SEQUENCE: 59
ggcgagatgg tggagcaggt atgccgttgg cgggtcgggg    40

<210> SEQ ID NO 60
<211> LENGTH: 75
<212> TYPE: DNA
<213> ORGANISM: Artificial Sequence
<220> FEATURE:
<223> OTHER INFORMATION: Aptamer

<400> SEQUENCE: 60
atacgagctt gttcaatacc cgggagttgt caccacataa gtgtatgttg aattttggtg    60
atagtaagag caatc    75

<210> SEQ ID NO 61
<211> LENGTH: 40
<212> TYPE: DNA
<213> ORGANISM: Artificial Sequence
<220> FEATURE:
<223> OTHER INFORMATION: Aptamer

<400> SEQUENCE: 61
cccgggagtt gtcaccacat aagtgtatgt tgaattttgg    40

<210> SEQ ID NO 62
<211> LENGTH: 75
<212> TYPE: DNA

```
<213> ORGANISM: Artificial Sequence
<220> FEATURE:
<223> OTHER INFORMATION: Aptamer

<400> SEQUENCE: 62
atacgagctt gttcaatacg ggtgtggtgt acggcgttga tgttttggtg gaccgtggtg    60
atagtaagag caatc                                                    75

<210> SEQ ID NO 63
<211> LENGTH: 40
<212> TYPE: DNA
<213> ORGANISM: Artificial Sequence
<220> FEATURE:
<223> OTHER INFORMATION: Aptamer

<400> SEQUENCE: 63
cgggtgtggt gtacggcgtt gatgttttgg tggaccgtgg                          40

<210> SEQ ID NO 64
<211> LENGTH: 75
<212> TYPE: DNA
<213> ORGANISM: Artificial Sequence
<220> FEATURE:
<223> OTHER INFORMATION: Aptamer

<400> SEQUENCE: 64
atacgagctt gttcaatagg aagtcacgat taggtcctcc gtctgtgtgc ggttgtggtg    60
atagtaagag caatc                                                    75

<210> SEQ ID NO 65
<211> LENGTH: 40
<212> TYPE: DNA
<213> ORGANISM: Artificial Sequence
<220> FEATURE:
<223> OTHER INFORMATION: Aptamer

<400> SEQUENCE: 65
ggaagtcacg attaggtcct ccgtctgtgt gcggttgtgg                          40

<210> SEQ ID NO 66
<211> LENGTH: 75
<212> TYPE: DNA
<213> ORGANISM: Artificial Sequence
<220> FEATURE:
<223> OTHER INFORMATION: Aptamer

<400> SEQUENCE: 66
atacgagctt gttcaataaa cccactgaca cgaaaaaccg ccgacgctcg agccgccatg    60
atagtaagag caatc                                                    75

<210> SEQ ID NO 67
<211> LENGTH: 40
<212> TYPE: DNA
<213> ORGANISM: Artificial Sequence
<220> FEATURE:
<223> OTHER INFORMATION: Aptamer

<400> SEQUENCE: 67
aacccactga cacgaaaaac cgccgacgct cgagccgcca                          40

<210> SEQ ID NO 68
<211> LENGTH: 75
<212> TYPE: DNA
<213> ORGANISM: Artificial Sequence
```

```
<220> FEATURE:
<223> OTHER INFORMATION: Aptamer

<400> SEQUENCE: 68
atacgagctt gttcaataca gttcatttca ccctgagagt gggctaagtt gggcatagtg        60
atagtaagag caatc                                                        75

<210> SEQ ID NO 69
<211> LENGTH: 40
<212> TYPE: DNA
<213> ORGANISM: Artificial Sequence
<220> FEATURE:
<223> OTHER INFORMATION: Aptamer

<400> SEQUENCE: 69
cagttcattt caccctgaga gtgggctaag ttgggcatag                              40

<210> SEQ ID NO 70
<211> LENGTH: 75
<212> TYPE: DNA
<213> ORGANISM: Artificial Sequence
<220> FEATURE:
<223> OTHER INFORMATION: Aptamer

<400> SEQUENCE: 70
atacgagctt gttcaatacg aagggatgcc gtttgggccc aagttcggca tagtgtggtg        60
atagtaagag caatc                                                        75

<210> SEQ ID NO 71
<211> LENGTH: 40
<212> TYPE: DNA
<213> ORGANISM: Artificial Sequence
<220> FEATURE:
<223> OTHER INFORMATION: Aptamer

<400> SEQUENCE: 71
cgaagggatg ccgtttgggc ccaagttcgg catagtgtgg                              40

<210> SEQ ID NO 72
<211> LENGTH: 75
<212> TYPE: DNA
<213> ORGANISM: Artificial Sequence
<220> FEATURE:
<223> OTHER INFORMATION: Aptamer

<400> SEQUENCE: 72
atacgagctt gttcaatacg aagggatgcc gtttgcgccc aagttcggca tagtgtggtg        60
atagtaagag caatc                                                        75

<210> SEQ ID NO 73
<211> LENGTH: 40
<212> TYPE: DNA
<213> ORGANISM: Artificial Sequence
<220> FEATURE:
<223> OTHER INFORMATION: Aptamer

<400> SEQUENCE: 73
cgaagggatg ccgtttgcgc ccaagttcgg catagtgtgg                              40

<210> SEQ ID NO 74
<211> LENGTH: 75
<212> TYPE: DNA
<213> ORGANISM: Artificial Sequence
<220> FEATURE:
```

<223> OTHER INFORMATION: Aptamer

<400> SEQUENCE: 74
atacgagctt gttcaatagg aaccaagcct tgttatcaaa tagcgggagg ccggctcctg    60
atagtaagag caatc    75

<210> SEQ ID NO 75
<211> LENGTH: 40
<212> TYPE: DNA
<213> ORGANISM: Artificial Sequence
<220> FEATURE:
<223> OTHER INFORMATION: Aptamer

<400> SEQUENCE: 75
ggaaccaagc cttgttatca aatagcggga ggccggctcc    40

<210> SEQ ID NO 76
<211> LENGTH: 75
<212> TYPE: DNA
<213> ORGANISM: Artificial Sequence
<220> FEATURE:
<223> OTHER INFORMATION: Aptamer

<400> SEQUENCE: 76
atacgagctt gttcaatacc gtgcggcggc ggtcaggggc caaagtgagt gtggctggtg    60
atagtaagag caatc    75

<210> SEQ ID NO 77
<211> LENGTH: 40
<212> TYPE: DNA
<213> ORGANISM: Artificial Sequence
<220> FEATURE:
<223> OTHER INFORMATION: Aptamer

<400> SEQUENCE: 77
ccgtgcggcg gcggtcaggg gccaaagtga gtgtggctgg    40

<210> SEQ ID NO 78
<211> LENGTH: 75
<212> TYPE: DNA
<213> ORGANISM: Artificial Sequence
<220> FEATURE:
<223> OTHER INFORMATION: Aptamer

<400> SEQUENCE: 78
atacgagctt gttcaatacg ggtgtggtgt acggcgttga tgttttggtg gaccgtggtg    60
atagtaagag caatc    75

<210> SEQ ID NO 79
<211> LENGTH: 40
<212> TYPE: DNA
<213> ORGANISM: Artificial Sequence
<220> FEATURE:
<223> OTHER INFORMATION: Aptamer

<400> SEQUENCE: 79
cgggtgtggt gtacggcgtt gatgttttgg tggaccgtgg    40

<210> SEQ ID NO 80
<211> LENGTH: 75
<212> TYPE: DNA
<213> ORGANISM: Artificial Sequence
<220> FEATURE:
<223> OTHER INFORMATION: Aptamer

<400> SEQUENCE: 80
atacgagctt gttcaatacg aagggatgcc gttcgggccc aagttcggca tagtgtggtg    60
atagtaagag caatc                                                    75

<210> SEQ ID NO 81
<211> LENGTH: 40
<212> TYPE: DNA
<213> ORGANISM: Artificial Sequence
<220> FEATURE:
<223> OTHER INFORMATION: Aptamer

<400> SEQUENCE: 81
cgaagggatg ccgttcgggc ccaagttcgg catagtgtgg                          40

<210> SEQ ID NO 82
<211> LENGTH: 75
<212> TYPE: DNA
<213> ORGANISM: Artificial Sequence
<220> FEATURE:
<223> OTHER INFORMATION: Aptamer

<400> SEQUENCE: 82
atacgagctt gttcaatacc gacgtaaaac atcttggccc gctggtcggc ccatctcgtg    60
atagtaagag caatc                                                    75

<210> SEQ ID NO 83
<211> LENGTH: 40
<212> TYPE: DNA
<213> ORGANISM: Artificial Sequence
<220> FEATURE:
<223> OTHER INFORMATION: Aptamer

<400> SEQUENCE: 83
ccgacgtaaa acatcttggc ccgctggtcg gcccatctcg                          40

<210> SEQ ID NO 84
<211> LENGTH: 75
<212> TYPE: DNA
<213> ORGANISM: Artificial Sequence
<220> FEATURE:
<223> OTHER INFORMATION: Aptamer

<400> SEQUENCE: 84
atacgagctt gttcaataat tatattgtca tgatgccccc atcgtccttc ccaatgcgtg    60
atagtaagag caatc                                                    75

<210> SEQ ID NO 85
<211> LENGTH: 40
<212> TYPE: DNA
<213> ORGANISM: Artificial Sequence
<220> FEATURE:
<223> OTHER INFORMATION: Aptamer

<400> SEQUENCE: 85
attatattgt catgatgccc ccatcgtcct tcccaatgcg                          40

<210> SEQ ID NO 86
<211> LENGTH: 75
<212> TYPE: DNA
<213> ORGANISM: Artificial Sequence
<220> FEATURE:
<223> OTHER INFORMATION: Aptamer

<400> SEQUENCE: 86
atacgagctt gttcaatacc cccccatagc agccaagctt ttaaccgacc tgggatattg    60
atagtaagag caatc                                                    75

<210> SEQ ID NO 87
<211> LENGTH: 40
<212> TYPE: DNA
<213> ORGANISM: Artificial Sequence
<220> FEATURE:
<223> OTHER INFORMATION: Aptamer

<400> SEQUENCE: 87
cccccccata gcagccaagc ttttaaccga cctgggatat                          40

<210> SEQ ID NO 88
<211> LENGTH: 75
<212> TYPE: DNA
<213> ORGANISM: Artificial Sequence
<220> FEATURE:
<223> OTHER INFORMATION: Aptamer

<400> SEQUENCE: 88
atacgagctt gttcaatatc ccctccatgt tttgcaagga ccctctgga taggcgcgtg     60 atagtaagag caatc                                                    75

<210> SEQ ID NO 89
<211> LENGTH: 40
<212> TYPE: DNA
<213> ORGANISM: Artificial Sequence
<220> FEATURE:
<223> OTHER INFORMATION: Aptamer

<400> SEQUENCE: 89 tccctccat gttttgcaag gatccctctg gataggcgcg                           40

<210> SEQ ID NO 90
<211> LENGTH: 74
<212> TYPE: DNA
<213> ORGANISM: Artificial Sequence
<220> FEATURE:
<223> OTHER INFORMATION: Aptamer

<400> SEQUENCE: 90
atacgagctt gttcaatacc gtacggcggc ggtaggggaa aaagtgagtg tggctggtga    60
tagtaagagc aatc                                                     74

<210> SEQ ID NO 91
<211> LENGTH: 39
<212> TYPE: DNA
<213> ORGANISM: Artificial Sequence
<220> FEATURE:
<223> OTHER INFORMATION: Aptamer

<400> SEQUENCE: 91
ccgtacggcg gcggtagggg aaaaagtgag tgtggctgg                           39

<210> SEQ ID NO 92
<211> LENGTH: 75
<212> TYPE: DNA
<213> ORGANISM: Artificial Sequence
<220> FEATURE:
<223> OTHER INFORMATION: Aptamer

<400> SEQUENCE: 92
atacgagctt gttcaatacg gagccattta gtctacccga tcctcaggat accgaagctg    60
atagtaagag caatc    75

<210> SEQ ID NO 93
<211> LENGTH: 40
<212> TYPE: DNA
<213> ORGANISM: Artificial Sequence
<220> FEATURE:
<223> OTHER INFORMATION: Aptamer

<400> SEQUENCE: 93
cggagccatt tagtctaccc gatcctcagg ataccgaagc    40

<210> SEQ ID NO 94
<211> LENGTH: 75
<212> TYPE: DNA
<213> ORGANISM: Artificial Sequence
<220> FEATURE:
<223> OTHER INFORMATION: Aptamer

<400> SEQUENCE: 94
atacgagctt gttcaatact gcaacagcgg tcccgggtgg gtggtatgca catcgacgtg    60
atagtaagag caatc    75

<210> SEQ ID NO 95
<211> LENGTH: 40
<212> TYPE: DNA
<213> ORGANISM: Artificial Sequence
<220> FEATURE:
<223> OTHER INFORMATION: Aptamer

<400> SEQUENCE: 95
ctgcaacagc ggtcccgggt gggtggtatg cacatcgacg    40

<210> SEQ ID NO 96
<211> LENGTH: 75
<212> TYPE: DNA
<213> ORGANISM: Artificial Sequence
<220> FEATURE:
<223> OTHER INFORMATION: Aptamer

<400> SEQUENCE: 96
atacgagctt gttcaatacc tgatggactt taaaaccttt gacgttcttt tggcttcgtg    60
atagtaagag caatc    75

<210> SEQ ID NO 97
<211> LENGTH: 40
<212> TYPE: DNA
<213> ORGANISM: Artificial Sequence
<220> FEATURE:
<223> OTHER INFORMATION: Aptamer

<400> SEQUENCE: 97
cctgatggac tttaaaacct tgacgttct tttggcttcg    40

<210> SEQ ID NO 98
<211> LENGTH: 75
<212> TYPE: DNA
<213> ORGANISM: Artificial Sequence
<220> FEATURE:
<223> OTHER INFORMATION: Aptamer

<400> SEQUENCE: 98

```
atacgagctt gttcaatacc gtacggcggc agtcagggc  caaagtgagt gtggctggtg    60
atagtaagag caatc                                                     75
```

<210> SEQ ID NO 99
<211> LENGTH: 40
<212> TYPE: DNA
<213> ORGANISM: Artificial Sequence
<220> FEATURE:
<223> OTHER INFORMATION: Aptamer

<400> SEQUENCE: 99

```
ccgtacggcg gcagtcaggg gccaaagtga gtgtggctgg                          40
```

<210> SEQ ID NO 100
<211> LENGTH: 75
<212> TYPE: DNA
<213> ORGANISM: Artificial Sequence
<220> FEATURE:
<223> OTHER INFORMATION: Aptamer

<400> SEQUENCE: 100

```
atacgagctt gttcaatatt cggtggtggt agtcctctgt tcgattggtg tcgtgggttg    60
atagtaagag caatc                                                     75
```

<210> SEQ ID NO 101
<211> LENGTH: 40
<212> TYPE: DNA
<213> ORGANISM: Artificial Sequence
<220> FEATURE:
<223> OTHER INFORMATION: Aptamer

<400> SEQUENCE: 101

```
ttcggtggtg gtagtcctct gttcgattgg tgtcgtgggt                          40
```

<210> SEQ ID NO 102
<211> LENGTH: 75
<212> TYPE: DNA
<213> ORGANISM: Artificial Sequence
<220> FEATURE:
<223> OTHER INFORMATION: Aptamer

<400> SEQUENCE: 102

```
atacgagctt gttcaatacc gtacggcggc ggtcagggtc caaagtgagt gtggctggtg    60
atagtaagag caatc                                                     75
```

<210> SEQ ID NO 103
<211> LENGTH: 40
<212> TYPE: DNA
<213> ORGANISM: Artificial Sequence
<220> FEATURE:
<223> OTHER INFORMATION: Aptamer

<400> SEQUENCE: 103

```
ccgtacggcg gcggtcaggg tccaaagtga gtgtggctgg                          40
```

<210> SEQ ID NO 104
<211> LENGTH: 75
<212> TYPE: DNA
<213> ORGANISM: Artificial Sequence
<220> FEATURE:
<223> OTHER INFORMATION: Aptamer

<400> SEQUENCE: 104

```
atacgagctt gttcaatagg ctccccgagt tacaaataag cgcggtccaa cgtcttcgtg    60
```
atagtaagag caatc                                                        75

<210> SEQ ID NO 105
<211> LENGTH: 40
<212> TYPE: DNA
<213> ORGANISM: Artificial Sequence
<220> FEATURE:
<223> OTHER INFORMATION: Aptamer

<400> SEQUENCE: 105
ggctccccga gttacaaata agcgcggtcc aacgtcttcg                              40

<210> SEQ ID NO 106
<211> LENGTH: 75
<212> TYPE: DNA
<213> ORGANISM: Artificial Sequence
<220> FEATURE:
<223> OTHER INFORMATION: Aptamer

<400> SEQUENCE: 106
atacgagctt gttcaataat agcatatcct aaccggccac ccccatgcgt atcccttctg        60
atagtaagag caatc                                                        75

<210> SEQ ID NO 107
<211> LENGTH: 40
<212> TYPE: DNA
<213> ORGANISM: Artificial Sequence
<220> FEATURE:
<223> OTHER INFORMATION: Aptamer

<400> SEQUENCE: 107
atagcatatc ctaaccggcc accccatgc gtatcccttc                               40

<210> SEQ ID NO 108
<211> LENGTH: 75
<212> TYPE: DNA
<213> ORGANISM: Artificial Sequence
<220> FEATURE:
<223> OTHER INFORMATION: Aptamer

<400> SEQUENCE: 108
atacgagctt gttcaatacg ttcggctgta aacttgagtc atgagcccgc ttccccggtg        60
atagtaagag caatc                                                        75

<210> SEQ ID NO 109
<211> LENGTH: 40
<212> TYPE: DNA
<213> ORGANISM: Artificial Sequence
<220> FEATURE:
<223> OTHER INFORMATION: Aptamer

<400> SEQUENCE: 109
cgttcggctg taaacttgag tcatgagccc gcttccccgg                              40

<210> SEQ ID NO 110
<211> LENGTH: 75
<212> TYPE: DNA
<213> ORGANISM: Artificial Sequence
<220> FEATURE:
<223> OTHER INFORMATION: Aptamer

<400> SEQUENCE: 110
atacgagctt gttcaatacc gtacggcggc ggtcaggggc caaagtgagt gtggctggtg        60
atagtaagag caatc                                                          75

<210> SEQ ID NO 111
<211> LENGTH: 40
<212> TYPE: DNA
<213> ORGANISM: Artificial Sequence
<220> FEATURE:
<223> OTHER INFORMATION: Aptamer

<400> SEQUENCE: 111
ccgtacggcg gcggtcaggg gccaaagtga gtgtggctgg                                40

<210> SEQ ID NO 112
<211> LENGTH: 75
<212> TYPE: DNA
<213> ORGANISM: Artificial Sequence
<220> FEATURE:
<223> OTHER INFORMATION: Aptamer

<400> SEQUENCE: 112
atacgagctt gttcaataac gctgttacaa tggcaatatg actcttccgg aaggtgtatg         60
atagtaagag caatc                                                          75

<210> SEQ ID NO 113
<211> LENGTH: 40
<212> TYPE: DNA
<213> ORGANISM: Artificial Sequence
<220> FEATURE:
<223> OTHER INFORMATION: Aptamer

<400> SEQUENCE: 113
acgctgttac aatggcaata tgactcttcc ggaaggtgta                                40

<210> SEQ ID NO 114
<211> LENGTH: 75
<212> TYPE: DNA
<213> ORGANISM: Artificial Sequence
<220> FEATURE:
<223> OTHER INFORMATION: Aptamer

<400> SEQUENCE: 114
atacgagctt gttcaataca taatggcgtc cccctcaagc ttgaacggta cggggtgctg         60
atagtaagag caatc                                                          75

<210> SEQ ID NO 115
<211> LENGTH: 40
<212> TYPE: DNA
<213> ORGANISM: Artificial Sequence
<220> FEATURE:
<223> OTHER INFORMATION: Aptamer

<400> SEQUENCE: 115
cataatggcg tcccctcaa gcttgaacgg tacggggtgc                                 40

<210> SEQ ID NO 116
<211> LENGTH: 75
<212> TYPE: DNA
<213> ORGANISM: Artificial Sequence
<220> FEATURE:
<223> OTHER INFORMATION: Aptamer

<400> SEQUENCE: 116
atacgagctt gttcaataat ccctatcttc actacagtta gtgacaggtg cattgtcttg         60
atagtaagag caatc                                                          75

```
<210> SEQ ID NO 117
<211> LENGTH: 40
<212> TYPE: DNA
<213> ORGANISM: Artificial Sequence
<220> FEATURE:
<223> OTHER INFORMATION: Aptamer

<400> SEQUENCE: 117
atccctatct tcactacagt tagtgacagg tgcattgtct                    40

<210> SEQ ID NO 118
<211> LENGTH: 75
<212> TYPE: DNA
<213> ORGANISM: Artificial Sequence
<220> FEATURE:
<223> OTHER INFORMATION: Aptamer

<400> SEQUENCE: 118
atacgagctt gttcaataac tgtctcccgt atccctcca aacgtccagg ttcgtctttg     60
atagtaagag caatc                                              75

<210> SEQ ID NO 119
<211> LENGTH: 40
<212> TYPE: DNA
<213> ORGANISM: Artificial Sequence
<220> FEATURE:
<223> OTHER INFORMATION: Aptamer

<400> SEQUENCE: 119
actgtctccc gtatcccctc caaacgtcca ggttcgtctt                    40

<210> SEQ ID NO 120
<211> LENGTH: 75
<212> TYPE: DNA
<213> ORGANISM: Artificial Sequence
<220> FEATURE:
<223> OTHER INFORMATION: Aptamer

<400> SEQUENCE: 120
atacgagctt gttcaatatt acaacgttta cttcatcttt aagtctacat gcggctagtg     60
atagtaagag caatc                                              75

<210> SEQ ID NO 121
<211> LENGTH: 40
<212> TYPE: DNA
<213> ORGANISM: Artificial Sequence
<220> FEATURE:
<223> OTHER INFORMATION: Aptamer

<400> SEQUENCE: 121
ttacaacgtt tacttcatct ttaagtctac atgcggctag                    40

<210> SEQ ID NO 122
<211> LENGTH: 75
<212> TYPE: DNA
<213> ORGANISM: Artificial Sequence
<220> FEATURE:
<223> OTHER INFORMATION: Aptamer

<400> SEQUENCE: 122
atacgagctt gttcaatagc cctttacacc attcatgccg ctcttatcgg tagtcgcgtg     60
atagtaagag caatc                                              75
```

```
<210> SEQ ID NO 123
<211> LENGTH: 40
<212> TYPE: DNA
<213> ORGANISM: Artificial Sequence
<220> FEATURE:
<223> OTHER INFORMATION: Aptamer

<400> SEQUENCE: 123
gccctttaca ccattcatgc cgctcttatc ggtagtcgcg                           40

<210> SEQ ID NO 124
<211> LENGTH: 75
<212> TYPE: DNA
<213> ORGANISM: Artificial Sequence
<220> FEATURE:
<223> OTHER INFORMATION: Aptamer

<400> SEQUENCE: 124
atacgagctt gttcaataca tattttcgta tcctacaacg tttaattgta cggcggattg     60
atagtaagag caatc                                                     75

<210> SEQ ID NO 125
<211> LENGTH: 40
<212> TYPE: DNA
<213> ORGANISM: Artificial Sequence
<220> FEATURE:
<223> OTHER INFORMATION: Aptamer

<400> SEQUENCE: 125
catattttcg tatcctacaa cgtttaattg tacggcggat                           40

<210> SEQ ID NO 126
<211> LENGTH: 75
<212> TYPE: DNA
<213> ORGANISM: Artificial Sequence
<220> FEATURE:
<223> OTHER INFORMATION: Aptamer

<400> SEQUENCE: 126
atacgagctt gttcaatagc gtttagcgtt caattcatcc cgctatctgg ctgtatcgtg     60
atagtaagag caatc                                                     75

<210> SEQ ID NO 127
<211> LENGTH: 40
<212> TYPE: DNA
<213> ORGANISM: Artificial Sequence
<220> FEATURE:
<223> OTHER INFORMATION: Aptamer

<400> SEQUENCE: 127
gcgtttagcg ttcaattcat cccgctatct ggctgtatcg                           40

<210> SEQ ID NO 128
<211> LENGTH: 75
<212> TYPE: DNA
<213> ORGANISM: Artificial Sequence
<220> FEATURE:
<223> OTHER INFORMATION: Aptamer

<400> SEQUENCE: 128
atacgagctt gttcaatatg cgcagaacat tctccgtatg aaggttttcg atacgggatg     60
atagtaagag caatc                                                     75
```

```
<210> SEQ ID NO 129
<211> LENGTH: 40
<212> TYPE: DNA
<213> ORGANISM: Artificial Sequence
<220> FEATURE:
<223> OTHER INFORMATION: Aptamer

<400> SEQUENCE: 129
tgcgcagaac attctccgta tgaaggtttt cgatacggga                                40

<210> SEQ ID NO 130
<211> LENGTH: 75
<212> TYPE: DNA
<213> ORGANISM: Artificial Sequence
<220> FEATURE:
<223> OTHER INFORMATION: Aptamer

<400> SEQUENCE: 130
atacgagctt gttcaatagc aacaaggcga gtgttggcgg ttcggttgtg tggggtggtg          60
atagtaagag caatc                                                          75

<210> SEQ ID NO 131
<211> LENGTH: 40
<212> TYPE: DNA
<213> ORGANISM: Artificial Sequence
<220> FEATURE:
<223> OTHER INFORMATION: Aptamer

<400> SEQUENCE: 131
gcaacaaggc gagtgttggc ggttcggttg tgtggggtgg                                40

<210> SEQ ID NO 132
<211> LENGTH: 75
<212> TYPE: DNA
<213> ORGANISM: Artificial Sequence
<220> FEATURE:
<223> OTHER INFORMATION: Aptamer

<400> SEQUENCE: 132
atacgagctt gttcaataga gttgatagag tattttaacc gggctgtcgt gttggttctg          60
atagtaagag caatc                                                          75

<210> SEQ ID NO 133
<211> LENGTH: 40
<212> TYPE: DNA
<213> ORGANISM: Artificial Sequence
<220> FEATURE:
<223> OTHER INFORMATION: Aptamer

<400> SEQUENCE: 133
gagttgatag agtattttaa ccgggctgtc gtgttggttc                                40

<210> SEQ ID NO 134
<211> LENGTH: 75
<212> TYPE: DNA
<213> ORGANISM: Artificial Sequence
<220> FEATURE:
<223> OTHER INFORMATION: Aptamer

<400> SEQUENCE: 134
atacgagctt gttcaatagc aacaaggcga gtgttggtgg ttcggttgtg tggggtggtg          60
atagtaagag caatc                                                          75

<210> SEQ ID NO 135
```

```
<211> LENGTH: 40
<212> TYPE: DNA
<213> ORGANISM: Artificial Sequence
<220> FEATURE:
<223> OTHER INFORMATION: Aptamer

<400> SEQUENCE: 135
gcaacaaggc gagtgttggt ggttcggttg tgtggggtgg                    40

<210> SEQ ID NO 136
<211> LENGTH: 75
<212> TYPE: DNA
<213> ORGANISM: Artificial Sequence
<220> FEATURE:
<223> OTHER INFORMATION: Aptamer

<400> SEQUENCE: 136
atacgagctt gttcaatact ttatcattat attgatatcc gctagttaat ccgtgagctg    60
atagtaagag caatc                                               75

<210> SEQ ID NO 137
<211> LENGTH: 40
<212> TYPE: DNA
<213> ORGANISM: Artificial Sequence
<220> FEATURE:
<223> OTHER INFORMATION: Aptamer

<400> SEQUENCE: 137
ctttatcatt atattgatat ccgctagtta atccgtgagc                    40

<210> SEQ ID NO 138
<211> LENGTH: 75
<212> TYPE: DNA
<213> ORGANISM: Artificial Sequence
<220> FEATURE:
<223> OTHER INFORMATION: Aptamer

<400> SEQUENCE: 138
atacgagctt gttcaatatc tcattacccc tacctcaccc cccctgttta acgacccgtg    60
atagtaagag caatc                                               75

<210> SEQ ID NO 139
<211> LENGTH: 40
<212> TYPE: DNA
<213> ORGANISM: Artificial Sequence
<220> FEATURE:
<223> OTHER INFORMATION: Aptamer

<400> SEQUENCE: 139
tctcattacc cctacctcac cccccctgtt taacgacccg                    40

<210> SEQ ID NO 140
<211> LENGTH: 75
<212> TYPE: DNA
<213> ORGANISM: Artificial Sequence
<220> FEATURE:
<223> OTHER INFORMATION: Aptamer

<400> SEQUENCE: 140
atacgagctt gttcaatacc cattccgctc ttaggcggtc tcccatttat ctccgtggtg    60
atagtaagag caatc                                               75

<210> SEQ ID NO 141
<211> LENGTH: 40
```

```
<212> TYPE: DNA
<213> ORGANISM: Artificial Sequence
<220> FEATURE:
<223> OTHER INFORMATION: Aptamer

<400> SEQUENCE: 141
cccattccgc tcttaggcgg tctcccattt atctccgtgg                              40

<210> SEQ ID NO 142
<211> LENGTH: 75
<212> TYPE: DNA
<213> ORGANISM: Artificial Sequence
<220> FEATURE:
<223> OTHER INFORMATION: Aptamer

<400> SEQUENCE: 142
atacgagctt gttcaataga ttgggaattg cacctttacc ttgatggtcg ttgtgttgtg        60
atagtaagag caatc                                                         75

<210> SEQ ID NO 143
<211> LENGTH: 40
<212> TYPE: DNA
<213> ORGANISM: Artificial Sequence
<220> FEATURE:
<223> OTHER INFORMATION: Aptamer

<400> SEQUENCE: 143
gattgggaat tgcaccttta ccttgatggt cgttgtgttg                              40

<210> SEQ ID NO 144
<211> LENGTH: 75
<212> TYPE: DNA
<213> ORGANISM: Artificial Sequence
<220> FEATURE:
<223> OTHER INFORMATION: Aptamer

<400> SEQUENCE: 144
atacgagctt gttcaataca atgtgcaccg ggagacctat tccgcccacc agatcctatg        60
atagtaagag caatc                                                         75

<210> SEQ ID NO 145
<211> LENGTH: 40
<212> TYPE: DNA
<213> ORGANISM: Artificial Sequence
<220> FEATURE:
<223> OTHER INFORMATION: Aptamer

<400> SEQUENCE: 145
caatgtgcac cgggagacct attccgccca ccagatccta                              40

<210> SEQ ID NO 146
<211> LENGTH: 75
<212> TYPE: DNA
<213> ORGANISM: Artificial Sequence
<220> FEATURE:
<223> OTHER INFORMATION: Aptamer

<400> SEQUENCE: 146
atacgagctt gttcaatagg cgagatggtg gagcaggtat gccgttggcg ggtcggggtg        60
atagtaagag caatc                                                         75

<210> SEQ ID NO 147
<211> LENGTH: 40
<212> TYPE: DNA
```

```
<213> ORGANISM: Artificial Sequence
<220> FEATURE:
<223> OTHER INFORMATION: Aptamer

<400> SEQUENCE: 147
ggcgagatgg tggagcaggt atgccgttgg cgggtcgggg                              40
```

APTAMER BIOSENSORS USEFUL FOR DETECTING HORMONES, HORMONE MIMICS, AND METABOLITES THEREOF

CROSS-REFERENCE TO RELATED APPLICATIONS AND INCORPORATION BY REFERENCE

This application is a U.S. national phase pursuant to 35 U.S.C. § 371 of International Patent Application No. PCT/ 162016/054839, filed Aug. 11, 2016, which claims priority to U.S. Provisional Patent Application No. 62/204,577, filed Aug. 13, 2015, the disclosures of which are all herein incorporated by reference in their entireties.

This application contains, as a separate part of disclosure, a Sequence Listing in computer-readable form (filename: 52779_Seqlisting.txt; Size: XXX bytes; created February X, 2018), which is incorporated by reference in its entirety.

FIELD OF THE INVENTION

This present invention relates generally to polynucleotides and salts thereof, uses of the polynucleotides and salts thereof, e.g., for detecting a target molecule, such as a hormone, hormone mimic, or metabolite thereof, in a sample. In some embodiments, the polynucleotide or salt thereof forms a nanoparticle complex with an agent.

BACKGROUND OF THE INVENTION

There is an on-going need for methods for rapidly detecting and quantifying the presence of target molecules, for example, as part of environmental testing. For example, target biological molecules such as endocrine-disrupting compounds and hormones are often found as contaminants in the environment. Such contaminants can be found in waterways, soils, biological samples, of both plant and animals, as environmental pollutants from residential, agricultural, commercial and/or industrial applications.

In some cases, these molecules, together with their metabolites and/or synthetically modified variants pose a threat to the health of human, domestic-animal and wildlife populations by mimicking the activity of endogenous hormones, such as estrogens. These molecules may act by blocking, mimicking, stimulating or inhibiting the production and function of natural hormones. The compounds or their residues that mimic these endogenous steroidal hormones, and their metabolites, are typically lipid-soluble and thus, have the ability to bio-accumulate in living systems of mammals and marine species. Evidence of this has been identified in human blood plasma, breast milk, fetal tissues and biological fluids (Allmyr et al., Anal. Chem., 78: 6542-6546, 2006; Hileman, Chemical and Engineering News, 85: 31-33, 2007; Van-Pelt et al. Endocrinology, 140: 478-483, 2001; Skakkebaek et al., Human Reproduction 16: 972-978, 2001; Vandenberg et al., Endocrine Reviews, 33(3): 2012).

More conventional methodologies and techniques that are often used for the detection of small compounds include high performance liquid chromatography (HPLC) or gas chromatography coupled with mass spectrometry (GCMS). Although these techniques can be useful for this purpose, the accompanying analyses can be complicated to perform and can take a long period of time to complete. Furthermore, sample concentration is often required for standard chromatographic techniques and cannot be carried out in situ (Campbell, C. G., et al., 2006, *Chemosphere*, 65, 1265-80). Consequently, these techniques often cannot be performed on site, often require specialised equipment and trained operators, and often do not provide for a rapid assessment of the sample.

Accordingly, there is therefore a need for compositions and methods for the detection of target molecules, such as hormones, hormone mimics, metabolites of hormones and metabolites of hormone mimics, such as in the area of environmental and contaminant testing as in human veterinary medicine, and that can be provided by colorimetric assays which can provide visual indication of the presence of target molecules.

SUMMARY OF THE INVENTION

The present invention relates to methods and compositions useful for detecting a target molecule, such as a hormone, hormone mimic, or metabolite thereof, in a sample.

The present invention provides a polynucleotide or salt thereof comprising a sequence that has at least 70% sequence identity to the sequence of SEQ ID NO: 1-15, 20-128 or 129. The present invention also provides herein a polynucleotide or salt thereof consisting essentially, or consisting of the sequence of SEQ ID NO: 1-15, 17, 19-128 or 129. The present invention also provides an aptamer comprising, consisting essentially of or consisting of a polynucleotide of the invention, a functional fragment thereof, or a salt of either. The present invention also provides herein polynucleotide-agent complexes comprising (i) a polynucleotide disclosed herein, or functional fragment thereof, or a salt thereof, and (ii) an agent. Methods for detecting a target molecule in a sample comprising: (i) contacting a sample with a polynucleotide disclosed herein, or functional fragment thereof or a salt thereof, and (ii) measuring a change in a property of the sample, wherein the change in the property indicates the presence of the target molecule are also provide by the invention. The invention also provides herein methods for detecting a target molecule in a sample, comprising: (i) contacting a sample with a polynucleotide-agent complex disclosed herein, and (ii) measuring a change in a property of the sample, wherein a change in the property is indicative of the presence of the target molecule.

DETAILED DESCRIPTION OF THE INVENTION

Figure 1:
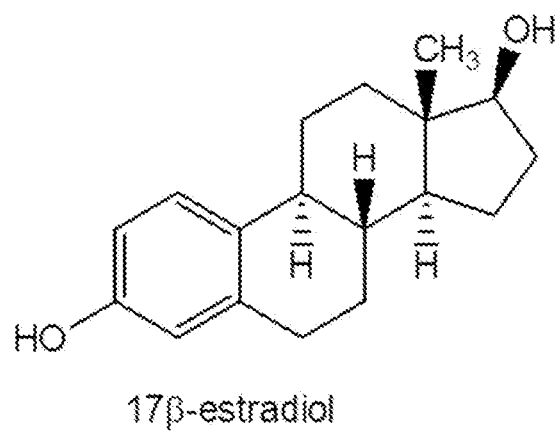
FIG. 1 depicts the structure of 17β-estradiol (E2)

Unless otherwise specified, all technical and scientific terms used herein are to be understood as having the same meanings as is understood by one of ordinary skill in the relevant art to which this disclosure pertains. Examples of definitions of common terms in medicine, molecular biology and biochemistry a can be found in Dictionary of Microbiology and Molecular Biology, Singleton et al, (2d ed. (1994); The Encyclopedia of Molecular Biology, Kendrew et al. (eds.), Blackwell Science Ltd., (1994); Molecular Biology and Biotechnology: a Comprehensive Desk Reference, Robert A. Meyers (ed.), VCH Publishers, Inc., (1995); The Dictionary of Cell & Molecular Biology, 4th Edition. Lackie. J (Ed.), Academic Press Inc. (2007), and The Oxford Dictionary of Biochemistry and Molecular Biology, 2nd edition, Cammack et al. (Eds.), Oxford University Press Inc. (2006).

It is also believed that practice of various embodiments of, encompassed by, and falling within the scope of the present invention can be performed using standard molecular biology and biochemistry protocols and procedures as known in the art, and as described, for example in "Current Protocols in Nucleic Acid Chemistry, Wiley Online Library, Various; Molecular Cloning: A Laboratory Manual, Maniatis et al., Cold Spring Harbor Laboratory Press, (1982); Molecular Cloning: A Laboratory Manual (2 ed.), Sambrook et al., Cold Spring Harbor Laboratory Press, (1989); Guide to Molecular Cloning Techniques Vol. 152, S. L. Berger and A. R. Kimmerl (Eds.), Academic Press Inc., (1987); Protein Synthesis and Ribosome Structure: Translating the Genome. Nierhaus, K and Wilson D (eds.), Wiley-VCH Inc. (2004); Synthetic Peptides: A User's Guide (Advances in Molecular Biology) 2nd edition, Grant G. (Ed.), Oxford University Press (2002); Remington: The Science and Practice of Pharmacy 21st edition, Beringer, P (Ed.), Lippincott Williams & Wilkins, (2005), pp. 2393; and other commonly available reference materials relevant in the art to which this disclosure pertains, and which are all incorporated by reference herein in their entireties.

Definitions

The term "about" when used in connection with a referenced numeric indication means the referenced numeric indication plus or minus up to 10% of that referenced numeric indication. For example, "about 100" means from 90 to 110 and "about six" means from 5.4 to 6.6.

The term "comprising" as used in this specification and claims means "consisting at least in part of". When interpreting statements in this specification, and claims which include the term "comprising", it is to be understood that other features that are additional to the features prefaced by this term in each statement or claim may also be present. Related terms such as "comprise" and "comprised" are to be interpreted in similar manner.

The term "fragment" as used herein is used interchangeably with the term "functional fragment" and means the same thing.

The term "functional fragment" as used herein means a part of a polynucleotide of the invention as disclosed herein that specifically binds to a target molecule.

Polynucleotides

The present invention provides polynucleotides and salts thereof. In some embodiments, a polynucleotide is an oligonucleotide or a single strand of RNA or DNA. In some embodiments, the polynucleotide or functional fragment thereof, or salt of either is an aptamer. The term "aptamer" refers to a polynucleotide or functional fragment thereof, or salt of either that specifically binds a target molecule. The term "specifically binds" is used interchangeably herein with "selectively binds" and means the same thing. As used herein the terms "specifically binds" and "selectively binds" in reference to an aptamer, describe the binding of an aptamer to a target molecule and mean that aptamer binding to the target molecule does not involve the formation of nucleotide base pairs between the aptamer and the target molecule. A person of skill in the art recognizes that it is well-known in the art that the polynucleotide sequence of an aptamer may include base pairs that are not required for specific binding of the aptamer to a given target molecule, and that smaller fragments of an aptamer, even fragments having below 50% sequence identity may still be capable of effectively binding to a target molecule (Alsager, Omar A., et al. "Ultrasensitive Colorimetric Detection of 17β-Estradiol: The Effect of Shortening DNA Aptamer Sequences." *Analytical chemistry* 87.8 (2015): 4201-4209). In some embodiments, an aptamer exerts an inhibitory effect on a target, e.g., by binding of the target, by catalytically altering the target, by reacting with the target in a way which modifies the target or the functional activity of the target, by ionically or covalently attaching to the target or by facilitating the reaction between the target and another molecule. The aptamer can comprise a ribonucleotide, deoxyribonucleotide, or other type of nucleic acid, or two or more different types of nucleic acids. An aptamer can also comprise one or more modified bases, sugars, polyethylene glycol spacers or phosphate backbone units. In some embodiments, the aptamer comprises one or more 2' sugar modifications, such as a 2'-O-alkyl (e.g., 2'-O-methyl or 2'-O-methoxyethyl) or a 2'-fluoro modification.

In some embodiments, an aptamer is a polynucleotide of about 80, about 75, about 70, about 65, about 60, about 55, about 50, about 45, about 40, about 35, about 30, about 25, about 20, about 15 nucleotides in length.

In some embodiments, an aptamer is a polynucleotide of less than 80, less than 75, less than 70, less than 65, less than 60, less than 55, less than 50, less than 45, less than 40, less than 35, less than 30, less than 25, less than 20, less than 15 nucleotides in length.

In some embodiments an aptamer is a polynucleotide of about 70 to 80, is about 60 to 70, is about 50 to 60, is about 40 to 50, is about 30 to 40, is about 20 to 30, is about 10 to 20 nucleotides in length.

In some embodiments an aptamer is a polynucleotide of about 75 to 85, is about 65 to 75, is about 55 to 65, is about 45 to 55, is about 35 to 45, is about 25 to 35, is about 15 to 25 nucleotides in length.

In some embodiments an aptamer is a polynucleotide of 70 to 80, is 60 to 70, is 50 to 60, is 40 to 50, is 30 to 40, is 20 to 30, is 10 to 20 nucleotides in length.

In some embodiments an aptamer is a polynucleotide of 75 to 85, is 65 to 75, is 55 to 65, is 45 to 55, is 35 to 45, is 25 to 35, is 15 to 25 nucleotides in length. In some embodiments the aptamer is about 73 to about 77 or about 74 to about 76 nucleotides in length.

A person of skill in the art will appreciate that an aptamer may be any length polynucleotide that falls within the size parameters set out herein. By way of non-limiting example an aptamer may be about 76, about 61, about 54, about 43, about 29 or about 27 nucleotides in length or may be 77, 62, 55, 44, 28 or 26 nucleotides in length. What is important is that the aptamer specifically binds the target molecule.

In some embodiments an aptamer of the invention is a polynucleotide of about 80, about 75, about 70, about 65, about 60, about 55, about 50, about 45, about 40, about 35, about 30, about 25, about 20, about 15 nucleotides in length that selectively binds a target molecule as described herein.

In some embodiments, an aptamer is a polynucleotide of less than 80, less than 75, less than 70, less than 65, less than 60, less than 55, less than 50, less than 45, less than 40, less than 35, less than 30, less than 25, less than 20, less than 15 nucleotides in length that selectively binds a target molecule as described herein.

In some embodiments an aptamer is a polynucleotide of about 70 to 80, is about 60 to 70, is about 50 to 60, is about 40 to 50, is about 30 to 40, is about 20 to 30, is about 10 to 20 nucleotides in length that selectively binds a target molecule as described herein.

In some embodiments an aptamer is a polynucleotide of about 75 to 85, is about 65 to 75, is about 55 to 65, is about 45 to 55, is about 35 to 45, is about 25 to 35, is about 15 to 25 nucleotides in length that selectively binds a target molecule as described herein.

In some embodiments an aptamer is a polynucleotide of 70 to 80, is 60 to 70, is 50 to 60, is 40 to 50, is 30 to 40, is 20 to 30, is 10 to 20 nucleotides in length that selectively binds a target molecule as described herein.

In some embodiments an aptamer is a polynucleotide of 75 to 85, is 65 to 75, is 55 to 65, is 45 to 55, is 35 to 45, is 25 to 35, is 15 to 25 nucleotides in length that selectively binds a target molecule as described herein.

The term "salt" includes a non-toxic salt of an inorganic or organic acid, including, but not limited to, the following salts: halide (chloride, bromide, iodide, fluoride), acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, hydrochloride, hydrobromide, hydroiodide, 2-hydroxyethanesulfonate, lactate, maleate, malonate, methanesulfonate, nitrate, oxalate, persulfate, phosphate, picrate, pivalate, propionate, p-toluenesulfonate, salicylate, succinate, sulfate, tartrate, thiocyanate, and undecanoate.

The term "salt" also includes a non-toxic salt of an organic or inorganic base, including, but not limited to, the following salts: $Na^+$, $K^+$, $Ca^{2+}$, $Mg^{2+}$, and $Li^+$.

In some embodiments, the target molecule is a small molecule. In some embodiments, the small molecule has a molecular weight (MW) of from about 60 to about 2000 g $mol^{-1}$. In some embodiments, the small molecule has a MW of from about 100 to about 500 g $mol^{-1}$. In some embodiments, the small molecule has a MW of from about 150 to about 350 g $mol^{-1}$. The molecular weight of such small molecules and the calculation of their molecular weight are well known to those of skill in the art.

In some embodiments, a small molecule is a naturally occurring or synthetic hormone, naturally occurring or synthetic hormone mimic, naturally occurring or synthetic phytoestrogen, naturally occurring or synthetic opiate or opioid, or derivative or metabolite thereof (e.g., morphine, oxycodone, hydromorphone, propoxyphene, nicomorphine, dihydrocodeine, diamorphine, papavereturn, codeine, ethylmorphine, phenylpiperidine and derivates thereof, methadone, dextropropoxyphene, buprenorphine, pentazocine, tilidine, tramadol, hydrocodone, meperidine, oxymorphone, alphaprodine, anileridine, dextromoramide, metopone, levorphanol, phenazocine, etoheptazine, propiram, profadol, phenampromide, thiambuten, pholcodeine, codeine, dihydrocodeinon, fentanyl, 3-trans-dimethylamino-4-phenyl-4-trans-carbethoxy-Δ'-cyclohexen, 3-dimethylamino-O-(4-methoxyphenyl-carbamoyl)-propiophenone oxime, (−)β-2'-hydroxy-2,9-dimethyl-5-phenyl-6,7-benzomorphane, (−)2'-hydroxy-2-(3-methyl-2-butenyl)-9-methyl-5-phenyl-6,7-benzomorphane, pirinitramide, (−)α-5,9-diethyl-2'hydroxy-2-methyl-6,7-benzomorphane, ethyl 1-(2-dimethylaminoethyl)-4,5,6,7-tetrahydro-3-methyl-4-oxo-6-phenyl-indol-2-carboxylate, 1-benzoylmethyl-2,3-dimethyl-3-(m-hydroxy-phenyl)-piperidine, N-allyl-7α(1-R-hydroxy-1-methylbutyl)-6,14-endo-ethanotetrahydronororipavine, (−) 2'-hydroxy-2-methyl-6,7-benzomorphane, noracylmethadol, phenoperidine, α-dl-methadol, α-1-methadol, β-dl-acetylmethadol, α-1-acetylmethadol and β-1-acetylmethadol), or a naturally occurring or synthetic organohalide.

Figure 2:
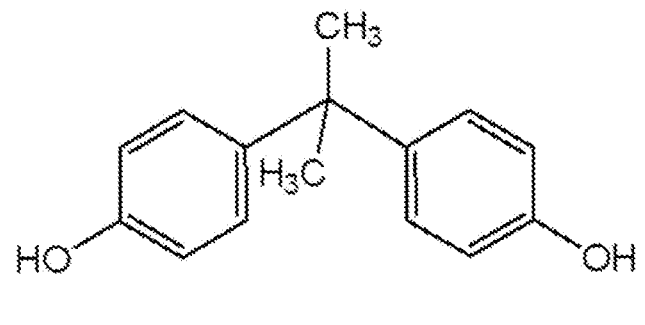
FIG. 2 depicts the structure of bisphenol-A (BPA).
Figure 3:
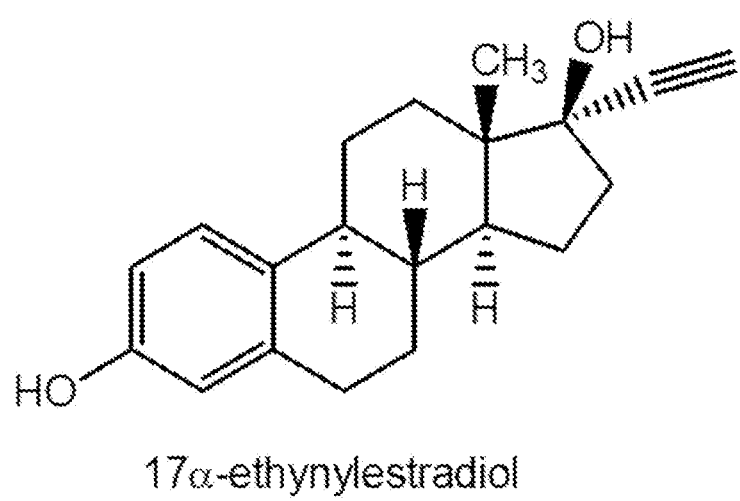
FIG. 3 depicts the structure of 17α-ethynylestradiol.

In some embodiments, the small molecule is an endocrine-disrupting compound, a steroidal or non-steroidal sex hormone, a metabolite or synthetic variant thereof. In some embodiments, the small molecule is an estrogenic compound, for example, a compound that is chemically related to estrogen, a compound that mimics the effect of endogenous estrogen, a compound that exerts an estrogenic effect on a living organism (even though the compound might differ chemically from an estrogenic substance produced endogenously by the endocrine system of an organism), and a compound that is structurally similar to estrogen. Estrogenic compounds may be natural or synthetic, steroidal or non-steroidal, and include a metabolite of such compounds. Examples of estrogenic compounds include estrone (E1), estradiaol (also known as 17β-estradiol or E2; see FIG. 1), estriol (E3), estetrol (E4), a xenoestrogen, a phytoestrogen, and a mycoestrogen. Examples of xenoestrogens include polychlorinated biphenols (also referred to as polychlorobiphenyl or PCBs), bisphenol-A (BPA; FIG. 2), and phthalates. Examples of phytoestrogens include daidzein, formononetin, genistein, bichanin A, coumestrol, 4'-methoxycoumestrol, repensol, and trifoliol. Also included are derivatives of these compounds, such as 17α-ethynylestradiol (FIG. 3).

In some embodiments, the small molecule is androstenedione, androstenediol, testosterone, dihydrotestosterone, pregnenolone, progesterone (P4), 17α-hydroxyprogesterone, Bis (4-hydroxyphenyl) methane (also referred to as bisphenol-F or BPF), cholesterol, adenosine, triclosan, a synthetic steroid (e.g., diethylstilboestrol (DES)), cocaine, heroin, tetrahydrocannabinol (THC), or any derivative or metabolite thereof. In other embodiments, the small molecule is an isoflavone, lignan, coumestan, organohalide (e.g., organochloride), polychlorinated organic compound, alkylphenol, or alkylphenol ethoxylate.

In some embodiments, the small molecule is a hormone or a marker of a condition of disease in a body. In some embodiments, the aptamer selectively binds a hormone and/or metabolite thereof. In some embodiments, the aptamer is useful to determine a particular status of an animal (e.g., a human or non-human animal, such as a domesticated animal (e.g., a cow, sheep, goat, horse, or pig); domesticated pet (e.g., a cat or dog), a wild animal (e.g., a monkey, bird, amphibian, rodent, rabbit, marsupial, or reptile), or an aquatic life form (e.g., fish)), such as the fertility status of the animal. In some embodiments, the aptamer selectively binds a known or an unknown marker of disease, for example a cancer-causing gene, for the detection of cancer or other disease, identification of a patient population that would be favourably disposed to therapy, detection of one or more molecules associated with disease or infection, or to determine a level of one or more specific metabolites associated with a particular condition.

In some embodiments, an aptamer binds 17β-estradiol (E2).

In some embodiments, an aptamer that binds E2 comprises the nucleotide sequence of ATACGAGCTTGTTCAATAGCCTTTAAACTTGTATGGGGATTTAGAATTCTTTCCTCCCT GATAGTAAGAGCAATC (SEQ ID NO: 1) or a fragment thereof. In some embodiments, the fragment comprises the sequence of GCCTTTAAACTTGTATGGGGATTTAGAATTCTTTCCTCCC (SEQ ID NO: 2) or TAGCCTTTAAACTTGTATGGGGATTTA (SEQ ID NO: 3).

In some embodiments, the aptamer that binds E2 comprises the nucleotide sequence of ATACGAGCTTGTTCAATATGTTTCTTTTTCCATGCTAGTTTTTTAGTCTTTTTTACAATG ATAGTAAGAGCAATC (SEQ ID NO: 4) or a fragment thereof. In some embodiments, the fragment comprises the sequence of TGTTTCTTTTTC-CATGCTAGTTTTTTAGTCTTTTTTACAA (SEQ ID NO: 5).

In some embodiments, the aptamer that binds E2 comprises the nucleotide sequence of ATACGAGCTTGT-TCAATATAGTAGAGATTCACATTTGTGCCTATGATC-TATTTCCGGAT GATAGTAAGAGCAATC (SEQ ID NO: 6) or a fragment thereof. In some embodiments, the fragment comprises the sequence of TAGTAGAGATTCA-CATTTGTGCCTATGATCTATTTCCGGA (SEQ ID NO: 7), or CATTTGTGCCTATGATCTATTTCCGGAT (SEQ ID NO: 8).

In some embodiments, the aptamer that binds E2 comprises the nucleotide sequence of ATACGAGCTTGT-TCAATAGTGTTGAATAGTGCCTTTTTGTCTTATTTTT-ATTTCTCCCT GATAGTAAGAGCAATC (SEQ ID NO: 9) or a fragment thereof. In some embodiments, the fragment comprises the sequence of GTGTTGAATAGTGCCTTTTT-GTCTTATTTTTATTTCTCCC (SEQ ID NO: 10).

In some embodiments, the aptamer that binds E2 comprises the nucleotide sequence of ATACGAGCTTGT-TCAATACATATTCCTGTCTCTTTTGTGATTTGCCATC-CTTTTTTTCT GATAGTAAGAGCAATC (SEQ ID NO: 11) or a fragment thereof. In some embodiments, the fragment comprises the sequence of CATATTCCT-GTCTCTTTTGTGATTTGCCATCCTTTTTTTC (SEQ ID NO: 12).

In some embodiments, the aptamer that binds E2 comprises the nucleotide sequence of ATACGAGCTTGT-TCAATATGTGCATGTTTTTTTGTTTGATCAT-CACTTTCCCTTTACTT GATAGTAAGAGCAATC (SEQ ID NO: 13) or a fragment thereof. In some embodiments, the fragment comprises the sequence of TGTGCAT-GTTTTTTTGTTTGATCATCACTTTCCCTTTACT (SEQ ID NO: 14) or CAATATGTGCATGTTTTTTTGTTTGAT (SEQ ID NO: 15).

In some embodiments, the aptamer that binds E2 comprises the nucleotide sequence of ATACGAGCTTGT-TCAATACGAAGGGATGCCGTTTGGGCCCAAGTTCG-GCATAGTGTG GTGATAGTAAGAGCAATC (SEQ ID NO: 16) or a fragment thereof. In some embodiments, the fragment comprises the sequence of CGAAGGGATGC-CGTTTGGGCCCAAGTTCGGCATAGTGTGG (SEQ ID NO: 17), AAGGGATGCCGTTTGGGCCCAAGTTCG-GCATAGTG (SEQ ID NO: 18) or GGGATGC-CGTTTGGGCCCAAGTTCGGCATAGTGTGGTG (SEQ ID NO: 19).

In some embodiments, the aptamer that binds E2 comprises the nucleotide sequence of ATACGAGCTTGT-TCAATACCGTACGGCGGCGGTCAGGGGCCAAAGT-GAGTGTGGCT GGTGATAGTAAGAGCAATC (SEQ ID NO: 20) or a fragment thereof. In some embodiments, the fragment comprises the sequence of CCGTACGGCGGCG-GTCAGGGGCCAAAGTGAGTGTGGCTGG (SEQ ID NO: 21) or GGTCAGGGGCCAAAGTGAGTGTGGCTGG (SEQ ID NO: 22).

In some embodiments, the aptamer that binds E2 comprises the nucleotide sequence of ATACGAGCTTGT-TCAATACCACCTGCTGTTGTAACTTGTGGAAT-GTGGGTCCCCTTC GTGATAGTAAGAGCAATC (SEQ ID NO: 23) or a fragment thereof. In some embodiments, the fragment comprises the sequence of CCACCTGCTGTTG-TAACTTGTGGAATGTGGGTCCCCTTCG (SEQ ID NO: 24).

In some embodiments, the aptamer that binds E2 comprises the nucleotide sequence of ATACGAGCTTGT-TCAATACGAAGGGATGCCGTTTGGGCCCCAAGT-TCGGCATAGTGT GTGATAGTAAGAGCAATC (SEQ ID NO: 25) or a fragment thereof. In some embodiments, the fragment comprises the sequence of CGAAGGGATGC-CGTTTGGGCCCCAAGTTCGGCATAGTGTG (SEQ ID NO: 26).

In some embodiments, an aptamer that binds E2 consists essentially of, or consists of the nucleotide sequence of ATACGAGCTTGTTCAATAGCCTTTAAACTTG-TATGGGGATTTAGAATTCTTTCCTCCCT GATAG-TAAGAGCAATC (SEQ ID NO: 1) or a fragment thereof. In some embodiments, the fragment consists essentially of, or consists of the sequence of GCCTTTAAACTTG-TATGGGGATTTAGAATTCTTTCCTCCC (SEQ ID NO: 2) or TAGCCTTTAAACTTGTATGGGGATTTA (SEQ ID NO: 3).

In some embodiments, the aptamer that binds E2 consists essentially of, or consists of the nucleotide sequence of ATACGAGCTTGTTCAATATGTTTCTTTTTCCAT-GCTAGTTTTTTAGTCTTTTTTACAATG ATAG-TAAGAGCAATC (SEQ ID NO: 4) or a fragment thereof. In some embodiments, the fragment consists essentially of, or consists of the sequence of TGTTTCTTTTTCCAT-GCTAGTTTTTTAGTCTTTTTTACAA (SEQ ID NO: 5).

In some embodiments, the aptamer that binds E2 consists essentially of, or consists of the nucleotide sequence of ATACGAGCTTGTTCAATATAGTAGAGATTCACATTT-GTGCCTATGATCTATTTCCGGAT GATAGTAAGAG-CAATC (SEQ ID NO: 6) or a fragment thereof. In some embodiments, the fragment consists essentially of, or consists of the sequence of TAGTAGAGATTCACATTTGT-GCCTATGATCTATTTCCGGA (SEQ ID NO: 7), or CATTTGTGCCTATGATCTATTTCCGGAT (SEQ ID NO: 8).

In some embodiments, the aptamer that binds E2 consists essentially of, or consists of the nucleotide sequence of ATACGAGCTTGTTCAATAGTGTTGAATAGTGC-CTTTTTGTCTTATTTTTATTTCTCCCT GATAG-TAAGAGCAATC (SEQ ID NO: 9) or a fragment thereof. In some embodiments, the fragment consists essentially of, or consists of the sequence of GTGTTGAATAGTGCCTTTTT-GTCTTATTTTTATTTCTCCC (SEQ ID NO: 10).

In some embodiments, the aptamer that binds E2 consists essentially of, or consists of the nucleotide sequence of ATACGAGCTTGTTCAATACATATTCCTGTCTCTTTT-GTGATTTGCCATCCTTTTTTTCT GATAGTAAGAG-CAATC (SEQ ID NO: 11) or a fragment thereof. In some embodiments, the fragment consists essentially of, or consists of the sequence of CATATTCCTGTCTCTTTTGT-GATTTGCCATCCTTTTTTTC (SEQ ID NO: 12).

In some embodiments, the aptamer that binds E2 consists essentially of, or consists of the nucleotide sequence of ATACGAGCTTGTTCAATATGTGCATGTTTTTTT-GTTTGATCATCACTTTCCCTTTACTT GATAG-TAAGAGCAATC (SEQ ID NO: 13) or a fragment thereof. In some embodiments, the fragment consists essentially of, or consists of the sequence of TGTGCATGTTTTTTT-GTTTGATCATCACTTTCCCTTTACT (SEQ ID NO: 14) or CAATATGTGCATGTTTTTTTGTTTGAT (SEQ ID NO: 15).

In some embodiments, the aptamer that binds E2 consists essentially of, or consists of the nucleotide sequence of ATACGAGCTTGTTCAATACGAAGGGATGC-CGTTTGGGCCCAAGTTCGGCATAGTGTG GTGATAG-TAAGAGCAATC (SEQ ID NO: 16) or a fragment thereof. In some embodiments, the fragment consists essentially of, or consists of the sequence of CGAAGGGATGC-CGTTTGGGCCCAAGTTCGGCATAGTGTGG (SEQ ID NO: 17), AAGGGATGCCGTTTGGGCCCAAGTTCG-GCATAGTG (SEQ ID NO: 18) or GGGATGC-CGTTTGGGCCCAAGTTCGGCATAGTGTGGTG (SEQ ID NO: 19).

In some embodiments, the aptamer that binds E2 consists essentially of, or consists of the nucleotide sequence of ATACGAGCTTGTTCAATACCGTACGGCGGCGGTCA-GGGGCCAAAGTGAGTGTGGCT GGTGATAG-TAAGAGCAATC (SEQ ID NO: 20) or a fragment thereof. In some embodiments, the fragment consists essentially of, or consists of the sequence of CCGTACGGCGGCGGTCA-GGGGCCAAAGTGAGTGTGGCTGG (SEQ ID NO: 21) or GGTCAGGGGCCAAAGTGAGTGTGGCTGG (SEQ ID NO: 22).

In some embodiments, the aptamer that binds E2 consists essentially of, or consists of the nucleotide sequence of ATACGAGCTTGTTCAATACCACCTGCTGTTGTAACT-TGTGGAATGTGGGTCCCCTTC GTGATAGTAAGAG-CAATC (SEQ ID NO: 23) or a fragment thereof. In some embodiments, the fragment consists essentially of, or consists of the sequence of CCACCTGCTGTTGTAACTT-GTGGAATGTGGGTCCCCTTCG (SEQ ID NO: 24).

In some embodiments, the aptamer that binds E2 consists essentially of, or consists of the nucleotide sequence of ATACGAGCTTGTTCAATACGAAGGGATGC-CGTTTGGGCCCCAAGTTCGGCATAGTGT GTGATAG-TAAGAGCAATC (SEQ ID NO: 25) or a fragment thereof. In some embodiments, the fragment consists essentially of, or consists of the sequence of CGAAGGGATGC-CGTTTGGGCCCCAAGTTCGGCATAGTGTG (SEQ ID NO: 26).

In some embodiments, the aptamer binds E2; comprises a sequence that has at least about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity to a sequence selected from SEQ ID NOs: 1-26, or from SEQ ID NOs: 1-15 and 20-26; and in some embodiments, selectively binds E2. In some embodiments, the aptamer consists essentially of, or consists of a sequence selected from SEQ ID NOs: 1-26 or from SEQ ID NOs: 1-15, 17 and 19-26.

In some embodiments, the aptamer binds E2; comprises a sequence that has at least about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity to a sequence selected from SEQ ID NOs: 3, 1-2, 4-15 or 20-26; or SEQ ID NOs: 3, 1-2, 4-15, 17, or 19-26; and in some embodiments, selectively binds E2. In some embodiments, the aptamer consists essentially of, or consists of a sequence selected from SEQ ID NOs: 3, 1-2, 4-15 or 20-26; or SEQ ID NOs: 3, 1-2, 4-15, 17, or 19-26.

In some embodiments the aptamer that binds E2 is a polynucleotide of less than 80 nucleotides in length. In some embodiments the aptamer that binds E2 is less than 30 nucleotides in length.

In some embodiments the aptamer that binds E2 is a polynucleotide of about 25 or about 30 nucleotides in length, or of about 25 to 30 nucleotides in length, or of 25 to 30 nucleotides in length less and comprises or consists essentially of, or consists of SEQ ID NO: 3.

In some embodiments the aptamer that binds E2 is a polynucleotide comprising a sequence that has at least about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity to SEQ ID NO: 3.

In some embodiments the aptamer that binds E2 is a polynucleotide consisting essentially of, or consisting of a sequence that has 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity to SEQ ID NO: 3.

In some embodiments, the aptamer binds androstenedione. In some embodiments, the aptamer that binds androstenedione comprises the nucleotide sequence of ATAC-GAGCTTGTTCAATACCGTACGGCGGCGGTCAGGG-GCCAAAGTGAGTGTGGCT GGTGATAGTAAGAG-CAATC (SEQ ID NO: 27) or a fragment thereof. In some embodiments, the fragment comprises the sequence of CCGTACGGCGGCGGTCAGGGGCCAAAGTGAGT-GTGGCTGG (SEQ ID NO: 28).

In some embodiments, the aptamer that binds androstenedione comprises the nucleotide sequence of ATACGAGCT-TGTTCAATACCGTACGGCGGCGCCTCAGGGGC-CAAAGTGAGTGTGGC TGGTGATAGTAAGAGCAATC (SEQ ID NO: 29) or a fragment thereof. In some embodiments, the fragment comprises the sequence of CCGTACG-GCGGCGCCTCAGGGGCCAAAGTGAGTGTGGCTGG (SEQ ID NO: 30).

In some embodiments, the aptamer that binds androstenedione comprises the nucleotide sequence of ATACGAGCT-TGTTCAATATTCATCTCAAATTAAAAAGTT-GAGAAGTCCATTCTTCACAT GATAGTAAGAGCAATC (SEQ ID NO: 31) or a fragment thereof. In some embodiments, the fragment comprises the sequence of TTCATCTCAAATTAAAAAGTT-GAGAAGTCCATTCTTCACA (SEQ ID NO: 32).

In some embodiments, the aptamer that binds androstenedione comprises the nucleotide sequence of ATACGAGCT-TGTTCAATAGCAACAAGGCGAGTGTTGGCGGT-TCGGTTGTGTGGGGT GGTGATAGTAAGAGCAATC (SEQ ID NO: 130) or a fragment thereof. In some embodiments, the fragment comprises the sequence of GCAACAAGGCGAGTGTTGGCGGTTCGGTTGT-GTGGGGTGG (SEQ ID NO: 131).

In some embodiments, the aptamer that binds androstenedione comprises the nucleotide sequence of ATACGAGCT-TGTTCAATAGAGTTGATAGAGTATTTTAACCGGGCT-GTCGTGTTGGTTC TGATAGTAAGAGCAATC (SEQ ID NO: 132) or a fragment thereof. In some embodiments, the fragment comprises the sequence of GAGTTGATAGAGT-ATTTTAACCGGGCTGTCGTGTTGGTTC (SEQ ID NO: 133).

In some embodiments, the aptamer that binds androstenedione consists essentially of, or consists of the nucleotide sequence of ATACGAGCTTGTTCAATACCGTACGGCG-GCGGTCAGGGGCCAAAGTGAGTGTGGCT GGTGA-TAGTAAGAGCAATC (SEQ ID NO: 27) or a fragment thereof. In some embodiments, the fragment consists essentially of, or consists of the sequence of CCGTACGGCG-GCGGTCAGGGGCCAAAGTGAGTGTGGCTGG (SEQ ID NO: 28).

In some embodiments, the aptamer that binds androstenedione consists essentially of, or consists of the nucleotide sequence of ATACGAGCTTGTTCAATACCGTACGGCG-GCGCCTCAGGGGCCAAAGTGAGTGTGGC TGGT-GATAGTAAGAGCAATC (SEQ ID NO: 29) or a fragment thereof. In some embodiments, the fragment consists essentially of, or consists of the sequence of CCGTACGGCG-GCGCCTCAGGGGCCAAAGTGAGTGTGGCTGG (SEQ ID NO: 30).

In some embodiments, the aptamer that binds androstenedione consists essentially of, or consists of the nucleotide sequence of ATACGAGCTTGTTCAATATTCATCT-CAAATTAAAAAGTTGAGAAGTCCATTCTTCACAT GATAGTAAGAGCAATC (SEQ ID NO: 31) or a fragment thereof. In some embodiments, the fragment consists essentially of, or consists of the sequence of TTCATCTCAAAT-TAAAAAGTTGAGAAGTCCATTCTTCACA (SEQ ID NO: 32).

In some embodiments, the aptamer that binds androstenedione consists essentially of, or consists of the nucleotide sequence of ATACGAGCTTGTTCAATAG-CAACAAGGCGAGTGTTGGCGGTTCGGTTGT-GTGGGGT GGTGATAGTAAGAGCAATC (SEQ ID NO: 130) or a fragment thereof. In some embodiments, the fragment consists essentially of, or consists of the sequence of GCAACAAGGCGAGTGTTGGCGGTTCGGTTGT-GTGGGGTGG (SEQ ID NO: 131).

In some embodiments, the aptamer that binds androstenedione consists essentially of, or consists of the nucleotide sequence of ATACGAGCTTGTTCAATAGAGTTGATA-GAGTATTTTAACCGGGCTGTCGTGTTGGTTC TGA-TAGTAAGAGCAATC (SEQ ID NO: 132) or a fragment thereof. In some embodiments, the fragment consists essentially of, or consists of the sequence of GAGTTGATAGAG-TATTTTAACCGGGCTGTCGTGTTGGTTC (SEQ ID NO: 133).

In some embodiments, the aptamer binds androstenedione comprises a sequence that has at least about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity to a sequence selected from SEQ ID NOs: 27-32 and 130-133; and in some embodiments, selectively binds androstenedione. In some embodiments, the aptamer consists essentially of, or consists of a sequence selected from SEQ ID NOs: 27-32 and 130-133.

In some embodiments, the aptamer binds androstenedione comprises a sequence that has at least about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity to a sequence selected from SEQ ID NOs: 29, 27, 28, 30-32 and 130-133; and in some embodiments, selectively binds androstenedione. In some embodiments, the aptamer consists essentially of, or consists of a sequence selected from SEQ ID NOs: 29, 27, 28, 30-32 and 130-133.

In some embodiments the aptamer that binds androstenedione is a polynucleotide of less than 80 nucleotides in length.

In some embodiments the aptamer that binds androstenedione is a polynucleotide of about 73 or about 77 nucleotides in length, or of about 74 to 76 nucleotides in length, or of 70 to 80 nucleotides in length and comprises or consists essentially of, or consists of SEQ ID NO: 29 or SEQ ID NO: 27.

In some embodiments the aptamer that binds androstenedione is a polynucleotide comprising a sequence that has at least about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity to SEQ ID NOs: 29 or 27.

In some embodiments the aptamer that binds androstenedione is a polynucleotide that consists essentially of, or consists of a sequence that has 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity to SEQ ID NOs: 29 or 27.

In some embodiments, the aptamer binds bisphenol-A (BPA).

In some embodiments, the aptamer that binds BPA comprises the nucleotide sequence of ATACGAGCTTGT-TCAATATCGCCGGCGCCGGCCTAGTCTCAAAAAG-GGCACTCCCCT GTGATAGTAAGAGCAATC (SEQ ID NO: 33) or a fragment thereof. In some embodiments, the fragment comprises the sequence of TCGCCGGCGCCG-GCCTAGTCTCAAAAAGGGCACTCCCCTG (SEQ ID NO: 34) or AAGGGCACTCCCCTGTGAT (SEQ ID NO: 35).

In some embodiments, the aptamer that binds BPA comprises the nucleotide sequence of ATACGAGCTTGT-TCAATATATACGTGTGTATGTGGCTTTGTATATA-CATCTGTGGGGG TGATAGTAAGAGCAATC (SEQ ID NO: 36) or a fragment thereof. In some embodiments, the fragment comprises the sequence of TATACGTGTGTAT-GTGGCTTTGTATATACATCTGTGGGGG (SEQ ID NO: 37).

In some embodiments, the aptamer that binds BPA comprises the nucleotide sequence of ATACGAGCTTGT-TCAATATGTACTTTCGTGTTTTGGGTTTTCGTTTGT-TCTGTAGTGCT GATAGTAAGAGCAATC (SEQ ID NO: 38) or a fragment thereof. In some embodiments, the fragment comprises the sequence of TGTACTTTCGT-GTTTTGGGTTTTCGTTTGTTCTGTAGTGC (SEQ ID NO: 39). In some embodiments, the aptamer that binds BPA comprises the nucleotide sequence of ATACGAGCTTGT-TCAATACGTTCGGTTGTAAACTTGAGTCATGAGC-CCGCTTCCCCG GTGATAGTAAGAGCAATC (SEQ ID NO: 40) or a fragment thereof. In some embodiments, the fragment comprises the sequence of CGTTCGGTTG-TAAACTTGAGTCATGAGCCCGCTTCCCCGG (SEQ ID NO: 41) or TCATGAGCCCGCTTCCCC (SEQ ID NO: 42).

In some embodiments, the aptamer that binds BPA comprises the nucleotide sequence of ATACGAGCTTGT-TCAATAGGAAATCACGATTAGGTCCTCCGTCTGT-GTGCGGTTGTG GTGATAGTAAGAGCAATC (SEQ ID NO: 43) or a fragment thereof. In some embodiments, the fragment comprises the sequence of GGAAATCACGATT-AGGTCCTCCGTCTGTGTGCGGTTGTGG (SEQ ID NO: 44).

In some embodiments, the aptamer that binds BPA comprises the nucleotide sequence of ATACGAGCTTGT-TCAATATCCACACGTAACAATCATCGGCAATAACT-AGTTCACGTGG TGATAGTAAGAGCAATC (SEQ ID NO: 45) or a fragment thereof. In some embodiments, the fragment comprises the sequence of TCCACACG-TAACAATCATCGGCAATAACTAGTTCACGTGG (SEQ ID NO: 46).

In some embodiments, the aptamer that binds BPA comprises the nucleotide sequence of ATACGAGCTTGT-TCAATAGTGTTGTCGGACTGGGATTAG-GTGGGCATCAGCCTGGCT GTGATAGTAAGAGCAATC (SEQ ID NO: 47) or a fragment thereof. In some embodiments, the fragment comprises the sequence of GTGTTGTCGGACTGGGATTAG-GTGGGCATCAGCCTGGCTG (SEQ ID NO: 48).

In some embodiments, the aptamer that binds BPA comprises the nucleotide sequence of ATACGAGCTTGT-TCAATATTTGTTCTTTATGTGATGTTCGAGTTTGT-TGGTGTTGTTTT GATAGTAAGAGCAATC (SEQ ID NO: 49) or a fragment thereof. In some embodiments, the fragment comprises the sequence of TTTGTTCTTTATGT-GATGTTCGAGTTTGTTGGTGTTGTTT (SEQ ID NO: 50). In some embodiments, the aptamer that binds BPA comprises the nucleotide sequence of ATACGAGCTTGT-TCAATATGAATTTTATTTTTTGTTGGTTTTAGGAT-ATTTTGGTTTGTG ATAGTAAGAGCAATC (SEQ ID NO: 51) or a fragment thereof. In some embodiments, the fragment comprises the sequence of TGAATTTTATTTTTT-GTTGGTTTTAGGATATTTTGGTTTG (SEQ ID NO: 52). In some embodiments, the aptamer or salt thereof that binds BPA comprises the nucleotide sequence of ATACGAGCT-TGTTCAATACAGTTCATTTCACCCTGAGAGTGG-GCTAAGTTGGGCATA GTGATAGTAAGAGCAATC (SEQ ID NO: 53) or a fragment thereof. In some embodiments, the fragment comprises the sequence of CAGTTCATTTCACCCTGAGAGTGGGCTAAGT-TGGGCATAG (SEQ ID NO: 54) or TACAGTTCATTTCACCCTGAGAGTGGGCT (SEQ ID NO: 55).

In some embodiments, the aptamer that binds BPA comprises the nucleotide sequence of ATACGAGCTTGT-TCAATACCGTACGGCGGCGGTCAGGGGCCAAAGT-GAGTGTGGCT GGTGATAGTAAGAGCAATC (SEQ ID NO: 56) or a fragment thereof. In some embodiments, the fragment comprises the sequence of CCGTACGGCGGCG-GTCAGGGGCCAAAGTGAGTGTGGCTGG (SEQ ID NO: 57).

In some embodiments, the aptamer that binds BPA comprises the nucleotide sequence of ATACGAGCTTGT-TCAATAGGCGAGATGGTGGAGCAGGTATGCCGTTG-GCGGGTCGG GGTGATAGTAAGAGCAATC (SEQ ID NO: 58) or a fragment thereof. In some embodiments, the fragment comprises the sequence of GGCGAGATGGTG-GAGCAGGTATGCCGTTGGCGGGTCGGG (SEQ ID NO: 59).

In some embodiments, the aptamer that binds BPA comprises the nucleotide sequence of ATACGAGCTTGT-TCAATACCCGGGAGTTGTCACCACATAAGTGTAT-GTTGAATTTTGG TGATAGTAAGAGCAATC (SEQ ID NO: 60) or a fragment thereof. In some embodiments, the fragment comprises the sequence of CCCGGGAGTTGT-CACCACATAAGTGTATGTTGAATTTTGG (SEQ ID NO: 61).

In some embodiments, the aptamer that binds BPA comprises the nucleotide sequence of ATACGAGCTTGT-TCAATACGGGTGTGGTGTACGGCGTTGATGTTTTG-GTGGACCGTG GTGATAGTAAGAGCAATC (SEQ ID NO: 62) or a fragment thereof. In some embodiments, fragment comprises the sequence of CGGGTGTGGTG-TACGGCGTTGATGTTTTGGTGGACCGTGG (SEQ ID NO: 63).

In some embodiments, the aptamer that binds BPA comprises the nucleotide sequence of ATACGAGCTTGT-TCAATAGGAAGTCACGATTAGGTCCTCCGTCTGT-GTGCGGTTGTG GTGATAGTAAGAGCAATC (SEQ ID NO: 64) or a fragment thereof. In some embodiments, the fragment comprises the sequence of GGAAGTCACGATT-AGGTCCTCCGTCTGTGTGCGGTTGTGG (SEQ ID NO: 65).

In some embodiments, the aptamer that binds BPA comprises the nucleotide sequence of ATACGAGCTTGT-TCAATAAACCCACTGACACGAAAAACCGC-CGACGCTCGAGCCGCC ATGATAGTAAGAGCAATC (SEQ ID NO: 66) or a fragment thereof. In some embodiments, the fragment comprises a sequence of AACCCACT-GACACGAAAAACCGCCGACGCTCGAGCCGCCA (SEQ ID NO: 67).

In some embodiments, the aptamer that binds BPA comprises the nucleotide sequence of ATACGAGCTTGT-TCAATACAGTTCATTTCACCCTGAGAGTGGG-CTAAGTTGGGCATA GTGATAGTAAGAGCAATC (SEQ ID NO: 68) or a fragment thereof. In some embodiments, the fragment comprises the sequence of CAGTTCATTTCAC-CCTGAGAGTGGGCTAAGTTGGGCATAG (SEQ ID NO: 69).

In some embodiments, the aptamer that binds BPA comprises the nucleotide sequence of ATACGAGCTTGT-TCAATACGAAGGGATGCCGTTTGGGCCCAAGTTCG-GCATAGTGTG GTGATAGTAAGAGCAATC (SEQ ID NO: 70) or a fragment thereof. In some embodiments, the fragment comprises the sequence of CGAAGGGATGC-CGTTTGGGCCCAAGTTCGGCATAGTGTGG (SEQ ID NO: 71).

In some embodiments, the aptamer that binds BPA comprises the nucleotide sequence of ATACGAGCTTGT-TCAATACGAAGGGATGCCGTTTGCGCCCAAGTTCG-GCATAGTGTG GTGATAGTAAGAGCAATC (SEQ ID NO: 72) or a fragment thereof. In some embodiments, the fragment comprises the sequence of CGAAGGGATGC-CGTTTGCGCCCAAGTTCGGCATAGTGTGG (SEQ ID NO: 73).

In some embodiments, the aptamer that binds BPA comprises the nucleotide sequence of ATACGAGCTTGT-TCAATAGGAACCAAGCCTTGTTAT-CAAATAGCGGGAGGCCGGCTC CTGATAGTAAGAGCAATC (SEQ ID NO: 74) or a fragment thereof. In some embodiments, the fragment comprises the sequence of GGAACCAAGCCTTGTTAT-CAAATAGCGGGAGGCCGGCTCC (SEQ ID NO: 75).

In some embodiments, the aptamer that binds BPA comprises the nucleotide sequence of ATACGAGCTTGT-TCAATAGCAACAAGGCGAGTGTTGGTGGTTCGGTT-GTGTGGGGTG GTGATAGTAAGAGCAATC (SEQ ID NO: 134) or a fragment thereof. In some embodiments, the fragment comprises the sequence of GCAACAAGGC-GAGTGTTGGTGGTTCGGTTGTGTGGGGTGG (SEQ ID NO: 135).

In some embodiments, the aptamer that binds BPA comprises the nucleotide sequence of ATACGAGCTTGT-TCAATACTTTATCATTATATTGATATCCGCTAGT-TAATCCGTGAGCT GATAGTAAGAGCAATC (SEQ ID NO: 136) or a fragment thereof. In some embodiments, the fragment comprises the sequence of CTTTATCATTATAT-TGATATCCGCTAGTTAATCCGTGAGC (SEQ ID NO: 137).

In some embodiments, the aptamer that binds BPA comprises the nucleotide sequence of ATACGAGCTTGT-TCAATATCTCATTACCCCTACCTCACCCCCCTGTT-TAACGACCCG TGATAGTAAGAGCAATC (SEQ ID NO: 138) or a fragment thereof. In some embodiments, the fragment comprises the sequence of TCTCATTAC-CCCTACCTCACCCCCCTGTTTAACGACCCG (SEQ ID NO: 139).

In some embodiments, the aptamer that binds BPA consists essentially of, or consists of the nucleotide sequence of ATACGAGCTTGTTCAATATCGCCGGCGCCGGC-CTAGTCTCAAAAAGGGCACTCCCCT GTGATAG-TAAGAGCAATC (SEQ ID NO: 33) or a fragment thereof. In some embodiments, the fragment consists essentially of, or consists of the sequence of TCGCCGGCGCCGGC-CTAGTCTCAAAAAGGGCACTCCCCTG (SEQ ID NO: 34) or AAGGGCACTCCCCTGTGAT (SEQ ID NO: 35).

In some embodiments, the aptamer that binds BPA consists essentially of, or consists of the nucleotide sequence of ATACGAGCTTGTTCAATATATACGTGTGTATGTG-GCTTTGTATATACATCTGTGGGGG TGATAG-TAAGAGCAATC (SEQ ID NO: 36) or a fragment thereof. In some embodiments, the fragment consists essentially of, or consists of the sequence of TATACGTGTGTATGTG-GCTTTGTATATACATCTGTGGGGG (SEQ ID NO: 37).

In some embodiments, the aptamer that binds BPA consists essentially of, or consists of the nucleotide sequence of ATACGAGCTTGTTCAATATGTACTTTCGTGTTTTG-GGTTTTCGTTTGTTCTGTAGTGCT GATAGTAAGAG-CAATC (SEQ ID NO: 38) or a fragment thereof. In some embodiments, the fragment consists essentially of, or consists of the sequence of TGTACTTTCGT-GTTTTGGGTTTTCGTTTGTTCTGTAGTGC (SEQ ID NO: 39).

In some embodiments, the aptamer that binds BPA consists essentially of, or consists of the nucleotide sequence of ATACGAGCTTGTTCAATACGTTCGGTTGTAAACTT-GAGTCATGAGCCCGCTTCCCCG GTGATAG-TAAGAGCAATC (SEQ ID NO: 40) or a fragment thereof. In some embodiments, the fragment consists essentially of, or consists of the sequence of CGTTCGGTTGTAAACTT-GAGTCATGAGCCCGCTTCCCCGG (SEQ ID NO: 41) or TCATGAGCCCGCTTCCCC (SEQ ID NO: 42).

In some embodiments, the aptamer that binds BPA consists essentially of, or consists of the nucleotide sequence of ATACGAGCTTGTTCAATAGGAAATCACGATTAG-GTCCTCCGTCTGTGTGCGGTTGTG GTGATAG-TAAGAGCAATC (SEQ ID NO: 43) or a fragment thereof. In some embodiments, the fragment consists essentially of, or consists of the sequence of GGAAATCACGATTAG-GTCCTCCGTCTGTGTGCGGTTGTGG (SEQ ID NO: 44).

In some embodiments, the aptamer that binds BPA consists essentially of, or consists of the nucleotide sequence of ATACGAGCTTGTTCAATATCCACACGTAACAAT-CATCGGCAATAACTAGTTCACGTGG TGATAG-TAAGAGCAATC (SEQ ID NO: 45) or a fragment thereof. In some embodiments, the fragment consists essentially of, or consists of the sequence of TCCACACGTAACAAT-CATCGGCAATAACTAGTTCACGTGG (SEQ ID NO: 46).

In some embodiments, the aptamer that binds BPA consists essentially of, or consists of the nucleotide sequence of ATACGAGCTTGTTCAATAGTGTTGTCG-GACTGGGATTAGGTGGGCATCAGCCTGGCT GTGA-TAGTAAGAGCAATC (SEQ ID NO: 47) or a fragment thereof. In some embodiments, the fragment consists essentially of, or consists of the sequence of GTGTTGTCG-GACTGGGATTAGGTGGGCATCAGCCTGGCTG (SEQ ID NO: 48).

In some embodiments, the aptamer that binds BPA consists essentially of, or consists of the nucleotide sequence of ATACGAGCTTGTTCAATATTTGTTCTTTATGTGATGT-TCGAGTTTGTTGGTGTTGTTTT GATAGTAAGAG-CAATC (SEQ ID NO: 49) or a fragment thereof. In some embodiments, the fragment consists essentially of, or consists of the sequence of TTTGTTCTTTATGTGATGTTC-GAGTTTGTTGGTGTTGTTT (SEQ ID NO: 50). In some embodiments, the aptamer that binds BPA consists essentially of, or consists of the nucleotide sequence of ATAC-GAGCTTGTTCAATATGAATTTTATTTTTTGTTGGTTT-TAGGATATTTTGGTTTGTG ATAGTAAGAGCAATC (SEQ ID NO: 51) or a fragment thereof. In some embodiments, the fragment consists essentially of, or consists of the sequence of TGAATTTTATTTTTTGTTGGTTTTAGGAT-ATTTTGGTTTG (SEQ ID NO: 52).

In some embodiments, the aptamer that binds BPA consists essentially of, or consists of the nucleotide sequence of ATACGAGCTTGTTCAATACAGTTCATTTCACCCT-GAGAGTGGGCTAAGTTGGGCATA GTGATAG-TAAGAGCAATC (SEQ ID NO: 53) or a fragment thereof. In some embodiments, the fragment consists essentially of, or consists of the sequence of CAGTTCATTTCACCCT-GAGAGTGGGCTAAGTTGGGCATAG (SEQ ID NO: 54) or TACAGTTCATTTCACCCTGAGAGTGGGCT (SEQ ID NO: 55).

In some embodiments, the aptamer that binds BPA consists essentially of, or consists of the nucleotide sequence of ATACGAGCTTGTTCAATACCGTACGGCGGCGGTCA-GGGGCCAAAGTGAGTGTGGCT GGTGATAG-TAAGAGCAATC (SEQ ID NO: 56) or a fragment thereof. In some embodiments, the fragment consists essentially of, or consists of the sequence of CCGTACGGCGGCGGTCA-GGGGCCAAAGTGAGTGTGGCTGG (SEQ ID NO: 57).

In some embodiments, the aptamer that binds BPA consists essentially of, or consists of the nucleotide sequence of ATACGAGCTTGTTCAATAGGCGAGATGGTGGAGCA-GGTATGCCGTTGGCGGGTCGG GGTGATAG-TAAGAGCAATC (SEQ ID NO: 58) or a fragment thereof. In some embodiments, the fragment consists essentially of, or consists of the sequence of GGCGAGATGGTGGAGCA-GGTATGCCGTTGGCGGGTCGGGG (SEQ ID NO: 59).

In some embodiments, the aptamer that binds BPA consists essentially of, or consists of the nucleotide sequence of ATACGAGCTTGTTCAATACCCGGGAGTTGTCACCA-CATAAGTGTATGTTGAATTTTGG TGATAGTAAGAG-CAATC (SEQ ID NO: 60) or a fragment thereof. In some embodiments, the fragment consists essentially of, or consists of the sequence of CCCGGGAGTTGTCACCA-CATAAGTGTATGTTGAATTTTGG (SEQ ID NO: 61).

In some embodiments, the aptamer that binds BPA consists essentially of, or consists of the nucleotide sequence of ATACGAGCTTGTTCAATACGGGTGTGGTGTACG-GCGTTGATGTTTTGGTGGACCGTG GTGATAG-TAAGAGCAATC (SEQ ID NO: 62) or a fragment thereof. In some embodiments, fragment consists essentially of, or consists of the sequence of CGGGTGTGGTGTACGGCGT-TGATGTTTTGGTGGACCGTGG (SEQ ID NO: 63).

In some embodiments, the aptamer that binds BPA consists essentially of, or consists of the nucleotide sequence of ATACGAGCTTGTTCAATAGGAAGTCACGATTAG-GTCCTCCGTCTGTGTGCGGTTGTG GTGATAG-TAAGAGCAATC (SEQ ID NO: 64) or a fragment thereof. In some embodiments, the fragment consists essentially of, or consists of the sequence of GGAAGTCACGATTAG-GTCCTCCGTCTGTGTGCGGTTGTGG (SEQ ID NO: 65).

In some embodiments, the aptamer that binds BPA consists essentially of, or consists of the nucleotide sequence of ATACGAGCTTGTTCAATAAACCCACTGACAC-GAAAAACCGCCGACGCTCGAGCCGCC ATGATAG-TAAGAGCAATC (SEQ ID NO: 66) or a fragment thereof. In some embodiments, the fragment consists essentially of, or consists of a sequence of AACCCACTGACAC-GAAAAACCGCCGACGCTCGAGCCGCCA (SEQ ID NO: 67).

In some embodiments, the aptamer that binds BPA consists essentially of, or consists of the nucleotide sequence of ATACGAGCTTGTTCAATACAGTTCATTTCACCCT-GAGAGTGGGCTAAGTTGGGCATA GTGATAG-TAAGAGCAATC (SEQ ID NO: 68) or a fragment thereof. In some embodiments, the fragment consists essentially of, or consists of the sequence of CAGTTCATTTCACCCT-GAGAGTGGGCTAAGTTGGGCATAG (SEQ ID NO: 69).

In some embodiments, the aptamer that binds BPA consists essentially of, or consists of the nucleotide sequence of ATACGAGCTTGTTCAATACGAAGGGATGC-CGTTTGGGCCCAAGTTCGGCATAGTGTG GTGATAG-TAAGAGCAATC (SEQ ID NO: 70) or a fragment thereof. In some embodiments, the fragment consists essentially of, or consists of the sequence of CGAAGGGATGC-CGTTTGGGCCCAAGTTCGGCATAGTGTGG (SEQ ID NO: 71).

In some embodiments, the aptamer that binds BPA consists essentially of, or consists of the nucleotide sequence of ATACGAGCTTGTTCAATACGAAGGGATGCCGTTT-GCGCCCAAGTTCGGCATAGTGTG GTGATAG-TAAGAGCAATC (SEQ ID NO: 72) or a fragment thereof. In some embodiments, the fragment consists essentially of, or consists of the sequence of CGAAGGGATGCCGTTT-GCGCCCAAGTTCGGCATAGTGTGG (SEQ ID NO: 73).

In some embodiments, the aptamer that binds BPA consists essentially of, or consists of the nucleotide sequence of ATACGAGCTTGTTCAATAGGAACCAAGCCTTGT-TATCAAATAGCGGGAGGCCGGCTC CTGATAG-TAAGAGCAATC (SEQ ID NO: 74) or a fragment thereof. In some embodiments, the fragment consists essentially of, or consists of the sequence of GGAACCAAGCCTTGT-TATCAAATAGCGGGAGGCCGGCTCC (SEQ ID NO: 75).

In some embodiments, the aptamer that binds BPA consists essentially of, or consists of the nucleotide sequence of ATACGAGCTTGTTCAATAGCAACAAGGCGAGTGT-TGGTGGTTCGGTTGTGTGGGGTG GTGATAG-TAAGAGCAATC (SEQ ID NO: 134) or a fragment thereof. In some embodiments, the fragment consists essentially of, or consists of the sequence of GCAACAAGGCGAGTGT-TGGTGGTTCGGTTGTGTGGGGTGG (SEQ ID NO: 135).

In some embodiments, the aptamer that binds BPA consists essentially of, or consists of the nucleotide sequence of ATACGAGCTTGTTCAATACTTTATCATTATATTGA-TATCCGCTAGTTAATCCGTGAGCT GATAGTAAGAG-CAATC (SEQ ID NO: 136) or a fragment thereof. In some embodiments, the fragment consists essentially of, or consists of the sequence of CTTTATCATTATATTGATATC-CGCTAGTTAATCCGTGAGC (SEQ ID NO: 137).

In some embodiments, the aptamer that binds BPA consists essentially of, or consists of the nucleotide sequence of ATACGAGCTTGTTCAATATCTCATTACCCCTACCT-CACCCCCCCTGTTTAACGACCCG TGATAGTAAGAG-CAATC (SEQ ID NO: 138) or a fragment thereof. In some embodiments, the fragment consists essentially of, or consists of the sequence of TCTCATTACCCCTACCTCAC-CCCCCCTGTTTAACGACCCG (SEQ ID NO: 139).

In some embodiments, the aptamer binds BPA; comprises a sequence that has at least about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity to a sequence selected from SEQ ID NOs: 33-75 and 134-139; and in some embodiments, selectively binds BPA. In some embodiments, the aptamer or salt thereof consists essentially of, or consists of a sequence selected from SEQ ID NOs: 33-75 and 134-139.

In some embodiments, the aptamer binds BPA; comprises a sequence that has at least about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity to a sequence selected from SEQ ID NOs: 53, 55, 56, 33-52, 54, 57-75 and 134-139; and in some embodiments, selectively binds BPA. In some embodiments, the aptamer or salt thereof consists essentially of, or consists of a sequence selected from SEQ ID NOs: 53, 55, 56, 33-52, 54, 57-75 and 134-139.

In some embodiments the aptamer that binds BPA is a polynucleotide of less than 80 nucleotides in length or less than 30 nucleotides in length.

In some embodiments the aptamer that binds BPA is a polynucleotide of about 73 or about 77 nucleotides in length, or of about 74 to 76 nucleotides in length, or of 70 to 80 nucleotides in length and comprises or consists essentially of, or consists of SEQ ID NO: 53 or SEQ ID NO: 56.

In some embodiments the aptamer that binds BPA is a polynucleotide comprising a sequence that has at least about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity to SEQ ID NOs: 53 or 56.

In some embodiments the aptamer that binds BPA is a polynucleotide of about 27 or about nucleotides in length, or is 25 to 30 nucleotides in length, or is 26 to 29 nucleotides in length and comprises or consists essentially of, or consists of SEQ ID NO: 55.

In some embodiments the aptamer that binds BPA is a polynucleotide comprising a sequence that has at least about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity to SEQ ID NOs: 55.

In some embodiments the aptamer that binds BPA is a polynucleotide consisting essentially of, or consisting of a sequence that has at least about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity to SEQ ID NOs: 55.

In some embodiments, the aptamer binds progesterone.

In some embodiments, the aptamer that binds progesterone comprises the nucleotide sequence of ATACGAGCTT-GTTCAATACCGTGCGGCGGCGGTCAGGGGC-CAAAGTGAGTGTGGCT GGTGATAGTAAGAGCAATC (SEQ ID NO: 76) or a fragment thereof. In some embodiments, the fragment comprises the sequence of CCGTGCG-GCGGCGGTCAGGGGCCAAAGTGAGTGTGGCTGG (SEQ ID NO: 77).

In some embodiments, the aptamer that binds progesterone comprises the nucleotide sequence of ATACGAGCTT-GTTCAATACGGGTGTGGTGTACGGCGTTGAT-GTTTTGGTGGACCGTG GTGATAGTAAGAGCAATC (SEQ ID NO: 78) or a fragment thereof. In some embodiments, the fragment comprises the sequence of CGGGT-GTGGTGTACGGCGTTGATGTTTTGGTGGACCGTGG (SEQ ID NO: 79).

In some embodiments, the aptamer that binds progesterone comprises the nucleotide sequence of ATACGAGCTT-GTTCAATACGAAGGGATGCCGTTCGGGCCCAAGT-TCGGCATAGTGTG GTGATAGTAAGAGCAATC (SEQ ID NO: 80) or a fragment thereof. In some embodiments, the fragment comprises the sequence of CGAAGGGATGC-CGTTCGGGCCCAAGTTCGGCATAGTGTGG (SEQ ID NO: 81).

In some embodiments, the aptamer that binds progesterone comprises the nucleotide sequence of ATACGAGCTT-GTTCAATACCGACGTAAAACATCTTGGCCCGCTG-GTCGGCCCATCTC GTGATAGTAAGAGCAATC (SEQ ID NO: 82) or a fragment thereof. In some embodiments, the fragment comprises a sequence of CCGACG-TAAAACATCTTGGCCCGCTGGTCGGCCCATCTCG (SEQ ID NO: 83).

In some embodiments, the aptamer that binds progesterone comprises the nucleotide sequence of ATACGAGCTT-GTTCAATAATTATATTGTCATGATGCCCCCATCGTC-CTTCCCAATGCG TGATAGTAAGAGCAATC (SEQ ID NO: 84) or a fragment thereof. In some embodiments, the fragment comprises the sequence of ATTATATTGTCAT-GATGCCCCCATCGTCCTTCCCAATGCG (SEQ ID NO: 85).

In some embodiments, the aptamer that binds progesterone comprises the nucleotide sequence of ATACGAGCTT-GTTCAATACCCCCCCATAGCAGCCAAGCTTTTAAC-CGACCTGGGATA TTGATAGTAAGAGCAATC (SEQ ID NO: 86) or a fragment thereof. In some embodiments, the fragment comprises the sequence of CCCCCCCATAGCAGCCAAGCTTTTAACCGACCTGGGATAT (SEQ ID NO: 87).

In some embodiments, the aptamer that binds progesterone comprises the nucleotide sequence of ATACGAGCTTGTTCAATATCCCCTCCATGTTTTGCAAGGATCCCTCTGGATAGGCGC GTGATAGTAAGAGCAATC (SEQ ID NO: 88) or a fragment thereof. In some embodiments, the fragment comprises the sequence of TCCCCTCCATGTTTTGCAAGGATCCCTCTGGATAGGCGCG (SEQ ID NO: 89).

In some embodiments, the aptamer that binds progesterone comprises the nucleotide sequence of ATACGAGCTTGTTCAATACCGTACGGCGGCGG-TAGGGGAAAAAGTGAGTGTGGCTG GTGATAGTAAGAGCAATC (SEQ ID NO: 90) or a fragment thereof. In some embodiments, the fragment comprises the sequence of CCGTACGGCGGCGG-TAGGGGAAAAAGTGAGTGTGGCTGG (SEQ ID NO: 91).

In some embodiments, the aptamer that binds progesterone comprises the nucleotide sequence of ATACGAGCTTGTTCAATACGGAGCCATTTAGTCTACCCGATCCTCAGGATACCGAAG CTGATAGTAAGAGCAATC (SEQ ID NO: 92) or a fragment thereof. In some embodiments, the fragment comprises the sequence of CGGAGCCATTTAGTCTACCCGATCCTCAGGATACCGAAGC (SEQ ID NO: 93).

In some embodiments, the aptamer that binds progesterone comprises the nucleotide sequence of ATACGAGCTTGTTCAATACTGCAACAGCGGTCCCGGGTGGGTGGTATGCACATCGA CGTGATAGTAAGAGCAATC (SEQ ID NO: 94) or a fragment thereof. In some embodiments, the fragment comprises the sequence of CTGCAACAGCGGTCCCGGGTGGGTGGTATGCACATCGACG (SEQ ID NO: 95).

In some embodiments, the aptamer that binds progesterone comprises the nucleotide sequence of ATACGAGCTTGTTCAATACCTGATGGACTTTAAAACCTTTGACGTTCTTTTGGCTTCG TGATAGTAAGAGCAATC (SEQ ID NO: 96) or a fragment thereof. In some embodiments, the fragment comprises the sequence of CCTGATGGACTTTAAAACCTTTGACGTTCTTTTGGCTTCG (SEQ ID NO: 97).

In some embodiments, the aptamer that binds progesterone comprises the nucleotide sequence of ATACGAGCTTGTTCAATACCGTACGGCGGCAGTCAGGGGC-CAAAGTGAGTGTGGCT GGTGATAGTAAGAGCAATC (SEQ ID NO: 98) or a fragment thereof. In some embodiments, the fragment comprises the sequence of CCGTACGGCGGCAGTCAGGGGCCAAAGTGAGTGTGGCTGG (SEQ ID NO: 99).

In some embodiments, the aptamer that binds progesterone comprises the nucleotide sequence of ATACGAGCTTGTTCAATATTCGGTGGTGGTAGTCCTCTGTTCGATTGGTGTCGTGGG TTGATAGTAAGAGCAATC (SEQ ID NO: 100) or a fragment thereof. In some embodiments, the fragment comprises the sequence of TTCGGTGGTGG-TAGTCCTCTGTTCGATTGGTGTCGTGGGT (SEQ ID NO: 101).

In some embodiments, the aptamer that binds progesterone comprises the nucleotide sequence of ATACGAGCTTGTTCAATACCGTACGGCGGCGGTCAGGGTC-CAAAGTGAGTGTGGCT GGTGATAGTAAGAGCAATC (SEQ ID NO: 102) or a fragment thereof. In some embodiments, the fragment comprises the sequence of CCGTACGGCGGCGGTCAGGGTCCAAAGTGAGTGTGGCTGG (SEQ ID NO: 103).

In some embodiments, the aptamer that binds progesterone comprises the nucleotide sequence of ATACGAGCTTGTTCAATAGGCTCCCCGAGTTACAAATAAGCGCGGTCCAACGTCTTC GTGATAGTAAGAGCAATC (SEQ ID NO: 104) or a fragment thereof. In some embodiments, the fragment comprises the sequence of GGCTCCCCGAGTTACAAATAAGCGCGGTCCAACGTCTTCG (SEQ ID NO: 105).

In some embodiments, the aptamer that binds progesterone comprises the nucleotide sequence of ATACGAGCTTGTTCAATAATAGCATATCCTAACCGGCCACCCCCATGCGTATCCCTTC TGATAGTAAGAGCAATC (SEQ ID NO: 106) or a fragment thereof. In some embodiments, the fragment comprises the sequence of ATAGCATATCCTAACCGGCCACCCCCATGCGTATCCCTTC (SEQ ID NO: 107).

In some embodiments, the aptamer that binds progesterone comprises the nucleotide sequence of ATACGAGCTTGTTCAATACGTTCGGCTGTAAACTTGAGTCATGAGCCCGCTTCCCCG GTGATAGTAAGAGCAATC (SEQ ID NO: 108) or a fragment thereof. In some embodiments, the fragment comprises a sequence of CGTTCGGCTGTAAACTTGAGTCATGAGCCCGCTTCCCCGG (SEQ ID NO: 109).

In some embodiments, the aptamer that binds progesterone comprises the nucleotide sequence of ATACGAGCTTGTTCAATACCGTACGGCGGCGGTCAGGGGC-CAAAGTGAGTGTGGCT GGTGATAGTAAGAGCAATC (SEQ ID NO: 110) or a fragment thereof. In some embodiments, the fragment comprises the sequence of CCGTACGGCGGCGGTCAGGGGCCAAAGTGAGTGTGGCTGG (SEQ ID NO: 111).

In some embodiments, the aptamer that binds progesterone comprises the nucleotide sequence of ATACGAGCTTGTTCAATACCCATTCCGCTCTTAGGCGGTCTC-CATTTATCTCCGTGG TGATAGTAAGAGCAATC (SEQ ID NO: 140) or a fragment thereof. In some embodiments, the fragment comprises the sequence of CCCATTCCGCTCTTAGGCGGTCTCCCATTTATCTCCGTGG (SEQ ID NO: 141).

In some embodiments, the aptamer that binds progesterone comprises the nucleotide sequence of ATACGAGCTTGTTCAATAGATTGGGAATTGCACCTTTACCTTGATGGTCGTTGTGTTG TGATAGTAAGAGCAATC (SEQ ID NO: 142) or a fragment thereof. In some embodiments, the fragment comprises the sequence of GATTGGGAATTGCACCTTTACCTTGATGGTCGTTGTGTTG (SEQ ID NO: 143).

In some embodiments, the aptamer that binds progesterone comprises the nucleotide sequence of ATACGAGCTTGTTCAATAGGCGAGATGGTGGAGCAGGTATGCCGTTGGCGGGTCGG GGTGATAGTAAGAGCAATC (SEQ ID NO: 146) or a fragment thereof. In some embodiments, the fragment comprises the sequence of GGCGAGATGGTGGAGCAGGTATGCCGTTGGCGGGTCGGGG (SEQ ID NO: 147).

In some embodiments, the aptamer that binds progesterone consists of the nucleotide sequence of ATACGAGCTTGTTCAATACCGTGCGGCGGCGGTCAGGGGC-CAAAGTGAGTGTGGCT GGTGATAGTAAGAGCAATC (SEQ ID NO: 76) or a fragment thereof. In some embodiments, the fragment consists essentially of, or consists of the sequence of CCGTGCGGCGGCGGTCAGGGGC-CAAAGTGAGTGTGGCTGG (SEQ ID NO: 77).

In some embodiments, the aptamer that binds progesterone consists essentially of, or consists of the nucleotide sequence of ATACGAGCTTGTTCAATACGGGTGTGGTGTACGGCGTTGATGTTTTGGTGGACCGTG GTGATAGTAAGAGCAATC (SEQ ID NO: 78) or a fragment thereof. In some embodiments, the fragment consists essentially of, or consists of the sequence of CGGGTGTGGTGTACGGCGTTGATGTTTTGGTGGACCGTGG (SEQ ID NO: 79).

In some embodiments, the aptamer that binds progesterone consists essentially of, or consists of the nucleotide sequence of ATACGAGCTTGTTCAATACGAAGGGATGCCGTTCGGGCCCAAGTTCGGCATAGTGTG GTGATAGTAAGAGCAATC (SEQ ID NO: 80) or a fragment thereof. In some embodiments, the fragment consists essentially of, or consists of the sequence of CGAAGGGATGCCGTTCGGGCCCAAGTTCGGCATAGTGTGG (SEQ ID NO: 81).

In some embodiments, the aptamer that binds progesterone consists essentially of, or consists of the nucleotide sequence of ATACGAGCTTGTTCAATACCGACGTAAAACATCTTGGCCCGCTGGTCGGCCCATCTC GTGATAGTAAGAGCAATC (SEQ ID NO: 82) or a fragment thereof. In some embodiments, the fragment consists essentially of, or consists of a sequence of CCGACGTAAAACATCTTGGCCCGCTGGTCGGCCCATCTCG (SEQ ID NO: 83).

In some embodiments, the aptamer that binds progesterone consists essentially of, or consists of the nucleotide sequence of ATACGAGCTTGTTCAATAATTATATTGTCATGATGCCCCATCGTCCTTCCCAATGCG TGATAGTAAGAGCAATC (SEQ ID NO: 84) or a fragment thereof. In some embodiments, the fragment consists essentially of, or consists of the sequence of ATTATATTGTCATGATGCCCCATCGTCCTTCCCAATGCG (SEQ ID NO: 85).

In some embodiments, the aptamer that binds progesterone consists essentially of, or consists of the nucleotide sequence of ATACGAGCTTGTTCAATACCCCCCCATAGCAGCCAAGCTTTTAACCGACCTGGGATA TTGATAGTAAGAGCAATC (SEQ ID NO: 86) or a fragment thereof. In some embodiments, the fragment consists essentially of, or consists of the sequence of CCCCCCCATAGCAGCCAAGCTTTTAACCGACCTGGGATAT (SEQ ID NO: 87).

In some embodiments, the aptamer that binds progesterone consists essentially of, or consists of the nucleotide sequence of ATACGAGCTTGTTCAATATCCCCTCCATGTTTTGCAAGGATCCCTCTGGATAGGCGC GTGATAGTAAGAGCAATC (SEQ ID NO: 88) or a fragment thereof. In some embodiments, the fragment consists essentially of, or consists of the sequence of TCCCCTCCATGTTTTGCAAGGATCCCTCTGGATAGGCGCG (SEQ ID NO: 89).

In some embodiments, the aptamer that binds progesterone consists essentially of, or consists of the nucleotide sequence of ATACGAGCTTGTTCAATACCGTACGGCGGCGGTAGGGGAAAAAGTGAGTGTGGCTG GTGATAGTAAGAGCAATC (SEQ ID NO: 90) or a fragment thereof. In some embodiments, the fragment consists essentially of, or consists of the sequence of CCGTACGGCGGCGGTAGGGGAAAAAGTGAGTGTGGCTGG (SEQ ID NO: 91).

In some embodiments, the aptamer that binds progesterone consists essentially of, or consists of the nucleotide sequence of ATACGAGCTTGTTCAATACGGAGCCATTTAGTCTACCCGATCCTCAGGATACCGAAG CTGATAGTAAGAGCAATC (SEQ ID NO: 92) or a fragment thereof. In some embodiments, the fragment consists essentially of, or consists of the sequence of CGGAGCCATTTAGTCTACCCGATCCTCAGGATACCGAAGC (SEQ ID NO: 93).

In some embodiments, the aptamer that binds progesterone consists essentially of, or consists of the nucleotide sequence of ATACGAGCTTGTTCAATACTGCAACAGCGGTCCCGGGTGGGTGGTATGCACATCGA CGTGATAGTAAGAGCAATC (SEQ ID NO: 94) or a fragment thereof. In some embodiments, the fragment consists essentially of, or consists of the sequence of CTGCAACAGCGGTCCCGGGTGGGTGGTATGCACATCGACG (SEQ ID NO: 95).

In some embodiments, the aptamer that binds progesterone consists essentially of, or consists of the nucleotide sequence of ATACGAGCTTGTTCAATACCTGATGGACTTTAAAACCTTTGACGTTCTTTTGGCTTCG TGATAGTAAGAGCAATC (SEQ ID NO: 96) or a fragment thereof. In some embodiments, the fragment consists essentially of, or consists of the sequence of CCTGATGGACTTTAAAACCTTTGACGTTCTTTTGGCTTCG (SEQ ID NO: 97).

In some embodiments, the aptamer that binds progesterone consists essentially of, or consists of the nucleotide sequence of ATACGAGCTTGTTCAATACCGTACGGCGGCAGTCAGGGGCCAAAGTGAGTGTGGCT GGTGATAGTAAGAGCAATC (SEQ ID NO: 98) or a fragment thereof. In some embodiments, the fragment consists essentially of, or consists of the sequence of CCGTACGGCGGCAGTCAGGGGCCAAAGTGAGTGTGGCTGG (SEQ ID NO: 99).

In some embodiments, the aptamer that binds progesterone consists essentially of, or consists of the nucleotide sequence of ATACGAGCTTGTTCAATATTCGGTGGTGGTAGTCCTCTGTTCGATTGGTGTCGTGGG TTGATAGTAAGAGCAATC (SEQ ID NO: 100) or a fragment thereof. In some embodiments, the fragment consists essentially of, or consists of the sequence of TTCGGTGGTGGTAGTCCTCTGTTCGATTGGTGTCGTGGGT (SEQ ID NO: 101).

In some embodiments, the aptamer that binds progesterone consists essentially of, or consists of the nucleotide sequence of ATACGAGCTTGTTCAATACCGTACGGCGGCGGTCAGGGTCCAAAGTGAGTGTGGCT GGTGATAGTAAGAGCAATC (SEQ ID NO: 102) or a fragment thereof. In some embodiments, the fragment consists essentially of, or consists of the sequence of CCGTACGGCGGCGGTCAGGGTCCAAAGTGAGTGTGGCTGG (SEQ ID NO: 103).

In some embodiments, the aptamer that binds progesterone consists essentially of, or consists of the nucleotide sequence of ATACGAGCTTGTTCAATAGGCTCCCCGAGTTACAAATAAGCGCGGTCCAACGTCTTC GTGATAGTAAGAGCAATC (SEQ ID NO: 104) or a fragment thereof. In some embodiments, the fragment consists essentially of, or consists of the sequence of GGCTCCCCGAGTTACAAATAAGCGCGGTCCAACGTCTTCG (SEQ ID NO: 105).

In some embodiments, the aptamer that binds progesterone consists essentially of, or consists of the nucleotide sequence of ATACGAGCTTGTTCAATAATAGCATATCCTAACCGGCCACCCCCATGCGTATCCCTTC TGATAGTAAGAGCAATC (SEQ ID NO: 106) or a fragment thereof. In some embodiments, the fragment consists essentially of, or consists of the sequence of ATAGCATATC-CTAACCGGCCACCCCCATGCGTATCCCTTC (SEQ ID NO: 107).

In some embodiments, the aptamer that binds progesterone consists essentially of, or consists of the nucleotide sequence of ATACGAGCTTGTTCAATACGTTCGGCTG-TAAACTTGAGTCATGAGCCCGCTTCCCCG GTGA-TAGTAAGAGCAATC (SEQ ID NO: 108) or a fragment thereof. In some embodiments, the fragment consists essentially of, or consists of a sequence of CGTTCGGCTG-TAAACTTGAGTCATGAGCCCGCTTCCCCGG (SEQ ID NO: 109).

In some embodiments, the aptamer that binds progesterone consists essentially of, or consists of the nucleotide sequence of ATACGAGCTTGTTCAATACCGTACGGCG-GCGGTCAGGGGCCAAAGTGAGTGTGGCT GGTGA-TAGTAAGAGCAATC (SEQ ID NO: 110) or a fragment thereof. In some embodiments, the fragment consists essentially of, or consists of the sequence of CCGTACGGCG-GCGGTCAGGGGCCAAAGTGAGTGTGGCTGG (SEQ ID NO: 111).

In some embodiments, the aptamer that binds progesterone consists essentially of, or consists of the nucleotide sequence of ATACGAGCTTGTTCAATACCCATTC-CGCTCTTAGGCGGTCTCCCATTTATCTCCGTGG TGATAGTAAGAGCAATC (SEQ ID NO: 140) or a fragment thereof. In some embodiments, the fragment consists essentially of, or consists the sequence of CCCATTC-CGCTCTTAGGCGGTCTCCCATTTATCTCCGTGG (SEQ ID NO: 141).

In some embodiments, the aptamer that binds progesterone consists essentially of, or consists the nucleotide sequence of ATACGAGCTTGTTCAATAGATTGGGAAT-TGCACCTTTACCTTGATGGTCGTTGTGTTG TGA-TAGTAAGAGCAATC (SEQ ID NO: 142) or a fragment thereof. In some embodiments, the fragment consists essentially of, or consists of the sequence of GATTGGGAATT-GCACCTTTACCTTGATGGTCGTTGTGTTG (SEQ ID NO: 143).

In some embodiments, the aptamer that binds progesterone consists essentially of, or consists of the nucleotide sequence of ATACGAGCTTGTTCAATAGGCGAGATG-GTGGAGCAGGTATGCCGTTGGCGGGTCGG GGTGA-TAGTAAGAGCAATC (SEQ ID NO: 146) or a fragment thereof. In some embodiments, the fragment consists essentially of, or consists of the sequence of GGCGAGATGGTG-GAGCAGGTATGCCGTTGGCGGGTCGGGG (SEQ ID NO: 147).

In some embodiments, the aptamer binds progesterone; comprises a sequence that has at least about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity to a sequence selected from SEQ ID NOs: 76-111, 140-143, 146 and 147; and in some embodiments, selectively binds progesterone. In some embodiments, the aptamer consists essentially of, or consists of a sequence selected from SEQ ID NOs: 76-111, 140-143, 146 and 147.

In some embodiments, the aptamer binds progesterone; comprises a sequence that has at least about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity to a sequence selected from SEQ ID NOs: 86, 102, 76-85, 87-101, 103-111, 140-143, 146 and 147; and in some embodiments, selectively binds progesterone. In some embodiments, the aptamer consists essentially of, or consists of a sequence selected from SEQ ID NOs: 86, 102, 76-85, 87-101, 103-111, 140-143, 146 and 147.

In some embodiments the aptamer that binds progesterone is a polynucleotide of less than 80 nucleotides in length.

In some embodiments the aptamer that binds progesterone is a polynucleotide of about 73 or about 77 nucleotides in length, or of about 74 to 76 nucleotides in length, or of 70 to 80 nucleotides in length and comprises or consists essentially of, or consists of SEQ ID NO: 86 or SEQ ID NO: 102.

In some embodiments the aptamer that binds BPA is a polynucleotide comprising a sequence that has at least about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity to SEQ ID NOs: 86 or 102.

In some embodiments the aptamer that binds BPA is a polynucleotide consisting essentially of, or consisting of a sequence that has at least about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity to SEQ ID NOs: 86 or 102.

In some embodiments, the aptamer binds testosterone.

In some embodiments, the aptamer that binds testosterone comprises the nucleotide sequence of ATACGAGCTTGT-TCAATAACGCTGTTACAATGGCAATATGACTCTTC-CGGAAGGTGTA TGATAGTAAGAGCAATC (SEQ ID NO: 112) or a fragment thereof. In some embodiments, the fragment comprises the sequence of ACGCTGTTACAATG-GCAATATGACTCTTCCGGAAGGTGTA (SEQ ID NO: 113).

In some embodiments, the aptamer that binds testosterone comprises the nucleotide sequence of ATACGAGCTTGT-TCAATACATAATGGCGTCCCCCTCAAGCTTGAACG-GTACGGGGTG CTGATAGTAAGAGCAATC (SEQ ID NO: 114) or a fragment thereof. In some embodiments, the fragment comprises the sequence of CATAATGGCGTC-CCCCTCAAGCTTGAACGGTACGGGGTGC (SEQ ID NO: 115).

In some embodiments, the aptamer that binds testosterone comprises the nucleotide sequence of ATACGAGCTTGT-TCAATAATCCCTATCTTCACTACAGTTAGTGACAG-GTGCATTGTCT TGATAGTAAGAGCAATC (SEQ ID NO: 116) or a fragment thereof. In some embodiments, the fragment comprises the sequence of ATCCCTATCTTCAC-TACAGTTAGTGACAGGTGCATTGTCT (SEQ ID NO: 117).

In some embodiments, the aptamer that binds testosterone comprises the nucleotide sequence of ATACGAGCTTGT-TCAATAACTGTCTCCCGTATCCCCTCCAAACGTC-CAGGTTCGTCTT TGATAGTAAGAGCAATC (SEQ ID NO: 118) or a fragment thereof. In some embodiments, the fragment comprises the sequence of ACTGTCTCCCG-TATCCCTCCAAACGTCCAGGTTCGTCTT (SEQ ID NO: 119).

In some embodiments, the aptamer that binds testosterone comprises the nucleotide sequence of ATACGAGCTTGT-TCAATATTACAACGTTTACTTCATCTTTAAGTCTA-CATGCGGCTAGT GATAGTAAGAGCAATC (SEQ ID NO: 120) or a fragment thereof. In some embodiments, the fragment comprises the sequence of TTACAACGTTTACT-TCATCTTTAAGTCTACATGCGGCTAG (SEQ ID NO: 121).

In some embodiments, the aptamer that binds testosterone comprises the nucleotide sequence of ATACGAGCTTGT-TCAATAGCCCTTTACACCATTCATGCCGCTCT-TATCGGTAGTCGCG TGATAGTAAGAGCAATC (SEQ ID NO: 122) or a fragment thereof. In some embodiments, the fragment comprises the sequence of GCCCTTTACAC-CATTCATGCCGCTCTTATCGGTAGTCGCG (SEQ ID NO: 123).

In some embodiments, the aptamer that binds testosterone comprises the nucleotide sequence of ATACGAGCTTGT-TCAATACATATTTTCGTATCCTACAACGTTTAATTG-TACGGCGGATT GATAGTAAGAGCAATC (SEQ ID NO: 124) or a fragment thereof. In some embodiments, the fragment comprises the sequence of CATATTTTCGTATC-CTACAACGTTTAATTGTACGGCGGAT (SEQ ID NO: 125).

In some embodiments, the aptamer that binds testosterone comprises the nucleotide sequence of ATACGAGCTTGT-TCAATAGCGTTTAGCGTTCAATTCATCCCGC-TATCTGGCTGTATCG TGATAGTAAGAGCAATC (SEQ ID NO: 126) or a fragment thereof. In some embodiments, the fragment comprises the sequence of GCGTTTAGCGT-TCAATTCATCCCGCTATCTGGCTGTATCG (SEQ ID NO: 127).

In some embodiments, the aptamer that binds testosterone comprises the nucleotide sequence of ATACGAGCTTGT-TCAATATGCGCAGAACATTCTCCGTAT-GAAGGTTTTCGATACGGGA TGATAGTAAGAG-CAATC (SEQ ID NO: 128) or a fragment thereof. In some embodiments, the fragment comprises the sequence of TGCGCAGAACATTCTCCGTATGAAGGTTTTCGA-TACGGGA (SEQ ID NO: 129).

In some embodiments, the aptamer that binds testosterone comprises the nucleotide sequence of ATACGAGCTTGT-TCAATACAATGTGCACCGGGAGACCTATTCCGC-CCACCAGATCCT ATGATAGTAAGAGCAATC (SEQ ID NO: 144) or a fragment thereof. In some embodiments, the fragment comprises the sequence of CAATGTGCAC-CGGGAGACCTATTCCGCCCACCAGATCCTA (SEQ ID NO: 145).

In some embodiments, the aptamer that binds testosterone consists essentially of, or consists of the nucleotide sequence of ATACGAGCTTGTTCAATAACGCTGTTACAATG-GCAATATGACTCTTCCGGAAGGTGTA TGATAG-TAAGAGCAATC (SEQ ID NO: 112) or a fragment thereof. In some embodiments, the fragment consists essentially of, or consists of the sequence of ACGCTGTTACAATG-GCAATATGACTCTTCCGGAAGGTGTA (SEQ ID NO: 113).

In some embodiments, the aptamer that binds testosterone consists essentially of, or consists of the nucleotide sequence of ATACGAGCTTGTTCAATACATAATGGCGTC-CCCCTCAAGCTTGAACGGTACGGGGTG CTGATAG-TAAGAGCAATC (SEQ ID NO: 114) or a fragment thereof. In some embodiments, the fragment consists essentially of, or consists of the sequence of CATAATGGCGTCCCCCT-CAAGCTTGAACGGTACGGGGTGC (SEQ ID NO: 115).

In some embodiments, the aptamer that binds testosterone consists essentially of, or consists of the nucleotide sequence of ATACGAGCTTGTTCAATAATCCCTATCTTCACTA-CAGTTAGTGACAGGTGCATTGTCT TGATAG-TAAGAGCAATC (SEQ ID NO: 116) or a fragment thereof. In some embodiments, the fragment consists essentially of, or consists of the sequence of ATCCCTATCTTCACTACA-GTTAGTGACAGGTGCATTGTCT (SEQ ID NO: 117).

In some embodiments, the aptamer that binds testosterone consists essentially of, or consists of the nucleotide sequence of ATACGAGCTTGTTCAATAACTGTCTCCCGTATC-CCCTCCAAACGTCCAGGTTCGTCTT TGATAG-TAAGAGCAATC (SEQ ID NO: 118) or a fragment thereof. In some embodiments, the fragment consists essentially of, or consists of the sequence of ACTGTCTCCCGTATC-CCCTCCAAACGTCCAGGTTCGTCTT (SEQ ID NO: 119).

In some embodiments, the aptamer that binds testosterone consists essentially of, or consists of the nucleotide sequence of ATACGAGCTTGTTCAATATTACAACGTTTACT-TCATCTTTAAGTCTACATGCGGCTAGT GATAG-TAAGAGCAATC (SEQ ID NO: 120) or a fragment thereof. In some embodiments, the fragment consists essentially of, or consists of the sequence of TTACAACGTTTACT-TCATCTTTAAGTCTACATGCGGCTAG (SEQ ID NO: 121).

In some embodiments, the aptamer that binds testosterone consists essentially of, or consists of the nucleotide sequence of ATACGAGCTTGTTCAATAGCCCTTTACACCAT-TCATGCCGCTCTTATCGGTAGTCGCG TGATAG-TAAGAGCAATC (SEQ ID NO: 122) or a fragment thereof. In some embodiments, the fragment consists essentially of, or consists of the sequence of GCCCTTTACACCATTCAT-GCCGCTCTTATCGGTAGTCGCG (SEQ ID NO: 123).

In some embodiments, the aptamer that binds testosterone consists essentially of, or consists of the nucleotide sequence of ATACGAGCTTGTTCAATACATATTTTCGTATCCTA-CAACGTTTAATTGTACGGCGGATT GATAGTAAGAG-CAATC (SEQ ID NO: 124) or a fragment thereof. In some embodiments, the fragment consists essentially of, or consists of the sequence of CATATTTTCGTATCCTA-CAACGTTTAATTGTACGGCGGAT (SEQ ID NO: 125).

In some embodiments, the aptamer that binds testosterone consists essentially of, or consists of the nucleotide sequence of ATACGAGCTTGTTCAATAGCGTTTAGCGTTCAAT-TCATCCCGCTATCTGGCTGTATCG TGATAG-TAAGAGCAATC (SEQ ID NO: 126) or a fragment thereof. In some embodiments, the fragment consists essentially of, or consists of the sequence of GCGTTTAGCGTTCAAT-TCATCCCGCTATCTGGCTGTATCG (SEQ ID NO: 127).

In some embodiments, the aptamer that binds testosterone consists essentially of, or consists of the nucleotide sequence of ATACGAGCTTGTTCAATATGCGCAGAACATTCTC-CGTATGAAGGTTTTCGATACGGGA TGATAG-TAAGAGCAATC (SEQ ID NO: 128) or a fragment thereof. In some embodiments, the fragment consists essentially of, or consists of the sequence of TGCGCAGAACATTCTC-CGTATGAAGGTTTTCGATACGGGA (SEQ ID NO: 129).

In some embodiments, the aptamer that binds testosterone consists essentially of, or consists of the nucleotide sequence of ATACGAGCTTGTTCAATACAATGTGCACCGGGA-GACCTATTCCGCCCACCAGATCCT ATGATAG-TAAGAGCAATC (SEQ ID NO: 144) or a fragment thereof. In some embodiments, the fragment consists essentially of, or consists of the sequence of CAATGTGCACCGGGA-GACCTATTCCGCCCACCAGATCCTA (SEQ ID NO: 145).

In some embodiments, the aptamer binds testosterone; comprises a sequence that has at least about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity to a sequence selected from SEQ ID NOs: 112-129, 144 and 145; and in some embodiments, selectively binds testosterone. In some embodiments, the aptamer consists essentially of, or consists of a sequence selected from SEQ ID NOs: 112-129, 144, and 145.

In some embodiments, the aptamer binds testosterone; comprises a sequence that has at least about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity to a sequence selected from SEQ ID NOs: 122, 124, 126, 112-121, 123, 125, 127-129, 144, and 145; and in some embodiments, selectively binds testosterone. In some embodiments, the aptamer consists essentially of, or consists of a sequence selected from SEQ ID NOs: 122, 124, 126, 112-121, 123, 125, 127-129, 144, and 145.

In some embodiments the aptamer that binds testosterone is a polynucleotide of less than 80 nucleotides in length.

In some embodiments the aptamer that binds testosterone is a polynucleotide of about 73 or about 77 nucleotides in length, or of about 74 to 76 nucleotides in length, or of 70 to 80 nucleotides in length and comprises or consists essentially of, or consists of SEQ ID NO: 122, SEQ ID NO: 124 or SEQ ID NO: 126.

In some embodiments the aptamer that binds BPA is a polynucleotide comprising a sequence that has at least about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity to SEQ ID NO: 122, SEQ ID NO: 124 or SEQ ID NO: 126.

In some embodiments the aptamer that binds BPA is a polynucleotide consists essentially of, or consists of a sequence that has at least about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity to SEQ ID NO: 122, SEQ ID NO: 124 or SEQ ID NO: 126.

A polynucleotide or salt thereof of the present invention can be prepared using any methodology useful for selecting sequences that bind to a specific target. For example, an aptamer of the present invention can be identified using standard methodologies commonly known to those in the art, for example, synthesis by System Evolution of Ligands by Exponential Enrichment (SELEX). SELEX is a method for producing single stranded DNA or RNA molecules that specially bind to a target (Ellington A D & Szostak J W (1990). Nature. 346:818-822 and Blackwell T K & Weintraub H (1990) Science 250:1104-1110). During the SELEX process, a library of randomly generated polynucleotide sequences is exposed to a target substrate. The randomly generated polynucleotide sequences that fail to bind to the target substrate are removed, usually using affinity separation, and the polynucleotide sequences that are bound to the target substrate are replicated and amplified by standard amplification techniques such as polymerase chain reaction (PCR). The amplified sequences can be subject to further SELEX rounds and elution conditions can be varied to identify polynucleotide sequences having the highest binding affinity for the target substrate. Once identified, an aptamer of the present invention can be synthesized readily by a person of skill in the art in accordance with known methods of synthesizing nucleic acids such as direct synthesis or through the use of recombinant DNA vectors.

Polynucleotide-Agent Complex

In some embodiments, a polynucleotide or salt thereof of the present invention (e.g., an aptamer of the present invention) forms a complex with one or more complex-forming agents and provides a polynucleotide-agent complex. A "polynucleotide-agent complex" includes a complex in which its polynucleotide component is in the form of a salt. Where the polynucleotide or salt thereof forms a complex with two or more agents, the agents can be of the same or different type. In some embodiments, the agent is a particle or non-particle. In some embodiments, the agent is a nanoparticle (NP) (e.g., a polymer NP), microparticle, semiconducting particle, quantum dot, radioactive substance (e.g., radioisotope, radionuclide, radiolabel or radiotracer), dye, contrast agent, fluorescent molecule, phosphorescent molecule, bioluminescent molecule, chemiluminescent molecule, chromophore, photoaffinity molecule, colored particle or ligand, enzyme, or enhancing agent (e.g., paramagnetic ion). In some embodiments, the agent comprises a noble metal (e.g., gold, ruthenium, rhodium, palladium, iridium, osmium, silver, or platinum) that is in salt form or has an oxidation state of zero.

Examples of fluorescent and luminescent molecules include, but are not limited to, a variety of organic or inorganic small molecules commonly referred to as "dyes," "labels," or "indicators," such as fluorescein, rhodamine, an acridine dye, an Alexa dye, and a cyanine dye.

Examples of enzymes include, but are not limited to, horseradish peroxidase, alkaline phosphatase, acid phosphatase, glucose oxidase, β-galactosidase, β-glucoronidase or β-lactamase. Where the polynucleotide or salt thereof forms a complex with an enzyme, the complex can further comprise a chromogen, a fluorogenic label or compound or a luminogenic compound that generates a detectable signal.

Examples of radioactive substances include, but are not limited to, compounds comprising $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{77}$As, $^{86}$Y, $^{90}$Y, $^{89}$Sr, $^{89}$Zr, $^{94}$Tc, $^{94}$Tc, $^{99}$Tc, 99Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{159}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra or $^{225}$Ac.

Examples of paramagnetic ions include, but are not limited to, ions of transition and lanthanide metals (e.g., metals having atomic numbers of 21-29, 42, 43, 44, or 57-71). These metals include ions of Cr, V, Mn, Fe, Co, Ni, Cu, La, Ce, Pr, Nd, Pm, Sm, Eu, Gd, Tb, Dy, Ho, Er, Tm, Yb and Lu.

Examples of fluorescent labels or compounds include, but are not limited to, Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and Texas Red.

In some embodiments, the complex comprises a polynucleotide or salt thereof that is conjugated to the agent. In other embodiments, the complex comprises a polynucleotide or salt thereof that is not conjugated to the agent. In some embodiments, the complex comprises a polynucleotide or salt thereof that is reversibly bound to the agent. In other embodiments, the complex comprises a polynucleotide or salt thereof that is irreversibly bound to the agent.

In some embodiments, the polynucleotide or salt thereof is an aptamer that adsorbs on at least a portion of the outer surface of the agent (e.g., at least about 10%, 20%, 30%, 40%, 50%, 60%, 70%, 80%, 90%, or 100% of the surface, or at least about 20% to 100%, about 30% to 90% or about 40% to 85%), e.g., where the agent is a particle, such as an NP, a microparticle, or a quantum dot. In some embodiments, the polynucleotide or salt thereof is an aptamer that, when admixed with an NP, reversibly adsorbs on at least a portion of the outer surface of the nanoparticle to form an aptamer-coated NP. In some embodiments, the aptamer-coated particle is stable in solutions containing salt (e.g., the aptamer remains complexed with the particle in salt solutions), e.g., in salt (e.g., NaCl, MgCl$_2$, KCl, or CaCl$_2$) concentrations of about 5 mM to about 50 mM, of about 10 mM to about 40 mM, of about 20 mM to about 35 mM or of about 30 mM ionic strength. In some embodiments, there is an increase in the ζ-potential value of the aptamer-coated particle when compared to an uncoated particle (increasing the ζ-potential value means that the value becomes more negative, which is readily understood and appreciated by those of skill in the art). In some embodiments, there is an increase in the ζ-potential value of the particles, for example from about −23.5 mV (±0.28) to about −40.2 mV (±0.9), which confirms adsorption of the aptamer on the outer surface of the particles. In some embodiments, the aptamer-coated particles dispersible in solution and, in some embodiments, are stable (e.g., the aptamer remains complexed with the particle in salt solutions, e.g., in a NaCl, $MgCl_2$, KCl, or $CaCl_2$ solution) in salt concentrations, e.g., in salt (e.g., NaCl, $MgCl_2$, KCl, or $CaCl_2$) concentrations of about 5 mM to about 50 mM, of about 10 mM to about 40 mM, of about 20 mM to about 35 mM or of about 30 mM ionic strength. In some embodiments, the electrostatic repulsion between an aptamer's negatively charged phosphate backbone and a particle's (e.g., an NP's) citrate surface is balanced by the attractive interaction of nitrogen bases, with the surface of the particle (Brown, K. A., et al, 2008, *J. Phys. Chem. C*, 112, 7517-7521).

In some embodiments, where the agent is a particle, e.g., an NP, the ratio of number of particles to aptamer ranges from about 1:100 to about 1:1; in another embodiment, from about 1:50 to about 1:1; and in another embodiment, from about 1:10 to about 1:3.

Methods for Making a Polynucleotide-Agent Complex

Also provided herein are methods for producing a polynucleotide-agent complex. In one embodiment, the method comprises contacting a polynucleotide or salt thereof with an agent. In one embodiment, the agent is a gold nanoparticle, and the method comprises adsorption of an aptamer onto the gold NP, such as described in Example 6.

Detection Methods

Also provided herein are methods for detecting a target molecule in a sample, comprising: contacting the sample with a polynucleotide or salt thereof and measuring a change in a property of the sample, wherein the change in property indicates the presence of the target molecule. In some embodiments, the target molecule is a small molecule. In some embodiments, the polynucleotide or salt thereof is an aptamer.

In some embodiments, the methods further comprise incubating the sample after contacting and before measuring. In some embodiments, the incubation time is from about 1 second to about 24 hours, about 6 hours to about 18 hours, about 8 hours to about 12 hours, about 1 second to about 12 hours, about 30 seconds to about 7 hours, about 1 minute to about 6 hours, about 1 minute to about 5 hours, about 1 minute to about 4 hours, about 30 minutes to about 5 hours, about 30 minutes to about 4 hours, about 45 minutes to about 4 hours, about 1 hour to about 4 hours, about 2 hours to about 4 hours, about 1 minute, about 30 minutes, about 45 minutes, about an hour, about 90 minutes, about 2 hours, about 180 minutes, about 3 hours, about 270 minutes, about 4 hours, about 6 hours, about 8 hours, about 10 hours, about 12 hours, about 18 hours, or about 24 hours.

In some embodiments, the incubation is performed at room temperature, at about 15° C. to about 30° C., about 18° C. to about 27° C., or about 25° C. In some embodiments, incubation is performed at about 2° C. to about 10° C., about 2° C. to about 5° C., or about 4° C.

In some embodiments, incubation is performed at about 15° C. to about 30° C., about 18° C. to about 27° C., or about 25° C. for about 1 second to about 12 hours, about 30 seconds to about 7 hours, about 1 minute to about 6 hours, about 1 minute to about 5 hours, about 1 minute to about 4 hours, about 30 minutes to about 5 hours, about 30 minutes to about 4 hours, about 45 minutes to about 4 hours, about 1 hour to about 4 hours, about 2 hours to about 4 hours, about 1 minute, about 30 minutes, about 45 minutes, about an hour, about 90 minutes, about 2 hours, about 180 minutes, about 3 hours, about 270 minutes, or about 4 hours. In some embodiments, incubation is performed at about 2° C. to about 10° C., about 2° C. to about 5° C., or about 4° C. for about 6 hours to about 18 hours, about 8 hours to about 12 hours, about 4 hours, about 6 hours, about 8 hours, about 10 hours, about 12 hours, about 18 hours, or about 24 hours.

In some embodiments, the change in property is a change in colour. In some embodiments, the change in colour is colorimetric. A colorimetric change can be identified or quantified using techniques such as UV-Visible spectroscopy. In some embodiments, the colorimetric change is visible to the naked eye.

Also provided herein are methods for detecting a target molecule in a sample, comprising: contacting the sample with a polynucleotide-agent complex and measuring a change in a property of the sample, wherein a change in property indicates the presence of the target molecule. In some embodiments, the target molecule is a small molecule. In some embodiments, the agent of the complex is a NP. In some embodiments, the methods further comprise incubating the sample after contacting and before measuring a change in a property of the sample.

In some embodiments, the incubation time is from about 1 second to about 24 hours, about 6 hours to about 18 hours, about 8 hours to about 12 hours, about 1 second to about 12 hours, about 30 seconds to about 7 hours, about 1 minute to about 6 hours, about 1 minute to about 5 hours, about 1 minute to about 4 hours, about 30 minutes to about 5 hours, about 30 minutes to about 4 hours, about 45 minutes to about 4 hours, about 1 hour to about 4 hours, about 2 hours to about 4 hours, about 1 minute, about 30 minutes, about 45 minutes, about an hour, about 90 minutes, about 2 hours, about 180 minutes, about 3 hours, about 270 minutes, about 4 hours, about 6 hours, about 8 hours, about 10 hours, about 12 hours, about 18 hours, or about 24 hours.

In some embodiments, the incubation is performed at room temperature, at about 15° C. to about 30° C., about 18° C. to about 27° C., or about 25° C. In some embodiments, incubation is performed at about 2° C. to about 10° C., about 2° C. to about 5° C., or about 4° C.

In some embodiments, incubation is performed at about 15° C. to about 30° C., about 18° C. to about 27° C., or about 25° C. for about 1 second to about 12 hours, about 30 seconds to about 7 hours, about 1 minute to about 6 hours, about 1 minute to about 5 hours, about 1 minute to about 4 hours, about 30 minutes to about 5 hours, about 30 minutes to about 4 hours, about 45 minutes to about 4 hours, about 1 hour to about 4 hours, about 2 hours to about 4 hours, about 1 minute, about 30 minutes, about 45 minutes, about an hour, about 90 minutes, about 2 hours, about 180 minutes, about 3 hours, about 270 minutes, or about 4 hours. In some embodiments, incubation is performed at about 2° C. to about 10° C., about 2° C. to about 5° C., or about 4° C. for about 6 hours to about 18 hours, about 8 hours to about 12 hours, about 4 hours, about 6 hours, about 8 hours, about 10 hours, about 12 hours, about 18 hours, or about 24 hours.

In some embodiments, the change in property is a change in colour. In some embodiments, the change in colour is colorimetric. A colorimetric change can be identified or quantified using techniques such as UV-Visible spectroscopy. In some embodiments, the colorimetric change is visible to the naked eye.

Also provided herein are methods for detecting a target molecule in a sample, comprising: contacting a polynucleotide or salt thereof with an agent to provide a polynucleotide agent complex, contacting the sample with the polynucleotide-agent complex and measuring a change in a property of the sample, wherein a change in property indicates the presence of the target molecule. In some embodiments, the target molecule is a small molecule. In some embodiments, the agent is an NP. In some embodiments, the methods further comprise incubating the sample after contacting the sample with the polynucleotide-agent complex and before measuring a change in a property of the sample.

In some embodiments, the incubation time is from about 1 second to about 24 hours, about 6 hours to about 18 hours, about 8 hours to about 12 hours, about 1 second to about 12 hours, about 30 seconds to about 7 hours, about 1 minute to about 6 hours, about 1 minute to about 5 hours, about 1 minute to about 4 hours, about 30 minutes to about 5 hours, about 30 minutes to about 4 hours, about 45 minutes to about 4 hours, about 1 hour to about 4 hours, about 2 hours to about 4 hours, about 1 minute, about 30 minutes, about 45 minutes, about an hour, about 90 minutes, about 2 hours, about 180 minutes, about 3 hours, about 270 minutes, about 4 hours, about 6 hours, about 8 hours, about 10 hours, about 12 hours, about 18 hours, or about 24 hours.

In some embodiments, the incubation is performed at room temperature, at about 15° C. to about 30° C., about 18° C. to about 27° C., or about 25° C. In some embodiments, incubation is performed at about 2° C. to about 10° C., about 2° C. to about 5° C., or about 4° C.

In some embodiments, incubation is performed at about 15° C. to about 30° C., about 18° C. to about 27° C., or about 25° C. for about 1 second to about 12 hours, about 30 seconds to about 7 hours, about 1 minute to about 6 hours, about 1 minute to about 5 hours, about 1 minute to about 4 hours, about 30 minutes to about 5 hours, about 30 minutes to about 4 hours, about 45 minutes to about 4 hours, about 1 hour to about 4 hours, about 2 hours to about 4 hours, about 1 minute, about 30 minutes, about 45 minutes, about an hour, about 90 minutes, about 2 hours, about 180 minutes, about 3 hours, about 270 minutes, or about 4 hours. In some embodiments, incubation is performed at about 2° C. to about 10° C., about 2° C. to about 5° C., or about 4° C. for about 6 hours to about 18 hours, about 8 hours to about 12 hours, about 4 hours, about 6 hours, about 8 hours, about 10 hours, about 12 hours, about 18 hours, or about 24 hours.

In some embodiments, the change in property is a change in colour. In some embodiments, the change in colour is colorimetric. A colorimetric change can be identified or quantified using techniques such as UV-Visible spectroscopy. In some embodiments, the colorimetric change is visible to the naked eye.

Figure 4:
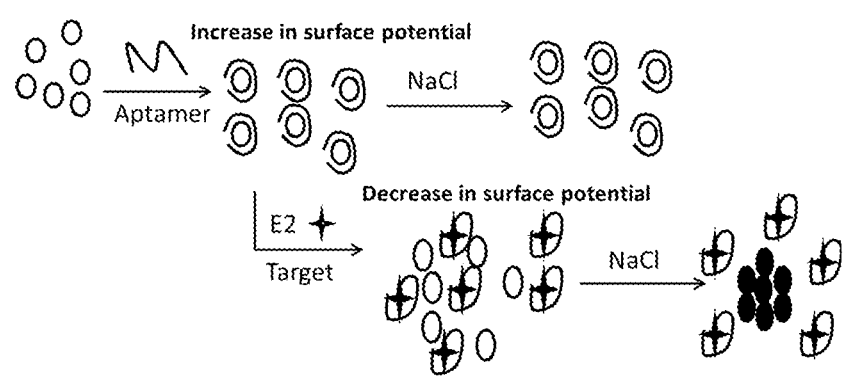
FIG. 4 is a schematic depiction of aggregation in an illustrative colorimetric assay.

In some embodiments, measuring a change in the property of a sample is performed using a colorimetric aggregation assay (FIG. 4). In some embodiments, the agent, apart from or as a component of the polynucleotide-agent complex, exhibits a change in its optical absorption when aggregation with, for example a target molecule, is induced. Where the agent is an NP that comprises a noble metal, the NP's surface plasmon resonance is very sensitive to aggregation, resulting in a strong visible signature. Other types of nanoparticles or microparticles can also provide a visible signature upon aggregation, including semiconducting particles, quantum dots or polymer NPs. In some embodiments, where the polynucleotide or salt component of a polynucleotide-agent complex is an aptamer that binds to a target molecule, a conformational change in the aptamer is induced, and the aptamer's affinity to the agent is reduced. The dispersion becomes destabilised by salt, e.g., the particles are dispersed in suspension and with the introduction of salt, the particles clump together and aggregate (e.g., McKeague, et al., 2012, *J. Nucleic Acids*, 748913 and Stoltenburg, R., et al., 2007, *Biomol. Eng.*, 24, 381-403) and the aptamer bound to the target molecule dissociates from the agent's surface. At a particular ionic strength, the presence of the target molecule is indicated by a colour change that occurs when an agent whose aptamer has dissociated from the agent's surface aggregates with the target molecule, e.g., the ionic strength can be optimised by titrating various concentrations of salt (e.g., NaCl, $MgCl_2$, KCl, $CaCl_2$) with a constant aptamer, and the absorbance at e.g., 523 nm (typically a low value) indicates that the salt tolerance has been met and complete aggregation of the AuNP occurs.

The degree of aggregation of an agent to a target molecule can be quantified using UV-visible absorption and can be evident to the naked eye. The aggregation of an agent to the target molecule can be indicated by colour observed. The colour change can depend on the concentration of the target molecule in the sample. In some embodiments, the methods further comprise quantifying the amount of target molecule in the sample or determining the concentration of the target molecule in the sample. In some embodiments, the agent is an NP. In some embodiments, the NP comprises a noble metal. In some embodiments, the target molecule is a small molecule.

In other embodiments, the change in property is a change in size, surface potential, or mobility of the agent (e.g., as disclosed in WO2014/123430, which is incorporated by reference in its entirety). In some embodiments, the methods comprise measuring a change in size of the agent, wherein a size change indicates the presence of the target molecule. In other embodiments, the methods comprise measuring a change in surface potential of the agent, wherein a surface potential change indicates the presence of the target molecule. In other embodiments, the methods comprise measuring a change in mobility of the agent, wherein a wherein a mobility change indicates the presence of the target molecule. In some embodiments, the change in size, surface potential or mobility is measured using Resistive Pulse Sensing (RPS), dynamic light scattering (DLS), circular dichroism (CD) or a combination thereof.

In some embodiments, the methods comprise contacting a sample with a polynucleotide or salt thereof that is an aptamer. In some embodiments, the methods comprise contacting a sample with an aptamer that binds, in some embodiments selectively, E2 and comprises a sequence that has at least about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity to a sequence selected from SEQ ID NOs: 3, 1-2, 4-15 or 20-26; or SEQ ID NOs: 3, 1-2, 4-15, 17, or 19-26. In some embodiments, the aptamer consists essentially of, or consists of a sequence selected from SEQ ID NOs: 3, 1-2, 4-15 or 20-26; or SEQ ID NOs: 3, 1-2, 4-15, 17, or 19-26.

In some embodiments, the methods comprise contacting a sample with an aptamer that binds androstenedione, in some embodiments selectively, and comprises a sequence that has at least about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity to a sequence selected from SEQ ID NOs: 29, 27, 28, 30-32 and 130-133. In some embodiments, the aptamer consists essentially of, or consists of a sequence selected from SEQ ID NOs: 29, 27, 28, 30-32 and 130-133.

In some embodiments, the methods comprise contacting a sample with an aptamer that binds BPA, in some embodiments selectively, and comprises a sequence that has at least about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity to a sequence selected from SEQ ID NOs: 53, 55, 56, 33-52, 54, 57-75 and 134-139. In some embodiments, the aptamer consists essentially of, or consists of a sequence selected from SEQ ID NOs: 53, 55, 56, 33-52, 54, 57-75 and 134-139.

In some embodiments, the methods comprise contacting a sample with an aptamer that binds progesterone, in some embodiments selectively, and comprises a sequence that has at least about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity to a sequence selected from SEQ ID NOs: 86, 102, 76-85, 87-101, 103-111, 140-143, 146 and 147. In some embodiments, the aptamer consists essentially of, or consists of a sequence selected from SEQ ID NOs: 86, 102, 76-85, 87-101, 103-111, 140-143, 146 and 147.

In some embodiments, the methods comprise contacting a sample with an aptamer that binds testosterone, in some embodiments selectively, and comprises a sequence that has at least about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity to a sequence selected from SEQ ID NOs: 122, 124, 126, 112-121, 123, 125, 127-129, 144, and 145. In some embodiments, the aptamer consists essentially of, or consists of a sequence selected from SEQ ID NOs: 122, 124, 126, 112-121, 123, 125, 127-129, 144, and 145.

In other embodiments, the methods comprise contacting a sample with a polynucleotide-agent complex, wherein the polynucleotide or polynucleotide salt component of the complex is an aptamer that binds E2, in some embodiments selectively, and comprises a sequence that has at least about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity to a sequence selected from SEQ ID NOs: 3, 1-2, 4-15 or 20-26; or SEQ ID NOs: 3, 1-2, 4-15, 17, or 19-26. In some embodiments, the aptamer consists essentially of, or consists of a sequence selected from SEQ ID NOs: 3, 1-2, 4-15 or 20-26; or SEQ ID NOs: 3, 1-2, 4-15, 17, or 19-26.

In other embodiments, the methods comprise contacting a sample with a polynucleotide-agent complex, wherein the polynucleotide or polynucleotide salt component of the complex is an aptamer that binds androstenedione, in some embodiments selectively, and comprises a sequence that has at least about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity to a sequence selected from SEQ ID NOs: 29, 27, 28, 30-32 and 130-133. In some embodiments, the aptamer consists essentially of, or consists of a sequence selected from SEQ ID NOs: 29, 27, 28, 30-32 and 130-133.

In other embodiments, the methods comprise contacting a sample with a polynucleotide-agent complex, wherein the polynucleotide or polynucleotide salt component of the complex is an aptamer that binds BPA, in some embodiments selectively, and comprises a sequence that has at least about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity to a sequence selected from SEQ ID NOs: 53, 55, 56, 33-52, 54, 57-75 and 134-139. In some embodiments, the aptamer consists essentially of, or consists of a sequence selected from SEQ ID NOs: 53, 55, 56, 33-52, 54, 57-75 and 134-139.

In other embodiments, the methods comprise contacting a sample with a polynucleotide-agent complex, wherein the polynucleotide or polynucleotide salt component of the complex is an aptamer that binds progesterone, in some embodiments selectively, and comprises a sequence that has at least about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity to a sequence selected from SEQ ID NOs: 86, 102, 76-85, 87-101, 103-111, 140-143, 146 and 147. In some embodiments, the aptamer consists essentially of, or consists of a sequence selected from SEQ ID NOs: 86, 102, 76-85, 87-101, 103-111, 140-143, 146 and 147.

In other embodiments, the methods comprise contacting a sample with a polynucleotide-agent complex, wherein the polynucleotide or polynucleotide salt component of the complex is an aptamer that selectively binds testosterone and comprises a sequence that has at least about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% sequence identity to a sequence selected from SEQ ID NOs: 122, 124, 126, 112-121, 123, 125, 127-129, 144, and 145. In some embodiments, the aptamer consists essentially of, or consists of a sequence selected from SEQ ID NOs: 122, 124, 126, 112-121, 123, 125, 127-129, 144, and 145.

In some embodiments, the methods comprise detecting a small molecule in a sample, wherein the small molecule is a hormone mimic, hormone, naturally occurring phytoestrogen, narcotic and metabolites thereof, and organohalides. In some embodiments, the small molecule is an endocrine disrupting compound, a steroidal sex hormone, metabolites or synthetic variants thereof. In some embodiments, the small molecule belongs to the estrogenic family of compounds, e.g., estrone (E1), estradiaol (also known as 17β-estradiol or E2), estriol (E3), estetrol (E4), xenoestrogens, phytoestrogens, or mycoestrogens, such as polychlorinated biphenols (also referred to as polychlorobiphenyl or PCBs), bisphenol-A (BPA), and phthalates. In some embodiments, the small molecule is daidzein, formononetin, genistein, bichanin A, coumestrol, 4'-methoxycoumestrol, repensol, trifoliol, or derivatives there of (e.g., 17α-ethynylestradiol).

In some embodiments, the small molecule is androstenedione, androstenediol, testosterone, dihydrotestosterone, pregnenolone, progesterone (P4), 17α-hydroxyprogesterone, Bis (4-hydroxyphenyl) methane (also referred to as bisphenol-F or BPF), cholesterol, adenosine, triclosan, a synthetic steroid such as diethylstilboestrol (DES), cocaine, heroin, tetrahydrocannabinol (THC), or any derivative or metabolite thereof. In other embodiments, the small molecule is an isoflavone, lignan, coumestan, organohalide (e.g., organochlorine), polychlorinated organic compound, alkylphenol, or alkylphenol ethoxylate, In some embodiments, the small molecule is a hormone or a marker of a condition of disease in a body. For example, in some embodiments, the method comprises detecting a hormone and/or metabolite that establishes a status in an animal, such as the fertility status of a subject. In some embodiments, the small molecule is a known marker of disease, for example a cancer gene. In some embodiments, the method comprises detecting a known marker of disease, e.g., cancer marker, a molecule associated with infection, or a metabolite associated with a particular condition.

In some embodiments, the sample isolated or collected from an environmental or biological source, e.g., located ex vivo. The sample can be of biological origin, isolated from an animal or be collected from the environment. Sources of samples may include without limitation, for example, soils, waterways, tissue, blood, serum, urine, saliva, faeces, hair and wool. The sample may be an environmental sample, for example a water sample, soil sample, or even a plant sample. Alternatively, the sample may be from an animal, for example a tissue sample, a hair or wool sample, a urine sample, a blood sample, a serum sample, a saliva sample or a fecal sample.

In some embodiments, the methods can detect a target molecule whose concentration in a sample ranges from about 1 pM to about 100 µM. In some embodiments, the methods can detects a target molecule whose concentration in the sample ranges from about 200 pM to about 400 nM. In some embodiments, the target molecule is a small molecule.

The examples described herein are for purposes of illustrating embodiments of the invention. Other embodiments, methods, and types of analyses are within the capabilities of persons of ordinary skill in the art and need not be described in detail herein. Other embodiments within the scope are considered to be part of this invention.

EXAMPLES

The aptamers were dissolved in Milli-Q water and stored at −5° C. prior to use. Milli-Q water was used in all experiments (unless stated), and all other chemicals are of analytical grades purchased from standard chemical suppliers.

Example 1: Dot Blot Assay for Aptamers that Bind 17β-estradiol (E2)

Nitrocellulose membranes were immersed in BWB (Binding and Washing Buffer: 2 mM TRIS-HCl, pH 7.5 containing 10 mM NaCl, 0.5 mM KCl, 0.2 mM $MgCl_2$, 0.1 mM $CaCl_2$, 5% v/v EtOH; 1% v/v IGEPAL® ((Octylphenoxy)polyethoxyethanol) non-ionic surfactant) for 10 minutes before drying. 17β-estradiol (E2), progesterone (P4), androstenedione (Andro), bisphenol-A (BPA), testosterone (T), and triclosan were each dissolved in ethanol (e.g., stock solution of 50 mg per millilitre of ethanol of E2, P4, Andro, BPA, T, and triclosan), spotted onto the membranes and then immersed in blotto blocking solution for 2 hours at room temperature.

The biotin-labeled aptamers (having sequences as referred to in Table 1) in 3.16 µM in BWB were incubated individually with the membranes containing different amounts (600 nmol, 300 nmol, 150 nmol, 75 nmol, 37.5 nmol, and 17.25 nmol) of E2, P4, T, Andro, BPA and triclosan, overnight at 4° C. on a rocking incubator (15 oscillations/min). Non-specifically bound aptamers were removed by rinsing the membranes three times with BWB (10 minutes on a rocking incubator 40 oscillations/min).

The bound substrate-aptamer conjugates were visualized using chemoluminescence by incubation with streptavidin-peroxidase conjugate (167 ng/mL in BWB). The incubation was left for 2 hours at room temperature. The washing of the aptamer was repeated using BWB to remove non-specifically bound streptavidin-peroxidase conjugate from the surface of the membranes. Chemoluminescence reaction solution for visualization (0.1 M Tris-HCl pH 8.5, 25 µM luminal, 396 µM p-coumaric acid, and 0.01% of hydrogen peroxide in deionized $H_2O$), was prepared immediately before use. Membranes were incubated in the chemoluminescence solution for 1 minute at room temperature in a darkroom and then immediately placed on a clear plastic backing, wrapped using clear plastic wrap and placed in an x-ray cassette. X-ray films were carefully placed on top of the membranes and exposed for 15 minutes. The films were developed by soaking twice in GBX developing solution for 3 minutes and rinsed with deionized $H_2O$ between soaking.

The results of the E2 aptamer dot blot assay (average of 3 assays) are presented in Table 1, in which "Y" indicates detection of the aptamer bound to the immobilized small molecule target (i.e., E2, P4, T, Andro, BPA or triclosan), and "N" indicates no detection the aptamer bound to the immobilized small molecule target.

TABLE 1

| SEQ ID NO. | Amount of E2 (moles) | | | | | | P4 | T | Andro | BPA | Triclosan |
|---|---|---|---|---|---|---|---|---|---|---|---|
| | 600 | 300 | 150 | 75 | 37.5 | 17.25 | | | | | |
| 1 | Y | Y | Y | N | N | N | N | N | N | N | N |
| 3 | — | — | — | — | — | — | N | N | N | N | N |
| 4 | Y | Y | N | N | N | N | N | N | N | N | N |
| 6 | Y | Y | N | N | N | N | — | — | — | — | — |
| 8 | — | — | — | — | — | — | N | N | N | N | N |
| 9 | N | Y | Y | N | N | N | N | N | N | N | N |
| 11 | Y | Y | N | N | N | N | N | N | N | N | N |
| 13 | N | Y | Y | N | N | N | N | N | N | N | N |
| 15 | — | — | — | — | — | — | N | N | N | N | N |
| 16 | Y | Y | Y | Y | Y | N | N | N | N | N | N |
| 19 | — | Y | Y | Y | Y | Y | N | N | N | N | N |
| 20 | N | Y | Y | Y | N | N | N | N | N | N | N |
| 22 | — | — | — | — | — | — | — | — | — | — | — |
| 23 | N | Y | Y | Y | N | N | N | N | N | N | N |
| 25 | N | Y | Y | Y | Y | N | N | N | N | N | N |

Example 2: Dot Blot Assay for Aptamers that Bind Androstenedione

Nitrocellulose membranes were immersed in BWB for 10 minutes before drying. Androstenedione (Andro), 17β-estradiol (E2), progesterone (P4), and testosterone (T) were each dissolved in ethanol (e.g., stock solution of 50 mg per millilitre of ethanol of Andro, E2, P4, and T), spotted onto the membranes and then immersed in blotto blocking solution for 2 hours at room temperature.

The biotin-labeled aptamers (having sequences as referred to in Table 2) (3.16 µM in BWB) were incubated individually with the membranes containing different amounts (600 nmol, 300 nmol, 150 nmol, 75 nmol, 37.5 nmol, and 17.25 nmol) of Andro, E2, P4, and T overnight at 4° C. on a rocking incubator (15 oscillations/min). Non-specifically bound aptamers were removed by rinsing the membranes three times with BWB (10 minutes on a rocking incubator 40 oscillations/min).

The bound substrate-aptamer conjugates were visualized using chemoluminescence by incubation with streptavidin-peroxidase conjugate (167 ng/mL in BWB). The incubation was left for 2 hours at room temperature. The washing of the aptamer was repeated using BWB to remove non-specifically bound streptavidin-peroxidase conjugate from the surface of the membranes. Chemoluminescence reaction solution for visualization (0.1 M Tris-HCl pH 8.5, 25 μM luminal, 396 μM p-coumaric acid, and 0.01% of hydrogen peroxide in deionized $H_2O$), was prepared immediately before use. Membranes were incubated in the chemoluminescence solution for 1 minute at room temperature in a darkroom and then immediately placed on a clear plastic backing, wrapped using clear plastic wrap and placed in an x-ray cassette. X-ray films were carefully placed on top of the membranes and exposed for 15 minutes. The films were developed by soaking twice in GBX developing solution for 3 minutes and rinsed with deionized $H_2O$ between soaking.

The results of the Andro aptamer dot blot assay (three assays for each aptamer) are presented in Table 2, in which "Y" indicates detection of the aptamer bound to the immobilized small molecule target (i.e., Andro, E2, P4, or T) in at least two of the three assays, and "N" indicates no detection the aptamer bound to the immobilized small molecule target in at least two of the three assays.

TABLE 2

| SEQ ID NO. | Amount of Andro (nmoles) | | | | | | E2 | P4 | T |
|---|---|---|---|---|---|---|---|---|---|
| | 600 | 300 | 150 | 75 | 37.5 | 17.25 | | | |
| 27 | Y | — | Y | N | N | N | N | N | N |
| 27 | Y | Y | N | Y | N | N | N | N | N |
| 27 | Y | Y | N | Y | N | N | N | N | N |
| 130 | Y | Y | N | Y | N | N | N | N | N |
| 27 | Y | Y | N | Y | N | N | N | N | N |
| 27 | N | Y | N | Y | N | N | N | N | N |
| 27 | Y | Y | N | Y | N | N | N | N | N |
| 29 | Y | Y | N | Y | N | N | N | N | N |
| 31 | Y | Y | N | N | N | N | N | N | N |
| 132 | Y | Y | N | Y | N | N | N | N | N |

Example 3: Dot Blot Assay for Aptamers that Bind Bisphenol-A

Nitrocellulose membranes were immersed in BWB for 10 minutes before drying. Bisphenol-A (BPA), 17β-estradiol (E2), Bisphenol P (BPP), and Bis(4-hydroxyphenyl methane) (BPF), were each dissolved in ethanol (e.g., stock solution of 50 mg per millilitre of ethanol of BPA, BPP, and BPF), spotted onto the membranes and then immersed in blotto blocking solution for 2 hours at room temperature.

The biotin-labeled aptamers (having sequences as referred to in Table 3) (3.16 μM in BWB) were incubated individually with the membranes containing different amounts (600 nmol, 300 nmol, 150 nmol, 75 nmol, 37.5 nmol, and 17.25 nmol) of BPA, E2, BPP, and BPF, overnight at 4° C. on a rocking incubator (15 oscillations/min). Non-specifically bound aptamers were removed by rinsing the membranes three times with BWB (10 minutes on a rocking incubator 40 oscillations/min).

The bound substrate-aptamer conjugates were visualized using chemoluminescence by incubation with streptavidin-peroxidase conjugate (167 ng/mL in BWB). The incubation was left for 2 hours at room temperature. The washing of the aptamer was repeated using BWB to remove non-specifically bound streptavidin-peroxidase conjugate from the surface of the membranes. Chemoluminescence reaction solution for visualization (0.1 M Tris-HCl pH 8.5, 25 μM luminal, 396 μM p-coumaric acid, and 0.01% of hydrogen peroxide in deionized $H_2O$), was prepared immediately before use. Membranes were incubated in the chemoluminescence solution for 1 minute at room temperature in a darkroom and then immediately placed on a clear plastic backing, wrapped using clear plastic wrap and placed in an x-ray cassette. X-ray films were carefully placed on top of the membranes and exposed for 15 minutes. The films were developed by soaking twice in GBX developing solution for 3 minutes and rinsed with deionized $H_2O$ between soaking.

The results of the BPA aptamer dot blot assay (three assays for each aptamer) are presented in Table 3, in which "Y" indicates detection of the aptamer bound to the immobilized small molecule target (i.e., BPA, E2, BPP or BPF) in at least two of the three assays; "N" indicates no detection the aptamer bound to the immobilized molecule in at least two of the three assays; and "300" and "600" indicates that the aptamer bound to the immobilized small molecule target when the target was immobilized at an amount of 300 nmoles and 600 nmoles, respectively.

TABLE 3

| SEQ ID NO. | Amount of BPA (nmoles) | | | | | | E2 (nmoles) | BPP | BPF (nmoles) |
|---|---|---|---|---|---|---|---|---|---|
| | 600 | 300 | 150 | 75 | 37.5 | 17.25 | | | |
| 33 | Y | Y | N | N | N | N | 600 & 300 | N | N |
| 35 | — | — | — | — | — | — | — | — | — |
| 36 | N | Y | Y | N | N | N | 600 | N | 300 |
| 38 | N | Y | Y | N | N | N | N | N | N |
| 40 | N | Y | Y | Y | N | N | N | N | N |
| 42 | Y | Y | Y | Y | Y | N | N | N | N |
| 43 | N | N | Y | Y | Y | N | N | N | N |
| 45 | N | N | Y | Y | Y | N | N | N | N |
| 47 | N | Y | Y | Y | N | N | N | N | N |
| 49 | N | N | Y | Y | Y | N | N | N | N |
| 51 | N | Y | Y | Y | Y | N | N | N | 600 |
| 53 | N | N | Y | Y | Y | N | N | N | N |
| 55 | Y | Y | Y | Y | Y | N | N | N | N |
| 56 | Y | Y | Y | N | N | N | N | N | N |
| 56 | Y | Y | Y | Y | Y | N | N | N | N |
| 56 | Y | Y | Y | N | N | N | N | Y | N |

TABLE 3-continued

| SEQ ID NO. | Amount of BPA (nmoles) | | | | | | E2 (nmoles) | BPP | BPF (nmoles) |
|---|---|---|---|---|---|---|---|---|---|
| | 600 | 300 | 150 | 75 | 37.5 | 17.25 | | | |
| 62 | Y | Y | Y | Y | Y | N | N | N | N |
| 58 | Y | Y | Y | N | N | N | N | N | Y |
| 56 | Y | Y | Y | N | Y | N | N | N | N |
| 56 | N | Y | Y | Y | N | N | N | N | N |
| 60 | Y | N | Y | Y | Y | N | N | N | N |
| 56 | N | Y | Y | Y | Y | N | N | N | N |
| 62 | Y | Y | Y | Y | Y | N | N | N | N |
| 64 | Y | Y | Y | N | N | N | N | N | N |
| 56 | N | Y | Y | Y | Y | N | N | N | N |
| 66 | N | Y | Y | N | N | N | N | N | N |
| 68 | Y | Y | Y | Y | Y | N | N | N | N |
| 134 | Y | Y | Y | Y | N | N | N | N | N |
| 136 | Y | Y | Y | Y | Y | N | N | N | N |
| 138 | Y | Y | Y | Y | N | N | N | N | N |
| 70 | Y | Y | Y | Y | Y | N | N | N | N |
| 72 | N | Y | Y | Y | Y | N | N | N | N |
| 74 | Y | Y | Y | Y | Y | N | N | N | N |

Example 4: Dot Blot Assay for Aptamers that Bind Progesterone

Nitrocellulose membranes were immersed in BWB for 10 minutes before drying. Progesterone (P4), 17β-estradiol (E2), androstenedione (Andro), bisphenol-A (BPA), testosterone (T) and triclosan were each dissolved in ethanol (e.g., stock solution of 50 mg per millilitre of ethanol of E2, P4, Andro, BPA, T, and triclosan), spotted onto the membranes and then immersed in blotto blocking solution for 2 hours at room temperature.

The biotin-labeled aptamers (having sequences as referred to in Table 4) (3.16 µM in BWB) with different sequences were incubated individually with the membranes containing different amounts (600 nmol, 300 nmol, 150 nmol, 75 nmol, 37.5 nmol, and 17.25 nmol) of P4, E2, T, Andro, BPA and triclosan, overnight at 4° C. on a rocking incubator (15 oscillations/min). Non-specifically bound aptamers were removed by rinsing the membranes three times with BWB (10 minutes on a rocking incubator 40 oscillations/min).

The bound substrate-aptamer conjugates were visualized using chemoluminescence by incubation with streptavidin-peroxidase conjugate (167 ng/mL in BWB). The incubation was left for 2 hours at room temperature. The washing of the aptamer was repeated using BWB to remove non-specifically bound streptavidin-peroxidase conjugate from the surface of the membranes. Chemoluminescence reaction solution for visualization (0.1 M Tris-HCl pH 8.5, 25 µM luminal, 396 µM p-coumaric acid, and 0.01% of hydrogen peroxide in deionized H₂O), was prepared immediately before use. Membranes were incubated in the chemoluminescence solution for 1 minute at room temperature in a darkroom and then immediately placed on a clear plastic backing, wrapped using clear plastic wrap and placed in an x-ray cassette. X-ray films were carefully placed on top of the membranes and exposed for 15 minutes. The films were developed by soaking twice in GBX developing solution for 3 minutes and rinsed with deionized H₂O between soaking.

The results of the P4 aptamer dot blot assay (three assays per aptamer) are presented in Table 4, in which "Y" indicates detection of the aptamer bound to the immobilized small molecule target (i.e., P4, E2, T, Andro, BPA, or triclosan) in at least two of the three assays; "N" indicates no detection the aptamer bound to the immobilized small molecule target in at least two of the three assays; and "NA" indicates data not available.

TABLE 4

| SEQ ID NO. | Amount of P4 (nmoles) | | | | | | E2 | T | Andro | BPA | Triclosan |
|---|---|---|---|---|---|---|---|---|---|---|---|
| | 600 | 300 | 150 | 75 | 37.5 | 17.25 | | | | | |
| 76 | Y | Y | Y | Y | N | N | N | Y | Y | N | N |
| 78 | Y | Y | Y | N | N | N | Y | Y | N | N | N |
| 78 | N | Y | Y | Y | N | N | Y | N | N | N | N |
| 80 | N | Y | Y | Y | N | N | N | Y | N | N | N |
| 82 | Y | Y | Y | Y | N | N | N | N | N | N | N |
| 84 | N | Y | Y | N | Y | N | N | Y | N | N | N |
| 86 | Y | Y | Y | Y | Y | N | N | N | N | N | N |
| 88 | Y | Y | Y | Y | Y | N | N | N | N | N | N |
| 90 | Y | Y | Y | Y | Y | N | N | N | N | N | N |
| 140 | N | Y | Y | Y | Y | N | N | N | N | N | N |
| 92 | N | Y | Y | Y | N | N | N | Y | N | N | N |
| 94 | N | Y | Y | Y | N | N | N | N | N | N | N |
| 96 | Y | Y | Y | N | N | N | N | Y | N | N | N |
| 146 | N | Y | Y | Y | N | N | N | N | N | N | N |
| 98 | NA | NA | NA | NA | NA | NA | NA | NA | NA | NA | NA |
| 78 | NA | NA | NA | NA | NA | NA | NA | NA | NA | NA | NA |
| 110 | NA | NA | NA | NA | NA | NA | NA | NA | NA | NA | NA |
| 100 | NA | NA | NA | NA | NA | NA | NA | NA | NA | NA | NA |
| 102 | NA | NA | NA | NA | NA | NA | NA | NA | NA | NA | NA |

TABLE 4-continued

| SEQ | Amount of P4 (nmoles) | | | | | | | | | | |
|---|---|---|---|---|---|---|---|---|---|---|---|
| ID NO. | 600 | 300 | 150 | 75 | 37.5 | 17.25 | E2 | T | Andro | BPA | Triclosan |
| 104 | NA | NA | NA | NA | NA | NA | NA | NA | NA | NA | NA |
| 106 | NA | NA | NA | NA | NA | NA | NA | NA | NA | NA | NA |
| 108 | NA | NA | NA | NA | NA | NA | NA | NA | NA | NA | NA |
| 142 | NA | NA | NA | NA | NA | NA | NA | NA | NA | NA | NA |
| 110 | NA | NA | NA | NA | NA | NA | NA | NA | NA | NA | NA |

Example 5: Dot Blot Assay for Aptamers that Bind Testosterone

Nitrocellulose membranes were immersed in BWB for 10 minutes before drying. Testosterone (T), 17β-estradiol (E2), progesterone (P4), androstenedione (Andro), bisphenol-A (BPA) and triclosan were each dissolved in ethanol (e.g., stock solution of 50 mg per millilitre of ethanol of E2, P4, Andro, BPA, T, and triclosan), spotted onto the membranes and then immersed in blotto blocking solution for 2 hours at room temperature.

The biotin-labeled aptamers (having sequences as referred to in Table 5) (3.16 µM in BWB) were incubated individually with the membranes containing different amounts (600 nmol, 300 nmol, 150 nmol, 75 nmol, 37.5 nmol, and 17.25 nmol) of P4, E2, T, Andro, BPA and triclosan, overnight at 4° C. on a rocking incubator (15 oscillations/min). Non-specifically bound aptamers were removed by rinsing the membranes three times with BWB (10 minutes on a rocking incubator 40 oscillations/min).

The bound substrate-aptamer conjugates were visualized using chemoluminescence by incubation with streptavidin-peroxidase conjugate (167 ng/mL in BWB). The incubation was left for 2 hours at room temperature. The washing of the aptamer was repeated using BWB to remove non-specifically bound streptavidin-peroxidase conjugate from the surface of the membranes. Chemoluminescence reaction solution for visualization (0.1 M Tris-HCl pH 8.5, 25 µM luminal, 396 µM p-coumaric acid, and 0.01% of hydrogen peroxide in deionized $H_2O$), was prepared immediately before use. Membranes were incubated in the chemoluminescence solution for 1 minute at room temperature in a darkroom and then immediately placed on a clear plastic backing, wrapped using clear plastic wrap and placed in an x-ray cassette. X-ray films were carefully placed on top of the membranes and exposed for 15 minutes. The films were developed by soaking twice in GBX developing solution for 3 minutes and rinsed with deionized $H_2O$ between soaking.

The results of the T aptamer dot blot assay (three assays per aptamer) are presented in Table 5 (average of 3 assays for each aptamer), in which "Y" indicates detection of the aptamer bound to the immobilized molecule (i.e., T, P4, E2, Andro, BPA, or triclosan) in at least two of the three assays; "N" indicates no detection the aptamer bound to the immobilized molecule in at least two of the three assays; and "NA" indicates data not available.

TABLE 5

| SEQ | Amount of P4 (nmoles) | | | | | | | | | | |
|---|---|---|---|---|---|---|---|---|---|---|---|
| ID NO. | 600 | 300 | 150 | 75 | 37.5 | 17.25 | E2 | T | Andro | BPA | Triclosan |
| 144 | N | Y | Y | Y | N | N | N | N | N | N | N |
| 112 | Y | Y | Y | N | Y | N | N | N | N | N | N |
| 114 | Y | Y | Y | N | Y | N | N | N | N | N | N |
| 116 | Y | Y | Y | Y | NA | N | N | N | N | N | N |
| 118 | N | Y | Y | Y | Y | N | N | N | N | N | N |
| 120 | Y | Y | N | Y | Y | N | N | N | N | N | N |
| 122 | Y | Y | Y | N | Y | N | N | N | N | N | N |
| 124 | N | Y | Y | Y | Y | N | N | N | N | N | N |
| 126 | Y | Y | Y | Y | Y | N | N | N | N | N | N |
| 128 | N | Y | Y | Y | Y | N | N | N | N | N | N |

Example 6: Gold Nanoparticle Binding Assay

Gold Nanoparticle (AuNP) Synthesis and Adsorption of Aptamer onto AuNPs

AuNPs are synthesised using the traditional citrate reduction of chloroauric acid ($HAuCl_4$). Briefly, 10 nm diameter AuNPs are synthesised by prompt addition of sodium citrate to a boiling solution of 0.1% chloroauric acid with constant stirring. The reaction is monitored by observing the colour change from transparent to deep blue followed by red wine. Boiling of the solution is maintained for 5 further minutes before cooling to room temperature. The size of the AuNPs is determined by undertaking transmission electron microscopy (TEM) and the concentration of the generated AuNPs is calculated using the UV-visible spectroscopy measurements at 523 nm and the extension coefficient of $2.7 \times 10^8$ $M^{-1}$ $cm^{-1}$ at 523 nm.

Aptamer Co-Incubation

The AuNPs solution is centrifuged for 15 minutes at 12,500 rpm to remove excess citrate ions and subsequently re-suspended in Milli-Q water to achieve a final concentration of 14 nM. Immediately, various titrations of the aptamer (nmoles from 0.1-0.4) are added to 3 mL of AuNPs and periodically vortexed to allow for the adsorption of aptamers onto the AuNP surface. Maximum adsorption is accomplished from 15-60 minutes.

Preparation of Target Molecules

Appropriate volume of 100% analytical grade EtOH is added to the distilled water to achieve a final working solution with 5% (v/v) EtOH-distilled water solution. Appropriate volumes of the target molecule stock solution (prepared in 100% EtOH) are diluted using the 5% EtOH-$dH_2O$.

Detection of Small Molecules Using AuNPs-Aptamer Sensor

The sensing of small molecules is carried out in three independent experiments. Briefly, appropriate concentrations of the prepared target molecule working solutions are added to 100 µL of AuNP-aptamer solution and incubated for 10 minutes at room temperature. Subsequently, a volume of 0.5 M NaCl solution is added to induce the aggregation of AuNPs which are no longer protected by the adsorbed aptamer molecules. The microcentrifuge tubes containing the solutions are immediately vortexed for 10 sec before analysing for visible colour change and aggregation of AuNPs. The sensing is also confirmed by UV-visible spectrophotometer analyses of the solution (100-800 nm wavelength). For experimental control, 20 µL of 5% (v/v) EtOH-natural water is added to 100 µL of AuNP-aptamer complex and treated exactly as the samples.

The Kd of particular AuNPs-aptamer sensors contain the following aptamers: SEQ ID NOs: 3, 27, 29, 53, 55, 56, 86, 102, 122, 124 and 126 were determined using the protocols above.

The following table summarizes the binding constants determined in the various experiments.

| Target | Aptamer | Binding affinity (KD) in nM |
| --- | --- | --- |
| Estradiol | SEQ ID NO: 3 | 3 nM |
| Androstenedione | SEQ ID NO: 27 | 359 nM |
| BPA | SEQ ID NO: 53 | 13 nM |
| BPA | SEQ ID NO: 55 | 6 nM |
| Progesterone | SEQ ID NO: 86 | 72.6 nM |
| Progesterone | SEQ ID NO: 102 | 1.3 µM |
| Testosterone | SEQ ID NO: 122 | 21.7 nM |

Example 7: Aptamer Binding Assay Using Fluorescence Methodology

Gel Preparation

The conjugated target molecule gels (i.e., target conjugated to molecule gels) and unconjugated control gels are washed using 1×BWB and filter dried. The dry gel is then collected and weighed before addition of distilled water to make a 50 mg/mL solution.

Preparation of HEX-Labelled Aptamers

A serial titration of hexachloro-fluorescein (HEX)-labelled aptamer using 1×BWB containing 0.1% IGEPAL® is prepared. The samples are vortexed and spun shortly, then mixed and spun down. The aptamers are then incubated for at least 1 hour at 4° C. before each assay.

Blocking of Gel

The gels are washed by taking 20 µl (50 mg/ml) of unconjugated and conjugated beads that are individually resuspended in 200 µl 1×BWB with 0.1% IGEPAL®. The gels are then centrifuged for 2 min at a speed of 13 rpm, then 180 µl of solution is carefully pipetted out of each bead suspension.

The beads are blocked by adding 90 µl of 1×BWB with 0.1% IGEPAL® and 10 µl yeast tRNA (10 mg/ml) into each bead suspension, mixed, spun down, and then incubated for 60 minutes at room temperature with gentle shaking.

The beads are then centrifuged for 2 min at a speed of 13 rpm after blocking, then 100 µl of solution is carefully pipetted out of each bead suspension.

Co-incubation

Seventy-five µl of aptamer binding solution is added into each bead suspension and the beads are incubated at room temperature for 2 hours with gentle shaking.

Gel Washing

The beads are centrifuged for 2 min at a speed of 13 rpm, then 75 µl of solution is carefully pipetted out of each bead suspension. Each bead suspension is washed three times with 200 µl of 1×BWB 0.1% IGEPAL®, in which approximately 30 µl of solution is left in the final wash.

Each bead suspension is visualized under a fluorescent microscope. Images are captured under Bright Light (14.9 ms exposure), UV, blue and green light excitation with fixed parameters and the exposure time is determined. The captured images are analysed using IGOR pro 6 (WaveMetrics, Inc., Portland, Oreg.).

Example 8: General Procedure for $K_D$ Measurement

The procedure for estimating the $K_D$ of an aptamer is based on the procedure disclosed in Alsager, O. A; Kumar, S.; Willmott, G. R.; McNatty, K. P.; Hodgkiss, J. M. Biosens. Bioelectron. 2014, 57C, 262. The aptamer is immobilized on polystyrene nanoparticles, exposed to aliquots of the small molecule that the aptamer is intended to selectively bind, and the fraction bound small molecule is measured via UV fluorescence and fit to a binding isotherm after separation of the nanoparticles from the supernatant.

For aptamers that bind E2, 200 nmol of 1-Ethyl-3-(3-dimethylaminopropyl)carbodiimide (EDC) and N-Hydroxysuccinimide (NHS) (20 µL of 0.01 M in 2-(N-morpholino)ethanesulfonic acid (MES)) is added to activate 400 µL of carboxylate polystyrene nanoparticles (NPs, $5.2 \times 10^{10}$ particle mL$^{-1}$) in MES for 40 min, followed by addition of 0.1 nmol of the aptamer and incubation overnight. The samples are centrifuged at 14000 rpm for 30 min and the supernatant is discharged. 1 mL of E2 with various concentrations in BWB containing 5% ethanol is added to the samples, sonicated for 10 mins, and incubated overnight. The samples are then centrifuged at 14000 rpm for 30 min, the supernatant is isolated, transferred to a 1 cm quartz cuvette, and the fluorescence of the unbound E2 is collected via 279 nm with a Shimadzu RF-5301PC spectrofluorophotometer. The measured fluorescence intensities at 310 nm are first converted to concentration via an E2 calibration curve. By expressing a measured E2 concentration as an unbound fraction, $f_a$, and plotting against total E2 concentration, the $K_D$ is determined by fitting to the binding isotherm in equation 1.

$$f_a = \frac{[E2]}{K_D + [E2]} \quad (1)$$

The Kd of particular aptamers of SEQ ID NOs: 3, 27, 29, 53, 55, 56, 86, 122, 124 and 126 were determined as follows:

The aptamers were used in this example are aptamers as disclosed herein of the above SEQ ID NOs. Each of the aptamers was labelled with 5'Cy5. The target molecules were used unlabelled. A total of 5 different targets were studied (Estradiol, Testosterone, Progesterone, Androstenedione and Bisphenol A).

General Setup:

1. Aptamers:

The aptamers were purchased at Sigma Aldrich Germany and solved in PBS buffer to a final concentration of 100 micro M. Respective pre-dilutions (500 nM final in 2 mM Tris-HCL pH7.5, 10 mM NaCl, 0.5 mM KCl, 0.2 mM MgCl2, 0.1 mM CaCl2 and 0.05% Pluronic) were kept on 90° C. for 3 min and immediately store on ice for 5 min. The aptamers were diluted to 10 nM with reaction buffer prior used at RT.

Initial Tests:
The aptamers were initially tested for aggregations (MST time traces). None of the aptamers showed precipitation or aggregation effects.
Also photobleaching was tested not to have an influence on the MST measurements.
MST time traces showed nicest separation at laser power between 40 and 80%.
Therefore these two setting were chosen for the later experiments.

2. Targets:
1 mg/ml stock solution of each target (also BPA) in 100% EtOH were prepared. The targets were diluted in reaction buffer (without EtOH) to a final concentration of 5% EtOH (working solution). The working solution was then diluted with reaction buffer to the respective needed concentrations (to get optimal binding curves).

Technical Setup:
The aptamers were used at a final concentration of 5 nM in the experiments. The concentration of target varied depending on the experiment. In all capillaries the reaction buffer was used in a constant manner, to prevent dilution effects.
The LED power was routinely used between 7 and 8%, whereas each technical run was performed at 40 and 80% laser power. The reaction temperature was set to 25° C.

Quality Statement:
While the experiments no sticking effects to the capillaries or aggregation effects were detected. Hence the experiments were performed at optimal technical conditions.

Data Analysis:
The MST time traces were transformed into Fnorm values, either using the Thermophoresis+TJump or TJump analysis method. The Fnorm values were plotted against the concentration of target and the data points were subsequently fitted using the Kd fit derived from the law of mass actions:

1:1 Binding Model $A + T \Leftrightarrow AT$ $F(c_T) = F_u + (F_b - F_u) * c_{AT}/c_A$ $c_{AT}/c_A = $ fraction bound $= \frac{1}{2} c_A * (c_T + c_A + K_d - \sqrt{(c_T + c_A + K_d)^2 - 4 c_T c_A})$ $F_u$ fluorescence in unbound state
$F_b$ fluorescence in bound state
$K_d$ dissociation constant, to be determined
$c_{AT}$ concentration of formed complex
$c_A$ constant concentration of molecule A (fluorescent), known
$c_T$ concentration of titrated molecule T Results:
The following table summarizes the binding constants determined in the various experiments.

| Target | Aptamer | Binding affinity (KD) in nM |
| --- | --- | --- |
| Estradiol | SEQ ID NO: 3 | 27.8 ± 10.3 nM |
| Androstenedione | SEQ ID NO: 27 | 191.6 ± 84.6 nM |

-continued

| Target | Aptamer | Binding affinity (KD) in nM |
| --- | --- | --- |
| Androstenedione | SEQ ID NO: 29 | 15.3 ± 6.5 nM |
| BPA | SEQ ID NO: 53 | 11.7 ± 5.4 nM |
| BPA | SEQ ID NO: 55 | 7.4 ± 2.6 nM |
| BPA | SEQ ID NO: 56 | 265.7 ± 123.3 nM |
| Progesterone | SEQ ID NO: 86 | 64.5 ± 31.2 nM |
| Testosterone | SEQ ID NO: 122 | 33.8 ± 14.5 nM |
| Testosterone | SEQ ID NO: 124 | 80.6 ± 17.6 nM |
| Testosterone | SEQ ID NO: 126 | 76.5 ± 32.3 nM |

Example 9: Detection of Small Molecules with AuNPs

Sample water is collected from the Hutt River, Wellington, New Zealand and pre-treated by stirring 50 mL overnight at room temperature with 1 g of activated charcoal and filtering twice through 0.22 μm syringe-filters to provide treated water. The conductivity of the treated water is measured as 100 μs cm$^{-1}$ (at 25° C. with the pH is 8). Alternatively, Milli-Q water is used instead of treated river water. Stock solutions of the target small molecules are made in ethanol before adding appropriate volumes to the treated water or Milli-Q water, and adjusting the final ethanol content to 5%, ensuring sufficient target small molecule solubility. 20 μL of the pre-treated test samples are added to 100 μL of AuNP-aptamer solution to obtain different E2 concentrations and provide a total reaction volume of 120 μL. Control samples are made up from blank water containing 5% ethanol. Samples are incubated for 10 minutes at room temperature to facilitate binding to the target. The optimized NaCl concentration determined from the salt titration experiments is added to the target detection solutions followed by gentle shaking, The samples are visually inspected after 15 minutes, and the UV-vis absorption of 5 μL aliquots is measured using a Thermo-Scientific Nano-Drop™ 1000 Spectrophotometer.

Example 10: Animal Urine Study

Rat urine is collected from sexually mature ship rats (*Rattus rattus*), filtered with 0.22 μm syringe-filters, and spiked with target small molecules and interfering molecules after adjusting the content of ethanol to 5% (control rat urine sample comprised blank rat urine containing 5% ethanol). 5 μL of spiked urine is added to 100 μL AuNP-poly-T or AuNP-aptamer, incubated at 50° C. for 10 min, followed by addition of optimised NaCl (57.4 mM), gentle shaking, visual inspection after 15 min and measurement of UV-vis absorption as described above.

Example 11: ζ-Potential Measurements For Au Nanoparticles

120 μL samples of bare AuNPs (uncoated with aptamer), AuNP-aptamer, and AuNP-aptamer in the presence of 100 nM of a target small molecule in milli-Q water, are incubated at room temperature for 1 hour and are centrifuged at 12,500 rpm for 15 minutes. The excess aptamer is removed by decantation of the supernatant and the NPs are re-suspended in 1 mL Milli-Q water. Samples are loaded in a folded capillary cell, inserted into a Zetasizer Nano ZS equipped with a 633 nm laser (Malvern Instruments, UK) and equilibrated at 25° C. for 2 minutes prior to measurement. Measurements are made in triplicate, with fixed parameters of pH 7, viscosity 0.887 mPa s, and refractive index of 1.33. The measurements are reported as average value±standard deviation.

Example 12: CD Studies 1 mL solutions of the aptamers at 400 nM and 600 nM, respectively, are prepared in water containing 5% ethanol, 23.8 mM NaCl, and 0 or 10 µM of E2. Samples are measured in a 1 cm path length quartz cell. CD spectra are measured using a Chirascan CD spectrometer instrument over the wavelength range from 200 to 400 nm, scanned at 200 nm per minute.

All publications, patents and patent applications disclosed and cited herein are incorporated herein by reference in their entirety. While the compositions and methods of this invention have been described in terms of embodiments, it will be apparent to those of skill in the art that variations may be applied to the compositions and methods, and in the steps or in the sequence of steps of the methods described herein without departing from the concept, spirit and scope of the invention.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

REFERENCES

The following references are specifically incorporated herein by reference.
US 2012/0088232
Alsager, O. A, Kumar, S., Willmott, G. R., McNatty, K. P., Hodgkiss, J. M., 2014. Biosens. Bioelectron. 57C, 262-268.
Brown, K. A., Park, S., Hamad-Schifferli, K., 2008. J. Phys. Chem. C 112, 7517-7521.
Campbell, C. G., Borglin, S. E., Green, F. B., Grayson, A., Wozei, E., Stringfellow, W. T., 2006. Chemosphere 65, 1265-80.
Cekan, P., Jonsson, E. O., Sigurdsson, S. T., 2009. Nucleic Acids Res. 37, 3990-5.
Cho, E. J., Lee, J. W., Ellington, A. D., 2009, Ann. Rev. Anal. Chem., 2(1), 241-264.
Cruz-Aguado, J. and, Penner, G., 2008. J. Agric. Food Chem. 56, 10456-61.
Ellington, A. D., Szostak, J. W., 1990. Nature 346, 818-22.
Ge, J., Xing, W., Xue, X., Liu, C., Lu, T., Liao, J., 2007. J. Phys. Chem. C 111, 17305-17310.
Geyer, H. J., Rimkus, G. G., Scheunert, I., Kaune, A., Kettrup, K. S. A., G, M. Z. D. C., Larry, M., Donald, G. H., 2000. Bioaccumulation—New Aspects and Developments. Springer-Verlag, Berlin/Heidelberg.
Grabar, K. C., Freeman, R. G., Hommer, M. B., Natan, M. J., 1995. Anal. Chem. 67, 1217-1225.
Haiss, W., Thanh, N. T. K., Aveyard, J., Fernig, D. G., 2007. Anal. Chem. 79, 4215-21.
He, J., Liu, Y., Fan, M., Liu, X., 2011. J. Agric. Food Chem. 59, 1582-6.
Huizenga, D. E., Szostak, J. W., 1995. Biochemistry 34, 656-65.
Jana, N. R., Gearheart, L., Murphy, C. J., 2001. Adv. Mater. 13, 1389-1393.
Jin, R., Wu, G., Li, Z., Mirkin, C. A., Schatz, G. C., 2003. J. Am. Chem. Soc. 125, 1643-54.
Jo, M., Ahn, J.-Y., Lee, J., Lee, S., Hong, S. W., Yoo, J.-W., Kang, J., Dua, P., Lee, D.-K., Hong, S., Kim, S., 2011. Oligonucleotides 21, 85-91.
Karsisiotis, A. I., Hessari, N. M., Novellino, E., Spada, G. P., Randazzo, A., Webba da Silva, M., 2011. Angew. Chem. Int. Ed. Engl. 50, 10645-8.
Kim, Y. S., Jung, H. S., Matsuura, T., Lee, H. Y., Kawai, T., Gu, M. B., 2007. Biosens. Bioelectron. 22, 2525-31.
Kim, Y. S., Kim, J. H., Kim, I. A., Lee, S. J., Jurng, J., Gu, M. B., 2010. Bioelectron. 26, 1644-9.
Li, H., Rothberg, L., 2004. Proc. Natl. Acad. Sci. U.S.A. 101, 14036-9.
McKeague, M., Derosa, M. C., 2012. J. Nucleic Acids 2012, 748913.
McManus, S. a, Li, Y., 2013. PLoS One 8, e64131.
Mei, Z., Chu, H., Chen, W., Xue, F., Liu, J., Xu, H., Zhang, R., Zheng, L., 2013. Biosens. Bioelectron. 39, 26-30.
Olowu, R. A.; Arotiba, O.; Maliu, S. N.; Waryo, T. T.; Baker, P.; Iwouoha, E., 2010, Sensors, 10, 9872
Olowu, R. A., Ndangili, P. M., Baleg, A. A, Ikpo, C. O., Njomo, N., Baker, P, Iwuoha, E., 2011, Int. J. Electrochem. Sci., 6, 1686
Nonaka, Y., Sode, K., Ikebukuro, K., 2010. Molecules 15, 215-25.
Redel, E., Krämer, J., Thomann, R., Janiak, C., 2009. J. Organomet. Chem. 694, 1069-1075.
Shi, H., Zhao, G., Liu, M., Fan, L., Cao, T., 2013. J. Hazard. Mater. 260, 754-761.
Song, K.-M., Cho, M., Jo, H., Min, K., Jeon, S. H., Kim, T., Han, M. S., Ku, J. K., Ban, C., 2011. Anal. Biochem. 415, 175-81.
Song, S., et al., 2008, Trends in Analytical Chemistry, 27(2), 108-117.
Stoltenburg, R., Reinemann, C., Strehlitz, B., 2007. Biomol. Eng. 24, 381-403.
Teranishi, T., Hosoe, M., Tanaka, T., Miyake, M., 1999. J. Phys. Chem. B 103, 3818-3827.
Tuerk, C., Gold, L., 1990, Science (80), 249, 505-510.
Vorlíčková, M., Kejnovská, I., Bednářová, K., Renčiuk, D., Kypr, J., 2012. Chirality 24, 691-8.
Wu, J., Chu, H., Mei, Z., Deng, Y., Xue, F., Zheng, L., Chen, W., 2012. Anal. Chim. Acta 753, 27-31.
Wu, S.-H., Chen, D.-H., 2004. J. Colloid Interface Sci. 273, 165-9.
Xue, F., Wu, J., Chu, H., Mei, Z., Ye, Y., Liu, J., Zhang, R., Peng, C., Zheng, L., Chen, W., 2012. Microchim. Acta 180, 109-115.
Yang, C., Wang, Y., Marty, J.-L., Yang, X., 2011. Biosens. Bioelectron. 26, 2724-7.
Yin, Y., Li, Z.-Y., Zhong, Z., Gates, B., Xia, Y., Venkateswaran, S., 2002. J. Mater. Chem. 12, 522-527.
Zhao, W., Brook, M. a, Li, Y., 2008. Chembiochem 9, 2363-71.
Zheng, Y., Wang, Y., Yang, X., 2011. Sensors Actuators B Chem. 156, 95-99.

The invention claimed is:

1. A deoxyribose nucleic acid or salt thereof comprising a sequence that has at least 90% sequence identity to a sequence of SEQ ID NO: 87, 103, 86, 102, 83, 85, 89, 91, 93, 95, 97, 77, 79, 101, 105, 107, 109, 111, 141, 143, 147, 82, 84, 88, 90, 92, 94, 96, 76, 78, 100, 104, 106, 108, 110, 140, 142 and 146, which deoxyribose nucleic acid or salt thereof selectively binds to progesterone.

2. The deoxyribose nucleic acid or salt thereof according to claim 1, comprising a sequence that has at least 95, 96, 97, 98, 99 or 100% sequence identity to a sequence of SEQ ID NO: 87, 103, 86, 102, 83, 85, 89, 91, 93, 95, 97, 77, 79, 81, 99, 101, 105, 107, 109, 111, 141, 143, 147, 84, 88, 90, 92, 94, 96, 76, 78, 80, 82, 98, 100, 104, 106, 108, 110, 140, 142 and 146, which deoxyribose nucleic acid or salt thereof selectively binds to progesterone.

3. The deoxyribose nucleic acid or salt thereof according to claim 1, consisting essentially of, or consisting of the sequence of, SEQ ID NO: 87, 103, 86, 102, 83, 85, 89, 91, 93, 95, 97, 77, 79, 81, 99, 101, 105, 107, 109, 111, 141, 143, 147, 82, 84, 88, 90, 92, 94, 96, 76, 78, 80, 98, 100, 104, 106, 108, 110, 140, 142 and 146, which deoxyribose nucleic acid or salt thereof selectively binds to progesterone.

4. The deoxyribose nucleic acid or salt thereof according to claim 1, consisting of the sequence of SEQ ID NO: 87, 103, 86, or 102, which deoxyribose nucleic acid or salt thereof selectively binds to progesterone.

5. The deoxyribose nucleic acid or salt thereof according to claim 1, which deoxyribose nucleic acid or salt thereof binds to progesterone with a Kd of less than about 500 nM to less than about 10 nM.

6. The deoxyribose nucleic acid or salt thereof according to claim 1, which deoxyribose nucleic acid or salt thereof binds to progesterone with a Kd of less than about 150 nM.

7. The deoxyribose nucleic acid or salt thereof according to claim 1, which deoxyribose nucleic acid or salt thereof is single stranded.

8. A deoxyribose nucleic acid-progesterone complex, comprising the deoxyribose nucleic acid according to claim 1.

9. A deoxyribose nucleic acid-agent complex comprising:
(i) a deoxyribose nucleic acid or salt thereof according to claim 1; and
(ii) an agent selected from a noble metal, nanoparticle, microparticle, quantum dot, radioactive substance, dye, contrast agent, fluorescent molecule, phosphorescent molecule, bioluminescent molecule, chemiluminescent molecule, chromophore, photoaffinity molecule, colored particle, ligand, enzyme or enhancing agent.

10. The deoxyribose nucleic acid-agent complex according claim 9 which is immobilized to a substrate.

11. The deoxyribose nucleic acid-agent complex according claim 9, wherein the deoxyribose nucleic acid or salt thereof is reversibly bound to the agent.

12. The deoxyribose nucleic acid-agent complex according claim 9, which is bound to progesterone to form a deoxyribose nucleic acid-agent-progesterone complex.

13. A method of detecting progesterone in a sample, the method comprising the steps of:
(i) contacting a sample with a deoxyribose nucleic acid-agent complex according to claim 9, which deoxyribose nucleic acid-agent complex selectively binds to progesterone when present in the sample; and
(ii) measuring a change in a property of the deoxyribose nucleic acid-agent complex;
wherein a measured change in the property of the deoxyribose nucleic acid-agent complex indicates the presence of progesterone in the sample.

14. A method according to claim 13, wherein the sample is selected from a tissue sample, hair sample, urine sample, whole blood sample, plasma sample, serum sample, saliva sample and fecal sample.

15. A method according to claim 13, further comprising quantitating the amount or concentration of progesterone in the sample.

* * * * *

UNITED STATES PATENT AND TRADEMARK OFFICE
CERTIFICATE OF CORRECTION

| | | |
|---|---|---|
| PATENT NO. | : 10,844,386 B2 | Page 1 of 1 |
| APPLICATION NO. | : 15/752201 | |
| DATED | : November 24, 2020 | |
| INVENTOR(S) | : Shalen Kumar et al. | |

It is certified that error appears in the above-identified patent and that said Letters Patent is hereby corrected as shown below:

In the Claims

At Column 97, Line 14, "NO:" should be -- NOs: --.

At Column 97, Line 22, "NO:" should be -- NOs: --.

At Column 97, Line 30, "NO:" should be -- NOs: --.

At Column 98, Line 23, "claim 9" should be -- to claim 9, --.

At Column 98, Line 25, "claim" should be -- to claim --.

At Column 98, Line 28, "claim" should be -- to claim --.

Signed and Sealed this
Twenty-second Day of June, 2021

Drew Hirshfeld
*Performing the Functions and Duties of the
Under Secretary of Commerce for Intellectual Property and
Director of the United States Patent and Trademark Office*